Figure 1A:
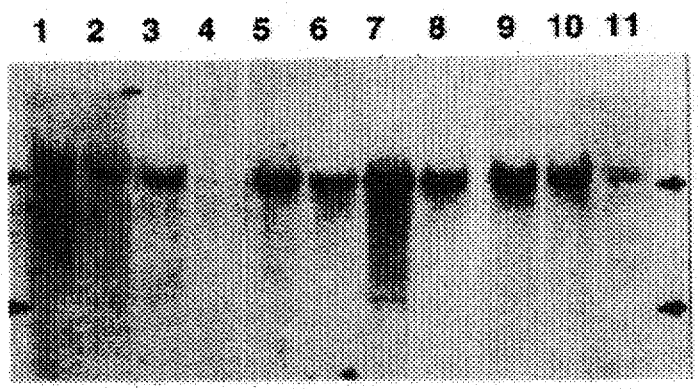

United States Patent [19]

Wilks et al.

[11] Patent Number: 5,716,818
[45] Date of Patent: Feb. 10, 1998

[54] PROTEIN TYROSINE KINASE

[75] Inventors: Andrew Frederick Wilks, Doneaster East, Australia; Andrew Ziemiecki, Berne, Switzerland; Ailsa Harpur, Mooroolbark, Australia

[73] Assignee: Ludwig Institute For Cancer Research, New York, N.Y.

[21] Appl. No.: 446,010

[22] Filed: May 19, 1995

Related U.S. Application Data

[62] Division of Ser. No. 64,067, filed as PCT/US91/08889, Nov. 26, 1991.

[30] Foreign Application Priority Data

Nov. 28, 1990 [AU] Australia ............... PK3594/90

[51] Int. Cl.$^6$ ............... C12N 9/12; C07K 7/00; C07K 14/47
[52] U.S. Cl. ............... 435/194; 530/350; 530/326; 530/328; 530/329
[58] Field of Search ............... 435/194; 530/350, 530/352, 329, 326, 328, 324, 325

[56] References Cited

PUBLICATIONS

Hanks et al. (1988) Science 2451: 42–52.
Firmbach–Kraft et al. (1990) Oncogene 5: 1329–1336.
Bernards (1991) Oncogene 6: 1185–1189.
Harpur et al. (1992). Oncogene 7: 1347–1353.
Wilks (1989) Proc. Natl. Acad. Sci. 86: 1603–1607.

*Primary Examiner*—Charles L. Patterson, Jr.
*Assistant Examiner*—Gabriele E. Bugaisky
*Attorney, Agent, or Firm*—Felfe & Lynch

[57] ABSTRACT

The present invention is directed to a novel protein tyrosine kinase comprising a polypeptide having multiple protein kinase catalytic domains and, more particularly, two kinase catalytic domains and to genetic sequences encoding same. Two such kinases are described and designated JAK1 and JAK2.

14 Claims, 34 Drawing Sheets

FIG. 2A

```
TGGCCGCCTA GCGAGCTGCC GGTCGACCCC AGCCAGCCCC AGCCAGCCGA GCGACGGGCG CTGCCTGGCC 60
CAGGGCACAC GGAAGTGCGC TTCTCTGAAG TAGCTTTGGA AAGTAGAGAA GAAAATCCAG120
TTTGCTTCTT GGAGAACACT GGACAGCTGA ATAA ATG CAG TAT CTA AAT     169
                                   Met Gln Tyr Leu Asn
                                                  -10

ATA AAA GAG GAC TGC AAT GCC ATG GCT TTC TGT GCT AAA ATG AGG    214
Ile Lys Glu Asp Cys Asn Ala Met Ala Phe Cys Ala Lys Met Arg
 -5                  +1                  5

AGC TCC AAG AAG ACT GAG GTG AAC CTG GAG GCC CCT GAG CCA GGG    259
Ser Ser Lys Lys Thr Glu Val Asn Leu Glu Ala Pro Glu Pro Gly
         10                  15                  20

GTG GAA GTG ATC TTC TAT CTG TCG GAC AGG GAG CCC CTC CGG CTG    304
Val Glu Val Ile Phe Tyr Leu Ser Asp Arg Glu Pro Leu Arg Leu
             25                  30                  35

GGC AGT GGA GAG TAC ACA GCA GAG GAA CTG TGC ATC AGG GCT GCA    349
Gly Ser Gly Glu Tyr Thr Ala Glu Glu Leu Cys Ile Arg Ala Ala
                 40                  45                  50
```

FIG. 2B

```
CAG GCA TGC CGT ATC TCT CCT CTT TGT CAC AAC CTC TTT GCC CTG      394
Gln Ala Cys Arg Ile Ser Pro Leu Cys His Asn Leu Phe Ala Leu
 55                  60                  65

TAT GAC GAG AAC ACC AAG CTC TGG TAT GCT CCA AAT CGC ACC ATC      439
Tyr Asp Glu Asn Thr Lys Leu Trp Tyr Ala Pro Asn Arg Thr Ile
 70                  75                  80

ACC GTT GAT GAC AAG ATG TCC CTC CGG CTC CAC TAC CGG ATG AGG      484
Thr Val Asp Asp Lys Met Ser Leu Arg Leu His Tyr Arg Met Arg
 85                  90                  95

TTC TAT TTC ACC AAT TGG CAT GGA ACC AAC GAC AAT GAG CAG TCA      529
Phe Tyr Phe Thr Asn Trp His Gly Thr Asn Asp Asn Glu Gln Ser
100                 105                 110

GTG TGG CGT CAT TCT CCA AAG CAG AAA AAT GGC TAC GAG AAA          574
Val Trp Arg His Ser Pro Lys Gln Lys Asn Gly Tyr Glu Lys
115                 120                 125

AAA AAG ATT CCA GAT GCA ACC CCT CTC CTT GAT GCC AGC TCA CTG      619
Lys Lys Ile Pro Asp Ala Thr Pro Leu Leu Asp Ala Ser Leu
130                 135                 140

GAG TAT CTG TTT GCT CAG GGA CAG TAT GAT TTG GTG AAA TGC CTG      664
Glu Tyr Leu Phe Ala Gln Gly Gln Tyr Asp Leu Val Lys Cys Leu
145                 150                 155
```

FIG. 2C

```
GCT CCT ATT CGA GAC CCC AAG ACC GAG CAG GAT GGA CAT GAT ATT       709
Ala Pro Ile Arg Asp Pro Lys Thr Glu Gln Asp Gly His Asp Ile
            160               165               170

GAG AAC GAG TGT CTA GGG ATG GCT GTC CTG GCC ATC TCA CAC TAT       754
Glu Asn Glu Cys Leu Gly Met Ala Val Leu Ala Ile Ser His Tyr
            175               180               185

GCC ATG AAG ATG AAG ATG CAG TTG CCA GAA CTG CCC AAG GAC ATC       799
Ala Met Lys Met Lys Met Gln Leu Pro Glu Leu Pro Lys Asp Ile
            190               195               200

AGC TAC AAG CGA TAT ATT CCA GAA ACA TTG AAT AAG TCC ATC AGA       844
Ser Tyr Lys Arg Tyr Ile Pro Glu Thr Leu Asn Lys Ser Ile Arg
            205               210               215

CAG AGG AAC CTT CTC ACC AGG ATG CGG ATA AAT AAT GTT TTC AAG       889
Gln Arg Asn Leu Leu Thr Arg Met Arg Ile Asn Asn Val Phe Lys
            220               225               230

GAT TTC CTA AAG GAA TTT AAC AAG ACC ATT TGT GAC AGC AGC           934
Asp Phe Leu Lys Glu Phe Asn Lys Thr Ile Cys Asp Ser Ser
            235               240               245
```

FIG. 2D

```
GTG TCC ACG CAT GAC CTG AAG GTG TAC TTG GCT ACC TTG GAA        979
Val Ser Thr His Asp Leu Lys Val Tyr Leu Ala Thr Leu Glu
250                 255                 260

ACT TTG ACA AAA CAT TAC GGT GCT GAA ATA TTT GAG ACT TCC ATG   1024
Thr Leu Thr Lys His Tyr Gly Ala Glu Ile Phe Glu Thr Ser Met
            265                 270                 275

TTA CTG ATT TCA TCA GAA AAT GAG ATG AAT TGG TTT CAT TCG AAT   1069
Leu Leu Ile Ser Ser Glu Asn Glu Met Asn Trp Phe His Ser Asn
        280                 285                 290

GAC GGT GGA AAC GTT CTC TAC TAC GAA GTG ATG GTG ACT GGG AAT   1114
Asp Gly Gly Asn Val Leu Tyr Tyr Glu Val Met Val Thr Gly Asn
    295                 300                 305

CTT GGA ATC CAG TGG AGG CAT AAA CCA AAT GTT TCT GTT GAA       1159
Leu Gly Ile Gln Trp Arg His Lys Pro Asn Val Ser Val Glu
310                 315                 320

AAG GAA AAA AAT AAA CTG AAG CGG AAA CTG GAA AAT AAA GAC       1204
Lys Glu Lys Asn Lys Leu Lys Arg Lys Leu Glu Asn Lys Asp
325                 330                 335

AAG AAG GAT GAG GAG AAA ATC CGG GAA TGG AAC AAT              1249
Lys Lys Asp Glu Glu Lys Ile Arg Glu Trp Asn Asn
340                 345                 350
```

FIG. 2E

```
TTT TCA TTC TTC CCT GAA ATC ACT CAC ATT GTA ATA AAG GAG TCT     1294
Phe Ser Phe Phe Pro Glu Ile Thr His Ile Val Ile Lys Glu Ser
355                 360                 365

GTG GTC AGC ATT AAC AAG CAG GAC AAC AAG AAA ATG GAA CTG AAG     1339
Val Val Ser Ile Asn Lys Gln Asp Asn Lys Lys Met Glu Leu Lys
370                 375                 380

CTC TCT TCC CAC GAG GAG GCC TTG TCC TTT GTG TCC CTG GTA GAT     1384
Leu Ser Ser His Glu Glu Ala Leu Ser Phe Val Ser Leu Val Asp
385                 390                 395

GGC TAC TTC CGG CTC ACA GCA GAT GCC CAT TAC CTC TGC ACC         1429
Gly Tyr Phe Arg Leu Thr Ala Asp Ala His Tyr Leu Cys Thr
400                 405                 410

GAC GTG GCC CCC CCG TTG ATC GTC CAC AAC ATA CAG AAT GGC TGT     1474
Asp Val Ala Pro Pro Leu Ile Val His Asn Ile Gln Asn Gly Cys
415                 420                 425

CAT GGT CCA ATC TGT ACA GAA TAC GCC ATC AAT AAA TTG CGG CAA     1519
His Gly Pro Ile Cys Thr Glu Tyr Ala Ile Asn Lys Leu Arg Gln
430                 435                 440
```

FIG. 2F

```
GAA AGC GAG GAG GGG ATG TAC GTG CTG AGG TGG AGC TGC ACC    1564
Glu Gly Ser Glu Glu Gly Met Tyr Val Leu Arg Trp Ser Cys Thr
    445                 450                 455

GAC TTT GAC AAC ATC CTC ATG ACC GTC ACC TGC TTT GAG AAG TCT    1609
Asp Phe Asp Asn Ile Leu Met Thr Val Thr Cys Phe Glu Lys Ser
    460                 465                 470

GAG CAG GTG CAG GGT GCC CAG AAG CAG TTC AAG AAC TTT CAG ATC    1654
Glu Gln Val Gln Gly Ala Gln Lys Gln Phe Lys Asn Phe Gln Ile
    475                 480                 485

GAG GTG CAG AAG GGC CGC TAC AGT CTG CAC GGT TCG GAC CGC AGC    1699
Glu Val Gln Lys Gly Arg Tyr Ser Leu His Gly Ser Asp Arg Ser
    490                 495                 500

TTC CCC AGC TTG GGA GAC CTC ATG AGC CAC CTC AAG AAG CAG ATC    1744
Phe Pro Ser Leu Gly Asp Leu Met Ser His Leu Lys Lys Gln Ile
    505                 510                 515

CTG CGC ACG GAT AAC ATC AGC TTC ATG CTA AAA CGC TGC TGC CAG    1789
Leu Arg Thr Asp Asn Ile Ser Phe Met Leu Lys Arg Cys Cys Gln
    520                 525                 530
```

FIG. 2G

```
CCC AAG CCC CGA GAA ATC TCC AAC CTG CTG GTG GCT ACT AAG AAA    1834
Pro Lys Pro Arg Glu Ile Ser Asn Leu Leu Val Ala Thr Lys Lys
    535                 540                 545

GCC CAG GAG TGG CAG CCC GTC TAC CCC ATG AGC CAG CTG AGT TTC    1879
Ala Gln Glu Trp Gln Pro Val Tyr Pro Met Ser Gln Leu Ser Phe
    550                 555                 560

GAT CTC AAG AAG AAG GAT CTG GTG CAG GGC GAG CAC CTT GGG        1924
Asp Ile Leu Lys Lys Lys Asp Leu Val Gln Gly Glu His Leu Gly
    565                 570                 575
    Iₐ

AGA GGC ACG AGA ACA CAC ATC TAT TCT GGG ACC CTG ATG GAT TAC    1969
Arg Gly Thr Arg Thr His Ile Tyr Ser Gly Thr Leu Met Asp Tyr
    580                 585                 590

AAG GAT GAC GAA GGA ACT TCT GAA GAG AAG ATA AAA GTG ATC        2014
Lys Asp Asp Glu Gly Thr Ser Glu Glu Lys Ile Lys Val Ile
    595                 600                 605
    IIₐ

CTC AAA GTC TTA GAC CCC AGC CAC AGG GAT ATT TCC CTG GCC TTC    2059
Leu Lys Val Leu Asp Pro Ser His Arg Asp Ile Ser Leu Ala Phe
    605                 615                 620
```

FIG. 2H

```
         IIIa
TTC GAG GCA GCC AGC ATG ATG AGA CAG GTC TCC CAC AAA CAC ATC    2104
Phe Glu Ala Ala Ser Met Met Arg Gln Val Ser His Lys His Ile
625                         630                 635

IVa
GTG TAC CTC TAT GGC GTC TGT GTC CGC GAC GTG GAG AAT ATC ATG    2149
Val Tyr Leu Tyr Gly Val Cys Val Arg Asp Val Glu Asn Ile Met
        640                 645                 650

Va
GTG GAA GAG TTT GTG GAA GGG GGT CCT CTG GAT CTC TTC ATG CAC    2194
Val Glu Glu Phe Val Glu Gly Gly Pro Leu Asp Leu Phe Met His
    655                 660                 665

CGG AAA AGT GAT GTC CTT ACC ACA CCA TGG AAA TTC AAA GTT GCC    2239
Arg Lys Ser Asp Val Leu Thr Thr Pro Trp Lys Phe Lys Val Ala
670                 675                 680

AAA CAG CTG GCC AGT TAC TTG GAG GAT AAA GAC CTG                2284
Lys Gln Leu Ala Ser Ala Leu Ser Tyr Leu Glu Asp Lys Asp Leu
    685                 690                 695

VIa
GTC CAT GGA AAT GTG TGT ACT AAA AAC CTC CTG GCC CGT GAG        2329
Val His Gly Asn Val Cys Thr Lys Asn Leu Leu Ala Arg Glu
700                 705                 710
```

FIG. 21

```
                                                                    VIIₐ
GGA ATC GAC AGT GAG TGT GGC CCA TTC ATC AAG CTC AGT GAC CCC        2374
Gly Ile Asp Ser Glu Cys Gly Pro Phe Ile Lys Leu Ser Asp Pro
715                 720                 725

GGC ATC CCC ATT ACG GTG CTG TCT AGG CAA GAA TGC ATT GAA CGA        2419
Gly Ile Pro Ile Thr Val Leu Ser Arg Gln Glu Cys Ile Glu Arg
            730                 735                 740
         VIIIₐ
ATC CCA TGG ATT GCT CCT GAG TGT GTT GAG GAC TCC AAG AAC CTG        2464
Ile Pro Trp Ile Ala Pro Glu Cys Val Glu Asp Ser Lys Asn Leu
        745                 750                 755
                     IXₐ
AGT GTG GCT GCT GAC AAG TGG AGC TTT GGA ACC ACG CTC TGG GAA        2509
Ser Val Ala Ala Asp Lys Trp Ser Phe Gly Thr Thr Leu Trp Glu
760                 765                 770

ATC TGC TAC AAT GGC GAG ATC CCC TTG AAA GAC AAG ACG CTG ATT        2554
Ile Cys Tyr Asn Gly Glu Ile Pro Leu Lys Asp Lys Thr Leu Ile
        775                 780                 785
                                       Xₐ
GAG AAA GAG AGA TTC TAT GAA AGC CGG TGC AGG CCA GTG ACA CCA        2599
Glu Lys Glu Arg Phe Tyr Glu Ser Arg Cys Arg Pro Val Thr Pro
790                 795                 800
                                                        XIₐ
TCA TGT AAG GAG CTG GCT GAC CTC ATG ACC CGC TGC ATG AAC TAT        2644
Ser Cys Lys Glu Leu Ala Asp Leu Met Thr Arg Cys Met Asn Tyr
        805                 810                 815
```

FIG. 2J

```
GAC CCC AAT CAG AGG CCT TTC TTC CGA GCC ATC ATG AGA GAC ATT    2689
Asp Pro Asn Gln Arg Pro Phe Phe Arg Ala Ile Met Arg Asp Ile
        820                 825                 830

AAT AAG CTT GAA GAG CAG AAT CCA GAT ATT GTT TCC AGA AAA AAA    2734
Asn Lys Leu Glu Glu Gln Asn Pro Asp Ile Val Ser Arg Lys Lys
        835                 840                 845

AAC CAG CCA ACT GAA GTG GAC CCC ACA CAT TTT GAG AAG CGC TTC    2779
Asn Gln Pro Thr Glu Val Asp Pro Thr His Phe Glu Lys Arg Phe
        850                 855                 860
                                    I

CTA AAG AGG ATC CGT GAC TTG GGA GAG GGC CAC TTT GGG AAG GTT    2824
Leu Lys Arg Ile Arg Asp Leu Gly Glu Gly His Phe Gly Lys Val
        865                 870                 875

GAG CTC TGC AGG TAT GAC TAT GAC CCC GAA GAC AAT ACA GGG GAG CAG GTG    2869
Glu Leu Cys Arg Tyr Asp Tyr Asp Pro Glu Asp Asn Thr Gly Glu Gln Val
        880                 885                 890
 II

GCT GTT AAA TCT CTG AAG CCT GAG AGT GGA GGT AAC CAC ATA GCT    2914
Ala Val Lys Ser Leu Lys Pro Glu Ser Gly Gly Asn His Ile Ala
        895                 900                 905
                    III

GAT CTG AAA AAG GAA ATC TTA AGG AAC CTC TAT CAT GAG    2959
Asp Leu Lys Lys Glu Ile Leu Arg Asn Leu Tyr His Glu
        910                 915                 920
```

FIG. 2K

```
       IV
AAC ATT GTG AAG TAC AAA GGA ATC TGC ACA GAA GAC GGA GGA AAT    3004
Asn Ile Val Lys Tyr Lys Gly Ile Cys Thr Glu Asp Gly Gly Asn
        925                 930                 935
                                                  V
GGT ATT AAG CTC ATC ATG GAA TTT CTG CCT TCG GGA AGC CTT AAG    3049
Gly Ile Lys Leu Ile Met Glu Phe Leu Pro Ser Gly Ser Leu Lys
        940                 945                 950

GAA TAT CTT CCA AAG AAT AAC AAA ATA AAC CTC AAA CAG CAG        3094
Glu Tyr Leu Pro Lys Asn Asn Lys Ile Asn Leu Lys Gln Gln
        955                 960                 965

CTA AAA TAT GCC GTT CAG ATT TGT AAG GGG ATG GAC TAT TTG GGT    3139
Leu Lys Tyr Ala Val Gln Ile Cys Lys Gly Met Asp Tyr Leu Gly
        970                 975                 980
                              VI
TCT CGG CAA TAC GTT CAC CGG GAC TTG GCA GCA AGA AAT GTC CTT    3184
Ser Arg Gln Tyr Val His Arg Asp Leu Ala Ala Arg Asn Val Leu
        985                 990                 995
                                                  VII
GTT GAG AGT GAA CAC CAA ATT GGA AAA GTG ATT GGA GAC TTC GGT TTA ACC    3229
Val Glu Ser Glu His Gln Ile Gly Lys Val Ile Gly Asp Phe Gly Leu Thr
        1000                1005                1010

AAA GCA ATT GAA ACC GAT AAG GAG TAT TAC ACC GTC AAG GAT GAC    3279
Lys Ala Ile Glu Thr Asp Lys Glu Tyr Tyr Thr Val Lys Asp Asp
        1015                1020                1025
```

FIG. 2L

```
     VIII
CGG GAC AGC CCT GTG TTT TGG TAT GCT CCA GAA TGT TTA ATG CAA    3319
Arg Asp Ser Pro Val Phe Trp Tyr Ala Pro Glu Cys Leu Met Gln
           1030               1035               1040
                                                    IX
TCT AAA TTT TAT ATT GCC TCT GAC GTC TGG TCT TTT GGA GTC ACT    3364
Ser Lys Phe Tyr Ile Ala Ser Asp Val Trp Ser Phe Gly Val Thr
           1045               1050               1055

CTG CAT GAG CTG CTG ACT TAC TGT GAT TCA GAT TCT AGT CCC ATG    3409
Leu His Glu Leu Leu Thr Tyr Cys Asp Ser Asp Ser Ser Pro Met
           1060               1065               1070

GCT TTG TTC CTG AAA ATG ATA GGC CCA ACC CAT GGC CAG ATG ACA    3454
Ala Leu Phe Leu Lys Met Ile Gly Pro Thr His Gly Gln Met Thr
           1075               1080               1085
                                                    X
GTC ACA AGA CTT GTG AAT ACG TTA AAA GAA GGA AAA CGC CTG CCG    3499
Val Thr Arg Leu Val Asn Thr Leu Lys Glu Gly Lys Arg Leu Pro
           1090               1095               1100

TGC CCA CCT AAC TGT CCA GAT GAG GTT TAT CAG CTT ATG AGA AAA    3544
Cys Pro Pro Asn Cys Pro Asp Glu Val Tyr Gln Leu Met Arg Lys
           1105               1110               1115
```

FIG. 2M

XI

```
TGC TGG GAA TTC CAA CCA TCC AAT CGG ACA AGC TTT CAG AAC CTT       3589
Cys Trp Glu Phe Gln Pro Ser Asn Arg Thr Ser Phe Gln Asn Leu
    1120                    1125                    1130

ATT GAA GGA TTT GAA GCA CTT TTA AAA TAAGAAGCAT GAATAACATT
3636
Ile Glu Gly Phe Glu Ala Leu Leu Lys
    1135                    1140

TAAATTCCAC AGATTATCAA GTCCTTCTCC TGCAACAAAT GCCCAAGTCA TTTTTTAAAA 3696
ATTTCTAATG AAAGAAGTTT GTGTTCTGTC CAAAAAGTCA CTGAACTCAT ACTTCAGTAC 3756
ATATACATGT ATAAGGCACA CTGTAGTGCT TAATATGTGT AAGGACTTCC TCTTTAAATT 3816
TGCACCAGTA ACTTAGTGAC ACATAATGAC AACCAAAATA TTTGAAAGCA CTTAAGCACT 3876
CCTCCTTGTG GAAAGAATAT ACCACCATTT CATCTGGCTA GTTCACCATC ACAACTGCAT 3936
TACCAAAAGG GGATTTTGA AAACGAGGAG TTGACCAAAA TAATATCTGA AGATGATTGC 3996
TTTTCCCTGC TGCCAGCTGA CTGAAATGTT TTCCTGGCAC ATTAATCATA GATAAAGAAG 4056
ATTGATGGAC TTAGCCCTCA AACAGTATCT ATACAGTACT AGACCATGCA TTCTTAAAAT 4116
ATTAGATACC AGGTAGTATA TATTGTTTCT GTACAAAAAT GACTGTATTC TCTCACCAGT 4176
AGGACTTAAA CTTTGTTTCT CCAGTGGCTT AGCTCCTGTT CCTTGGGTG ATCACTAG 4234
```

FIG. 3A

```
                    I                                II                                III
Domain 1   HLGRGTRTHIYSGTLMDYKDDEGTSEEKKIKVLRVLDPS...HRDISLAGGEAASM              -60aa-
Domain 2   DLGEGHFGKVELCRT.DPEDNTGE.......QVAVKSLKPES.GGNHIADLKKEIEIL             -63aa-
CDC2-H     KIGEGTYGVVYKGRH...KYYG.......QVVAMKKIRLESEEEGVPSTAIREISLL              -55aa- VII
Domain 1   SYLEDKDLVHGNVCTKNLLAREGIDSECGPFIKLSDPGIPITVLS.......RQECIERIPW.
Domain 2   DYLGSRQYVHRDLAARNVLVESE..........VKIGDFGLTKAIETDKEYYTVKDDRDSPCFM.
CDC2-H     VECHSRRVLHRDLKPQNLLIDDKG.........TIKLADGGLARAFGIPIRVYTHE...VVT.

IX
                                 VI
Domain 1   IAPECVEDSKNLSVAADKWSFGTTLWEIC-20aa-
Domain 2   YAPECLMQSKF.YIASDVWSFGVTLHELL-38aa-
CDC2-H     LMYRSPEVLLGSARYSTPVDIWSIGTIFAELA-50aa- XI
Domain 1   SRCRPVTPSCKELADLMTRCMNYDPNQRPF
Domain 2   LPCPPNCPDEVYQ..LMRKCWEFQPSNRTS
CDC2-H     LASHHVKNLDENGLDLLSKMLIYDPAKRIS
```

FIG. 5

```
              Ia                                   IIa              IIIa    70
VFHKIRNEDL IFNESLGQGT FTKIFKGVRR EVGDYGQLHE TE...VLLKV LDKAHRNYSE SFFEAASMMS   MJAK2
*$*    **  $ *  ** ** * *$ *    $ *     *   *$*** ** **   *    ********
SFDRILKKDL VQGEHLGRGT RTHIYSGTLM DYKDDEGTSE EKKIKVILKV LDPSHRDISL AFFEAASMMR   HJAK1

IVa                 Va                                         140
QLSHKHLVLN YGVCVCGEEN ILVQEFVKFG SLDTYLKKNK NSINILWKLG VAKQLAWAMH FLEEKSLIHG   MJAK2
*$****$*   *****  ** * * *** *  ** $  $   $    **  ****** *  $**$* *$**
QVSHKHIVYL YGVCVRDVEN IMVEEFVEGG PLDLFMHRKS DVLTTPWKFK VAKQLASALS YLEDKDLVHG   HJAK1

VIa               VIIa                              VIIIa            210
NVCAKNILLI REEDRRTGNP PFIKLSDPGI SITVLPKDIS SCCFQVLQER IPWVPPECIE NPKNLTLATD   MJAK2
***  **$** **         * ********* ****  $      *   ** ***$ ***$*  ***$$*  *
NVCTKNLLLA REGIDSECGP .FIKLSDPGI PITVLSR... ....QECIER IPWIAPECVE DSKNLSVAAD   HJAK1

IXa                    Xa                           XIa              280
KWSFGTTLWE ICSGGDKPLS ALDSQRKLQF YEDKHQLPAP KWTELANLIN NCMDYEPDFR PAFRAVIRDL   MJAK2
**********  ** *$ **   *  * ** $   *    ***  *  ** *$*  *  * ***$ **$
KWSFGTTLWE ICYNGEIPLK DKTLIEKERF YESRCRPVTP SCKELADLMT RCMNYDPNQR PFFRAIMRDI   HJAK1

I             350
NSLFTPDYEL LTENDMLPNM RIGALGFSGA FEDRDPTQFE ERHLKFLQQL GKGNFGSVEM CRYDPLQDNT   MJAK2
* *    $  $$  *            *** *   * ** $  *  *  **  **   *****   ***
NKLEEQNPDI VSRKKNQPTE V......... ....DPTHFT KRFLKRIRDL GEGHFGKVEL CRYDPE.DNT   HJAK1

II              III        IV                       V             420
GEVVAVKKLQ H.STEEHLRD FEREIEILKS LQHDNIVKYK GVCYSAGRRN LRLIMEYLPY GSLRDYLQKH   MJAK2
** **** *   *  *$ *  $*****$  * *$******  *$*   *  $$****$** ***$$** *
GEQVAVKSLK PESGGNHIAD LKKEIEILRN LYHENIVKYK GICTEDGGNG IKLIMEFLPS GSLKEYLPKN   HJAK1

VI           VII                  490
KERIDHKKLL QYTSQICKGM EYLGTKRYIH RDLATRNILV ENENRVKIGD FGLTKVLPQD KEYYKVKEPG   MJAK2
* $*  *  *  *  ****** $***$$ *$* ****  **$**  * *  ***** *****$$  * ****  **$
KNKINLKQQL KYAVQICKGM DYLGSRQYVH RDLAARNVLV ESEHQVKIGD FGLTKAIETD KEYYTVKDDR   HJAK1

VIII             IX                                                 560
ESPIFWYAPE SLTESKFSVA SDVWSFGVVL YELFTYIEKS KSPPVEFMRM IGNDKQGQMI VFHLIELLKS   MJAK2
$**$******  *  *** $* ******** *  ** ** $  ** $ * $* **   ***   * *$    **
DSPVFWYAPE CLMQSKFYIA SDVWSFGVTL HELLTYCDSD SSPMALFLKM IGPTH.GQMT VTRLVNTLKE   HJAK1

X                 XI       600
NGRLPRPEGC PDEIYVIMTE CWNNNVSQRP SFRDLSFGWI KSGTV       MJAK2
***  *   * ***$*  $*  **    * *  ** *   *
GKRLPCPPNC PDEVYQLMRK CWEFQPSNRT SFQNLIEGFE ALLK        HJAK1
```

FIG. 8A

```
CTG CTT GAT GAC TTT GTC ATG TCT TAC CTT TCC CCT CAG TGG CGG        45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA        90
His Asp Phe Val His Gly Trp Ile Lys Val Pro Val Thr His Glu
                20                  25                  30

ACT CAG GAA GAG TGT CTT GGG ATG GCG GTG TTA GAC ATG ATG AGA       135
Thr Gln Glu Glu Cys Leu Gly Met Ala Val Leu Asp Met Met Arg
                35                  40                  45

ATA GCT AAG GAG AAA GAC CAG ACT CCA CTG GCT GTC TAT AAC TCT       180
Ile Ala Lys Glu Lys Asp Gln Thr Pro Leu Ala Val Tyr Asn Ser
                50                  55                  60

GTC AGC TAC AAG ACA TTC TTA CCA AAG TGC GTT CGA GCG AAG ATC       225
Val Ser Tyr Lys Thr Phe Leu Pro Lys Cys Val Arg Ala Lys Ile
                65                  70                  75

CAA GAC TAT CAC ATT TTA ACC CGG AAG CGA ATC AGG TAC AGA TTT       270
Gln Asp Tyr His Ile Leu Thr Arg Lys Arg Ile Arg Tyr Arg Phe
                80                  85                  90

CGC AGA TTC ATT CAG CAA TTC AGT CAA TGT AAA GCC ACT GCC AGG       315
Arg Arg Phe Ile Gln Gln Phe Ser Gln Cys Lys Ala Thr Ala Arg
                95                 100                 105

AAC CTA AAA CTT AAG TAT CTT ATA AAC CTG GAA ACC CTG CAG TCT       360
Asn Leu Lys Leu Lys Tyr Leu Ile Asn Leu Glu Thr Leu Gln Ser
               110                 115                 120

GCC TTC TAC ACA GAA CAG TTT GAA GTA AAA GAA TCT GCA AGA GGT       405
Ala Phe Tyr Thr Glu Gln Phe Glu Val Lys Glu Ser Ala Arg Gly
               125                 130                 135

CCT TCA GGT GAG GAG ATT TTT GCA ACC ATT ATA ATA ACT GGA AAC       450
Pro Ser Gly Glu Glu Ile Phe Ala Thr Ile Ile Ile Thr Gly Asn
               140                 145                 150

GGT GGA ATT CAG TGG TCA AGA GGG AAA CAT AAG GAA AGT GAG ACA       495
Gly Gly Ile Gln Trp Ser Arg Gly Lys His Lys Glu Ser Glu Thr
               155                 160                 165
```

FIG. 8B

```
CTG ACA GAA CAG GAC GTA CAG TTA TAT TGT GAT TTC CCT GAT ATT      540
Leu Thr Glu Gln Asp Val Gln Leu Tyr Cys Asp Phe Pro Asp Ile
            170                 175                 180

ATT GAT GTC AGT ATT AAG CAA GCA AAT CAG GAA TGC TCA ACT GAA      585
Ile Asp Val Ser Ile Lys Gln Ala Asn Gln Glu Cys Ser Thr Glu
            185                 190                 195

AGT AGA GTT GTG ACC GTC CAC AAG CAG GAC GGG AAG GTC TTG GAA      630
Ser Arg Val Val Thr Val His Lys Gln Asp Gly Lys Val Leu Glu
            200                 205                 210

ATA GAA CTT AGC TCA TTA AAA GAA GCC TTG TCA TTC GTG TCA TTA      675
Ile Glu Leu Ser Ser Leu Lys Glu Ala Leu Ser Phe Val Ser Leu
            215                 220                 225

ATT GAC GGG TAT TAC AGA CTA ACT GCG GAT GCA CAC CAT TAC CTC      720
Ile Asp Gly Tyr Tyr Arg Leu Thr Ala Asp Ala His His Tyr Leu
            230                 235                 240

TGC AAA GAG GTG GCT CCC CCA GCT GTG TTC GAG AAC ATA CAC AGC      765
Cys Lys Glu Val Ala Pro Pro Ala Val Phe Glu Asn Ile His Ser
            245                 250                 255

AAC TGC CAC GGC CCA ATT TCA ATG GAT TTT GCC ATC AGC AAA CTA      810
Asn Cys His Gly Pro Ile Ser Met Asp Phe Ala Ile Ser Lys Leu
            260                 265                 270

AAG AAG GCA GGA AAC CAG ACT GGA CTG TAT GTA CTT CGA TGT AGC      855
Lys Lys Ala Gly Asn Gln Thr Gly Leu Tyr Val Leu Arg Cys Ser
            275                 280                 285

CCT AAG GAC TTC AAC AAA TAC TTC CTG ACC TTT GCC GTT GAG CGA      900
Pro Lys Asp Phe Asn Lys Tyr Phe Leu Thr Phe Ala Val Glu Arg
            290                 295                 300

GAA AAT GTT ATT GAA TAT AAA CAC TGT TTG ATT ACA AAG AAT GAG      945
Glu Asn Val Ile Glu Tyr Lys His Cys Leu Ile Thr Lys Asn Glu
            305                 310                 315
```

FIG. 8C

```
AAT GGA GAG TAC AAC CTC AGT GGG ACT AAG AGG AAC TTC AGT AGT        990
Asn Gly Glu Tyr Asn Leu Ser Gly Thr Lys Arg Asn Phe Ser Ser
                320                 325                 330

CTT AAG GAC CTT TTG AAT TGC TAC CAG ATG GAA ACT GTG CGC TCA       1035
Leu Lys Asp Leu Leu Asn Cys Tyr Gln Met Glu Thr Val Arg Ser
                335                 340                 345

GAC AGT ATC ATC TTC CAG TTC ACC AAA TGC TGT CCT CCA AAG CCG       1080
Asp Ser Ile Ile Phe Gln Phe Thr Lys Cys Cys Pro Pro Lys Pro
                350                 355                 360

AAA GAT AAA TCA AAC CTT CTT GTC TTC AGA ACA AAT GGT GTT TCT       1125
Lys Asp Lys Ser Asn Leu Leu Val Phe Arg Thr Asn Gly Val Ser
                365                 370                 375

GAT GTT CAG CTC TCA CCA ACA TTA CAG AGG CAT AAT AAT GTG AAT       1170
Asp Val Gln Leu Ser Pro Thr Leu Gln Arg His Asn Asn Val Asn
                380                 385                 390

CAA ATG GTG TTT CAC AAA ATC AGG AAT GAA GAT TTG ATA TTT AAT       1215
Gln Met Val Phe His Lys Ile Arg Asn Glu Asp Leu Ile Phe Asn
                395                 400                 405
                 Iₐ
GAA AGC CTT GGC CAA GGC ACT TTT ACA AAA ATA TTT AAA GGT GTA       1260
Glu Ser Leu Gly Gln Gly Thr Phe Thr Lys Ile Phe Lys Gly Val
                410                 415                 420

AGA AGA GAA GTT GGA GAT TAT GGT CAG CTG CAC GAA ACC GAA GTT       1305
Arg Arg Glu Val Gly Asp Tyr Gly Gln Leu His Glu Thr Glu Val
                425                 430                 435
 IIₐ
CTT TTG AAA GTC CTA GAT AAA GCA CAT AGA AAC TAT TCA GAG TCT       1350
Leu Leu Lys Val Leu Asp Lys Ala His Arg Asn Tyr Ser Glu Ser
                440                 445                 450
   IIIₐ
TTC TTT GAA GCA GCA AGC ATG ATG AGT CAG CTT TCT CAC AAG CAT       1395
Phe Phe Glu Ala Ala Ser Met Met Ser Gln Leu Ser His Lys His
                455                 460                 465
```

FIG. 8D

```
IVa
TTG GTT TTG AAT TAT GGA GTA TGT GTC TGT GGA GAG GAG AAC ATT         1440
Leu Val Leu Asn Tyr Gly Val Cys Val Cys Gly Glu Glu Asn Ile
                470                 475                 480

TTG GTT CAA GAG TTT GTA AAA TTT GGA TCA CTG GAT ACA TAC CTG         1485
Leu Val Gln Glu Phe Val Lys Phe Gly Ser Leu Asp Thr Tyr Leu
                485                 490                 495

AAG AAG AAC AAA AAT TCT ATA AAT ATA TTA TGG AAA CTT GGA GTG         1530
Lys Lys Asn Lys Asn Ser Ile Asn Ile Leu Trp Lys Leu Gly Val
                500                 505                 510

GCG AAG CAG TTG GCA TGG GCC ATG CAC TTC CTC GAA GAA AAA TCC         1575
Ala Lys Gln Leu Ala Trp Ala Met His Phe Leu Glu Glu Lys Ser
                515                 520                 525
                    VIa
CTT ATT CAT GGG AAT GTG TGT GCT AAA AAT ATC CTG CTT ATC AGA         1620
Leu Ile His Gly Asn Val Cys Ala Lys Asn Ile Leu Leu Ile Arg
                530                 535                 540

GAA GAA GAC AGG AGA ACG GGG AAC CCA CCT TTC ATC AAA CTT AGT         1665
Glu Glu Asp Arg Arg Thr Gly Asn Pro Pro Phe Ile Lys Leu Ser
                545                 550                 555
    VIIa
GAT CCT GGC ATT AGC ATT ACA GTT CTA CCG AAG GAC ATT TCT TCC         1710
Asp Pro Gly Ile Ser Ile Thr Val Leu Pro Lys Asp Ile Ser Ser
                560                 565                 570
                                                VIIIa
TGT TGT TTC CAA GTT CTT CAG GAG AGA ATA CCA TGG GTA CCA CCT         1755
Cys Cys Phe Gln Val Leu Gln Glu Arg Ile Pro Trp Val Pro Pro
                575                 580                 585

GAG TGC ATT GAG AAT CCT AAA AAT CTA ACT CTG GCA ACA GAC AAG         1800
Glu Cys Ile Glu Asn Pro Lys Asn Leu Thr Leu Ala Thr Asp Lys
                590                 595                 600
        IXa
TGG AGC TTC GGG ACC ACT CTG TGG GAG ATC TGC AGT GGA GGA GAT         1845
Trp Ser Phe Gly Thr Thr Leu Trp Glu Ile Cys Ser Gly Gly Asp
                605                 610                 615
```

FIG. 8E

```
AAG CCC CTG AGT GCT CTG GAT TCT CAA AGA AAG CTG CAG TTC TAT      1890
Lys Pro Leu Ser Ala Leu Asp Ser Gln Arg Lys Leu Gln Phe Tyr
            620                 625                 630
             Xa
GAA GAT AAG CAT CAG CTT CCT GCA CCC AAG TGG ACA GAG TTG GCA      1935
Glu Asp Lys His Gln Leu Pro Ala Pro Lys Trp Thr Glu Leu Ala
            635                 640                 645
                                 XIa
AAC CTT ATA AAT AAT TGC ATG GAC TAT GAG CCA GAT TTC AGG CCT      1980
Asn Leu Ile Asn Asn Cys Met Asp Tyr Glu Pro Asp Phe Arg Pro
            650                 655                 660

GCT TTC AGA GCT GTC ATC CGT GAT CTT AAC AGC CTG TTT ACT CCA      2025
Ala Phe Arg Ala Val Ile Arg Asp Leu Asn Ser Leu Phe Thr Pro
            665                 670                 675

GAT TAT GAA CTA CTA ACA GAA AAT GAC ATG CTA CCA AAC ATG AGA      2070
Asp Tyr Glu Leu Leu Thr Glu Asn Asp Met Leu Pro Asn Met Arg
            680                 685                 690

ATA GGT GCC CTA GGG TTT TCT GGT GCT TTT GAA GAC AGG GAC CCT      2115
Ile Gly Ala Leu Gly Phe Ser Gly Ala Phe Glu Asp Arg Asp Pro
            695                 700                 705

ACA CAG TTT GAA GAG AGA CAC TTG AAG TTT CTA CAG CAG CTT GGC      2160
Thr Gln Phe Glu Glu Arg His Leu Lys Phe Leu Gln Gln Leu Gly
            710                 715                 720
 I
AAA GGT AAC TTC GGG AGT GTG GAG ATG TGC CGC TAT GAC CCG CTG      2205
Lys Gly Asn Phe Gly Ser Val Glu Met Cys Arg Tyr Asp Pro Leu
            725                 730                 735
                                 II
CAG GAC AAC ACT GGC GAG GTG GTC GCT GTG AAG AAA CTC CAG CAC      2250
Gln Asp Asn Thr Gly Glu Val Val Ala Val Lys Lys Leu Gln His
            740                 745                 750
                                     III
AGC ACT GAA GAG CAC CTC CGA GAC TTT GAG AGG GAG ATC GAG ATC      2295
Ser Thr Glu Glu His Leu Arg Asp Phe Glu Arg Glu Ile Glu Ile
            755                 760                 765
                     IV
CTG AAA TCC TTG CAG CAT GAC AAC ATC GTC AAG TAC AAG GGA GTG      2340
Leu Lys Ser Leu Gln His Asp Asn Ile Val Lys Tyr Lys Gly Val
            770                 775                 780
```

FIG. 8F

```
TGC TAC AGT GCG GGT CGG CGC AAC CTA AGA TTA ATT ATG GAA TAT       2385
Cys Tyr Ser Ala Gly Arg Arg Asn Leu Arg Leu Ile Met Glu Tyr
            785                 790                 795
        V
TTA CCA TAT GGA AGT TTA CGA GAC TAT CTC CAA AAA CAT AAA GAA       2430
Leu Pro Tyr Gly Ser Leu Arg Asp Tyr Leu Gln Lys His Lys Glu
            800                 805                 810

CGG ATA GAT CAC AAA AAA CTT CTT CAA TAC ACA TCT CAG ATA TGC       2475
Arg Ile Asp His Lys Lys Leu Leu Gln Tyr Thr Ser Gln Ile Cys
            815                 820                 825

AAG GGC ATG GAA TAT CTT GGT ACA AAA AGG TAT ATC CAC AGG GAC       2520
Lys Gly Met Glu Tyr Leu Gly Thr Lys Arg Tyr Ile His Arg Asp
            830                 835                 840
VI
CTG GCA ACA AGG AAC ATA TTG GTG GAA AAT GAG AAC AGG GTT AAA       2565
Leu Ala Thr Arg Asn Ile Leu Val Glu Asn Glu Asn Arg Val Lys
            845                 850                 855
        VII
ATA GGA GAC TTC GGA TTA ACC AAA GTC TTG CCG CAG GAC AAA GAA       2610
Ile Gly Asp Phe Gly Leu Thr Lys Val Leu Pro Gln Asp Lys Glu
            860                 865                 870

TAC TAC AAA GTA AAG GAG CCA GGG GAA AGC CCC ATA TTC TGG TAC       2655
Tyr Tyr Lys Val Lys Glu Pro Gly Glu Ser Pro Ile Phe Trp Tyr
            875                 880                 885
VIII
GCA CCT GAA TCC TTG ACG GAG AGC AAG TTT TCT GTG GCC TCA GAT       2700
Ala Pro Glu Ser Leu Thr Glu Ser Lys Phe Ser Val Ala Ser Asp
            890                 895                 900
        IX
GTG TGG AGC TTT GGA GTG GTT CTA TAC GAA CTT TTC ACA TAC ATC       2745
Val Trp Ser Phe Gly Val Val Leu Tyr Glu Leu Phe Thr Tyr Ile
            905                 910                 915

GAG AAG AGT AAA AGT CCA CCC GTG GAA TTT ATG CGA ATG ATT GGC       2790
Glu Lys Ser Lys Ser Pro Pro Val Glu Phe Met Arg Met Ile Gly
            920                 925                 930

AAT GAT AAA CAA GGG CAA ATG ATT GTG TTC CAT TTG ATA GAG CTA       2835
Asn Asp Lys Gln Gly Gln Met Ile Val Phe His Leu Ile Glu Leu
            935                 940                 945
```

FIG. 8G

```
                          X
CTG AAG AGC AAC GGA AGA TTG CCA AGG CCA GAA GGA TGC CCA GAT        2880
Leu Lys Ser Asn Gly Arg Leu Pro Arg Pro Glu Gly Cys Pro Asp
                    950             955                 960

GAG ATT TAT GTG ATC ATG ACA GAG TGC TGG AAC AAC AAT GTG AGC        2925
Glu Ile Tyr Val Ile Met Thr Glu Cys Trp Asn Asn Asn Val Ser
                    965             970                 975
        XI
CAG CGT CCC TCC TTC AGG GAC CTT TCC TTC GGG TGG ATC AAA TCC        2970
Gln Arg Pro Ser Phe Arg Asp Leu Ser Phe Gly Trp Ile Lys Ser
                    980             985                 990

GGG ACA GTA TAGCTGCGTG AAAGAGATGG CCTTACTCAG AGACCAAGCA            3019
Gly Thr Val

GACTTCCAGA ACCAGAACAA AGCTCTGTAG CCTTGTGTCT ACACATCCTT             3069

ATCATGACGC TAGCTAGGCA GAAAGAAAAC TGTGACGCCG TCTGCTCAAA             3119

AGCTTTGGAA AACGCCGTGC AGGTTTGTTT CATCACCATC TGTAAAAACC             3169

ACTGCTCAAG TCTGGCAGCA TGCTTGTGGG CTGATGCATG GAGCTCACCA             3219

CAGAGTCTCT GCATCTCCTC TGACAGAAGA AGAAAAATAG ACAATTTTCA             3269

ACTCACTTTT TTGAGAAATG GAAAAAATT ATAATGTAAA TTTTTCAGTG              3319

TAGGAAATAC ACAGAACATA CATGTACAGT TTTTACCACG TGGAGTGTAT             3369

AATACTTTGG CCTCTTGTGT GATTTACATG AGGGCTGATG TTTGTTAATG             3419

TTTTCTAATT TTTCCATAGG TGATCTATAA TAACTTCATG ATACAAATTA             3469

AAATGCTCAG AAAATTAAAA AAAAA                                        3495
```

FIG. 11A

```
      1           11          21          31          41          51          61          71          81          91
J1    MQYLNIKEDCNAMAFCAKMRSSKKTEVNLEAPEPGVEVIFYLSDREPLRLGSGEYTAEELCIRAAQACRISPLCHNLFALYDENTKLWYAPNRTITVDDK
J2                                                                    AEEVCIHIAHKVGITPPCFNLFALFDAQAQVWLPPNHILEIPRD
T2    MPLRHWGMARGSKPVGDGAQPMAAMGGLKVLLHWAGPGGGEPWVTFSESSLI....AEE-CI---------P-C-NLFAL-------W--PN---------

101         111         121         131         141         151         161         171         181         191
J1    MSLRLHYRMRFYFTNWHGTNDNEQSVWRHSPKKQKNGYEKKKIPDATPLLDASSLEYLFAQGQYDLVKCLAPIRDPK.TEQDGHDIENECLGMAVLAISHY
J2                                                 LLDDFVMSYLSPQWRHDFVHGWIKVPVTHETQEE......CLGMAVLDMRI
T2    ASLMLYFRIRFYFRNWHGMNPREPAGYRCGPPGTEASSDQTAQGMQ..LLDPASFEYLFEQGKHEFENDVASLWELS.TEEEIHHFKNESLGMAFLHLCHL
      -SL-L-R-RFYF-NWHG--N--E----R--P-------------------LLD--S-EYLF-QG-HDFV---A-----TEEE-H---NECLGMAVL---H-
                                                    JH6→

201         211         221         231         241         251         261         271         281         291
J1    AMMKKMQLPELPKDISYKRYIPETLNKSIRQRNLLTRMRINNVFKDFLKEFNNKTICDSSVSTHDLKVKYLATLETLTKHYGAEIFETSMLLISSENEMN
J2    AKEKDQTPLAVYNSVSYKTFLPKCVRAKIQDYHILTRKRIRYRFRRFIQQFSQCKATARN....LKLKYLINLETLQSAFYTEQFEVKESARGPSGEEI
T2    ALRHGIPLEEVAKKTSFKDCIPRSFRRHIRQHSALTRLRLRNVFRRFRRFLRDFQPGRLSQQM......VMVKYLATLERLAPRFGTERVPVCHLRLLAQAEGE
      A--K---L-EV-K---SYK---IP----R--IRQ-----LTR--RIRNVFRRFL----F--------LKVKYLATLETL---FGTE-FEV--L------E---

301         311         321         331         341         351         361         371         381         391
J1    WFHSNDGGNVLYY.........EVMVTGNLGIQWRHKPNVVSVEKEKNKLKRKKLENKDKKDEEKNK.......IREEWNNFSFFPEITHIVIKESV
J2    FAT............IIITGNGGIQWSRGKHKESETLTEQDLQLYCDFP..........DIIDVSIKQANQECSTESRI
T2    PSYIRDSGVAPTDPGPESAAGPPTHEVLVTGTGIQWMPVEEEVNKEEGSSGSSARNPQASLFGKKAKAHKAFGQPADRPREPLWAYFCDITHVLKEHC
      -----D-G-------       EV--VTGNGGIQW------VS-E--------L--------K----       -R-----S-F---ITH-V--KE--
                            JH5→                                                                         JH6→

401         411         421         431         441         451         461         471         481         491
J1    VSINKQDNKKMELKLSSHEEALSFVSLVDGYFRLTADAHHYLCTDVAPPLIVHNIQNGCHGPIC-EYAI.NKLRQEGSEEGMYVLRWSCTDFDNILMTVT
J2    VTVHKQDGEVLEIELSSLKEALSFVSLIDGYYRLTADAHHYLCKEVAPPAVLENIHSNCHGPISMDFAI.SKLKKAGNQTGLYVLRCSPKDFNKYFLTFA
T2    VSIHRQDNKCLELSLPSRAAALSFESLVDGYFRLTADSSHYLCHEVAPPRLVMSIRDGIHGPLLEPFVQQAKLRP..LEDGLYLIHWSTSHPYRLILTVA
      VSIHKQDNK-LEL-LSS--EALSFVSLVDGYFRLTADAHHYLC--EVAPP---V-NI--GCHGPI----FAI--KLR--G--E-GLYVLRWS----DF----LTVA
                                                                      JH4→                                  JH4→
```

FIG. 11B

```
     501       511       521       531       541       551       561       571       581       591
J1  CFEKSEQVQGAQKQFKNFQIEVQKGRYSLHGSDRSFPSLGDLMSHLKKQILRTDNISFMLKRCCQPKPREISNLLVATKKAQEWQPVYPMSQLSFDRILK
J2  VER....ENVIEYKHCLITKNENGEYNLSGTKRNFSSLKDLLNCYQMETVRSDSIIFQFTKCCPPKPKDKSMLLVFRTNGVSDVQLSPTLQRHNNVNQM
T2  QRSQAPDGMQSLRLRKF.PIEQQDGAFVLEGWGRSFPSVRELGAALQGCLLRAGDDCFSLRRCCLPQPGETSNLIIMRGARASPRTL.NLSQLSFHRVDQ
    -----------------K---IE-Q-G-Y-L-G--RSFPSL-DL---LQ--LR-D-I-F-L-RCC-PKP-E-SNLLV-R----S---L-P-SQLSF-R---
                           ├─JH3─┤
     601       611       621       631       641       651       661       671       681       691
J1  KD]...LVQGEHLGRGTRTHIYSGTLMDYKDDEGTSEEKK..........                  IKVILKVLDPSHRDISLAFFEAASMMRQVSHKHIVYLYGVC
J2  VFHKIRNEDLIFNESLGQGTFTKIFKGVRREVGDY.GQLHETE.                       VLLKVLDKAHRNYSESFFEAASMMSQLSHKHLVLNYGVC
T2  KE[...ITQLSHLGQGTRTNVYEGRLRVEGS..GDPEEGKMDDEDPLVPGRDGQELRVLKVLDPSHHDIALAFYETASLMSQVSHTHLAFVHGVC
    K-   L-Q-EHLGQGTRT-IY-G-LR--GD- G--EE-K                            --V-LKVLDPSHRDISLAFFEAASMMSQVSHKHLV--YGVC
        └─JH2
     701       711       721       731       741       751       761       771       781       791
J1  VRDVENIMVEEFVEGGPLDLFMHRKSDVLTTPWKFKVAKQLASASALSYLEDKDLVHGNVCTKNLLAREGIDSECGPFIKLSDPGIPITVLSRQECIERIP
J2  VCGEENILVQEFVKFGSLDTYLKKNSINILWKLGVAKQLAWAMHFLEEKSLIHGNVCAKNILLIREEDRRTGNPFIKLSDPGISITVLPKDISSCCF.
T2  VRGPENSMVTEYVEHGPLDVWLRRERGHVPMAWKMVVAQQLASALSYLENKNLVHGNVCGRNILLARLGLAEGTSPFIKLSDPGCGLGALSREERVERIP
    VRG-ENIMV-EFVE-GPLD--L-R-------WK--VAKQLASALSYLE-K-LVHGNVC-KNILLAREG------PFIKLSDPGI-ITVLSR-E--ERIP
     801       811       821       831       841       851       861       871       881       891
J1  WIAPECVED.SKNLSVAADKWSFGTTLWEICYNGEIPLKDKTLIEKERFYESRCRPVTPSCKELADLMTRCMNYDPNQRPFFRAIMRDINKLE
J2  QVLQERIPWVPPECIEN.PKNLTLATDKWSFGTTLWEICSGGDKPLSALDSQRKLQFYEDKHQLPAPKWTELANLINNCMDYEPDFRPAFRAVIRDLNSLF
T2  WLAPECLPGGANSLSTAMDKWGFGATLLEICFDGEAPLQSRSPSEKEHFYQRQHRLPEPSCPQLATLTSQCLTYEPTQRPSFATILRDLTAVQ
    W-APEC-E----NNLS-A--DKWSFGTTLWEIC--GE--PL------EKE-FYE--HRLP-PSC-ELA-L---CM-YEP-QRP-FRAI-RDLN-L-
```

FIG. 11C

```
     901         911         921         931         941         951         961         971         981         991
J1   EQNPDIVSRKKNQP........................TEVDPTHF.KRFLKRIRDLGEGHFGKVELCRYDP.EDNTGEQVAVKSLKPESGGNHIADLKKEIEILRNLYHE
J2   TPDYELLTENDMLPNMRIGALGFSGAFEDRDPTQFEERHLKFLQQLGKGNFGSVEMCRYDPLQDNTGEVVAVKLQH.STEEHLRDFEREIEILKSLQHD
T2   PHNLADVLTVNRDS.......................PAVGPTTFHKRVYLKKIRDLGEGHFGKVSLYCYDPTNDGTGEMVAVKALKADCGPQHRSGWKQEIDILRTLYHE
     --N---V-----P-----------------------VDPT-F-KR--LK-IRDLGEGHFGKVELCRYDP--DNTGE-VAVK-LK--SG--H--D-K-EIEILR-LYHE
                                        ┌──JH2
    1001        1011        1021        1031        1041        1051        1061        1071        1081        1091
J1   NIVKYKGICTEDGGNGIKLIMEFLPSGSLKEYLPKNKNKINLKQQLKYAVQICKGMDYLGSRQYVHRDLAARNVLVESEHQVKIGDFGLTKAIETDKEYY
J2   NIVKYKGVCYSAGRRNLRLIMEYLPYGSLRDYLQKHKKERIDHKKLLQYTSQICKGMEYLGTKRYIHRDLATRNILVENENRVKIGDFGLTKVLPQDKEYY
T2   HIIKYKGCC.EDQGE.KSLVMEYVPLGSLRDYLPRHS..IGLAQLLLFAQQICEGMAYLHAHDYIHRDLAARNVLLDNDRLVKIGDFGLAKAVPEGHEYY
     NIVKYKG-C--EDGG----LIMEYLP-GSLRDYLPKHK---I-LKQLL-YA-QICKGM-YLG---YIHRDLAAARNVLVENE--VKIGDFGLTKA-P-DKEYY 1101        1111        1121        1131        1141        1151        1161        1171        1181        1191
J1   TVKDDRDSPVFWYAPECLMQSKFYIASDVWSFGVTLHELLTYCDSDSSPMALFLKMIG.PTHGQMTVTRLVNTLKEGKRLPCPPNCPDEVYQLMRKCWEF
J2   KVKEPGESPIFWYAPESLTESKFSVASDVWSFGVVLYELFTYIEKSKSPPVEFMRMIGNDKQGQMIVFHLIELLKSNGRLPRPEGCPDEIYVIMTECWNN
T2   RVREDGDSPVFWYAPECLKEYNFYYASDVWSFGVTLYELLTHCDSSQSPPTKFLELIG.IAQGQMTVLRLTELLEAGERLPRPDKCPCEVYHLMKNCWET
     -VKEDGDSPVFWYAPECL-ESKFY-ASDVWSFGVTLYELLTYCDSS-SPP--FL-MIG---QGQMTV-RL-ELLK-G-RLPRP--CPDEVY-LM--CWE- 1201        1211        1221        1231
J1   NVSQRPSFRDLSFGWIKSGTV*
J2   QPSNRTSFQNLIEGFEALLK*
T2   EASFRPTFENSIPILKTVHEKYQGQAPSVSSVC*
     ---S-RPSF-NLI-G-┘
              └──JH1
```

FIG. 12

```
JAK1   QNGCHGPIC-EYAI.NKLROEGSEGMYVLRWSCT...DFDNILMTVTCFEKSEQVQGAQKQFKNFQIEVQKGRYSLHGSDRSFPSLGDLMSHLKKQILRTDNISFMLKRCCQPKP
JAK2   HSNCHGPISMDFAI.SKLKKAGNQTGLYVLRCSPK...DFNKYFLTFAVER..ENVIEYKHCLITKNENGEYNLSGTKRNFSSLKDLLNCYQMETVRSDSIIFQFTKCCPPKP
TYK2   RDGIHGPLLEPFVQQAKLRP.LEDGLYLIHWSTS...HPYRLIITVAQRSQAPDGMQSLRLRKF.PIEQQDGAFVLEGWGRSFPSVRELGAALQGCLLRAGDDCFSLRRCCLPQP
       -GCHGPI----FAI--KLR--G-E-GLYLRWS-------DF-----LTVA------K---IE-Q--G-Y-L-G--RSFPSL-DL----LQ----LR-D-I-F-L-RCC--PKP
                                                                          |      |  |  |
GAP-N  WYHGKI----A----L-----GSYLIRES---PGDFVLS-----------R---------Y---G--R-F-SL-DL--YY---------L-EPV
GAP-N  WYHGKLDRTIA.EERLR.QAGKSGSYLIRESDRRPGSFVLSFLSQT.NV......VNHFRI..IAMC.GDYY.IGG.RFSSLSDLIGYSHVSCLLKE....KLLYPV
GAP-C  WFHGKISKQEA.YNLLM.TVGQACSFLVRPSDNTPGDYSLYF.RTSENIQ..R....FKI.CPTPN.NQFM.MGG.RYNSIGDIDHYRKEQIVEGYY......LKEPV
v-Crk  WYWGRLSRGDA.VSLLQ..GQRHGTFLVRDSGSIPGDFVLSV.SESSRVS.......HYIVNSLGPAGGRRAGGE.[18].FDSLPSLLEFYKIHYLDTT......TLIEPV
```

PROTEIN TYROSINE KINASE

This application is a divisional of Ser. No. 08/064,067 filed as PCT/US91/08889, Nov. 26, 1991.

The present invention relates generally to a novel protein tyrosine kinase and to genetic sequences encoding same.

Protein tyrosine kinases (PTKs) are structurally well suited to a role intracellular signal transduction. Many growth factor receptors, for example, transduce the extracellular stimulus they receive through interaction with their cognate ligand via an intracellular tyrosine kinase domain. At least one of the non-receptor PTKs, namely LCK, is believed to mediate the transduction in T-cells of a signal from the interaction of a cell-surface protein (CD4) with a cross-linked anti-CD4 antibody.

The broader family of PTKs can be sub-divided on the basis of structural parameters of individual members. For example, the src family of PTKs now numbers 8 members (Marth et al, 1985; Nishizawa et al., 1986; Semba et al, 1986; Martinez et al, 1987; Sukegawa et al, 1987; Yamanishi et al, 1987; Hotzman et al, 1987; Dymecki et al, 1990), each with a characteristic complement of extra-catalytic domains, including an SH2, an SH3 domain and a variable ligand binding domain. It is clear that a process of gene duplication has taken place in this case, so that the evolutionarily successful thematic structure of this family can be employed in a variety of cellular contexts. Similar PTK structural sub-families exist based around the FGF receptor and the CSF-1 receptor (reviewed in Wilks, 1990).

However, one feature in common with the aforementioned PTKs is that each kinase bears a single highly related "catalytic" domain.

In accordance with the present invention a protein tyrosine kinase is provided which is distinct from those previously known. In particular, the protein tyrosine kinase of the present invention is unique since it possesses more than one protein kinase catalytic domain. Furthermore, the kinase does not bear an SH2 domain. The novel protein tyrosine kinase of the present invention represents a new subfamily or class of protein tyrosine kinase.

Accordingly, one aspect of the present invention is directed to an animal protein tyrosine kinase-like molecule comprising a polypeptide having multiple protein kinase catalytic domains but no SH2 domain.

Preferably, the polypeptide has two protein kinase catalytic domains.

Preferably, the animal is a mammal and is most preferably a human or a mouse.

Hereinafter, a protein having these characteristics will be referred to as a "JAK" (from JAnus Kinase: Janus, in Encyclopaedia Britannica (11th Ed) Vol XV pp 155–156). The present invention is specifically exemplified using JAK1 and JAK2 from humans and mice. This is done, however, with the understanding that the present invention extends to the whole family of JAKs from all animals and to mutants, derivatives, analogues and homologues thereof. The term "protein tyrosine kinase-like molecule" (abbreviated herein to "PTK-like molecule") is used throughout the specification and claims to emphasise that the present invention encompasses all members of the JAK family and to their mutants, derivatives, analogues and homologues.

In accordance with the present invention, there is provided a PTK-like molecule. Preferably the molecule is in biological pure or in substantially pure and/or synthetic form. The purity of the preparation is characterised by a sample comprising at least 70% by weight, preferably at least 80% by weight and most preferably at least 90% by weight PTK-like molecule. Alternatively, wherein the purity of the enzyme preparation is not critical, the present invention also encompasses an impure PTK-like molecule preparation but which possesses a substantial amount of JAK activity.

The present invention is directed to a naturally occurring PTK-like molecule, biologically pure or substantially pure as hereinbefore defined and to derivatives, functional analogues and homologues thereof. Such derivatives include polypeptides having single or multiple amino acid substitutions, deletions and/or additions relative to the naturally occurring sequence. These derivatives, functional analogues and homologues also encompass single or multiple substitutions, deletions and/or additions to any associated molecules such as carbohydrate, lipid and/or proteinacious moieties. Reference herein to "PTK-like molecules" includes all such derivatives, functional analogues and homologues. The present invention also extends to synthetic forms of the polypeptides which include recombinant molecules and molecules prepared by the stepwise addition of amino acids to groups of amino acids in defined order.

A range of derivatives and analogues of the PTK-like molecule are contemplated herein and include altering the molecule at its nucleotide sequence-encoding level, during its expression within a cell or in vitro or post-synthesis modification. Such derivatives and analogues include, but are not limited to, modifications to side chains, incorporation of unnatural amino acids during polypeptide synthesis and the use of crosslinkers and other methods which impose conformational constraints on the polypeptide or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6, trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of argine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ringe of a histidine residue may be accomplished by alkylation with iodoacetic acid derivatives or N-carbethosylation with diethylpyrocarbonate.

Examples of incorporating unnatural amino acids and derivatives during polypeptide synthesis include, but are not limited to, use of norleucine, 4-amino butyric acid, 4-amino-3-hydroxy-5-phenlpentanoic acid, 6-aminohexanoic acid, t-butylglycine, norvaline, phenylglycine, ornithine, sarcosine, 4-amino-3-hydroxy-6-methylhelptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, polypeptides could be conformationally constrained by, for example, incorporation of $C_a$ and $N_a$-methylamino acids, introduction of double bonds between $C_a$ and $C_\beta$ atoms of amino acids and the formation of cyclic polypeptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof corresponding to regions of PTK-like molecules. Preferably, the PTK-like molecules will retain JAK activity. However, molecules carrying mutations in the catalytic domains rendering these inactive may be useful in, for example, titrating but activity and generation of antibodies such molecules are encompassed by the present invention.

The molecular weights of the PTK-like molecules of the present invention range from 100,000 to 200,000 daltons and preferably from 120,000 to 150,000 daltons.

In a most preferred embodiment, the present inventions provides JAK1 and JAK2. JAK1 is an approximately 1142 amino acid molecules with a molecular weight of about 132,000 daltons and a nucleotide sequence shown in FIG. 2. JAK2 is an approximately 1,100 amino acid molecule with a molecular weight of about 130,000 daltons and with a nucleotide sequence shown in FIG. 8.

The present invention is also directed to genetic sequences including DNA, cDNA and mRNA which encode the PTK-like molecules hereindescribed. Such genetic sequences include single or multiple nucleotide substitutions, deletions and/or additions relative the naturally occurring sequence and extend to sequences encoding the derivatives, functional analogues and homologues of the PTK-like molecules. The present invention also provides these genetic sequences in vector and expression vector systems either in vitro or in a biological system (i.e. eukaryotic or prokaryotic cells) transformed with such vectors or genetic sequences. In a most preferred embodiment the present invention provides cDNA encoding JAK1 and JAK2 as set forth in FIGS. 2 and 8, respectively. A range of mutants can be obtained using standard techniques such as an oligonucleotide mutagenesis and chemical mutagenesis, and all such mutants and derivatives are encompassed by the present invention.

The present invention also provides antibodies to a PTK-like molecule. Such antibodies may be monoclonal or polyclonal.

The PTK-like molecule of the present invention have varying utility such as in the phosphorylation of proteins, incorporation of labels and in the design of analogues, antagonists and agonists of JAKs.

Accordingly, another aspect of the present invention contemplates a method for phosphorylating a protein comprising contacting said protein with a phosphorylating effective amount of a PTK-like molecule, said molecule comprising a polypeptide having multiple protein kinase catalytic domains but no SH2 domain for a time and under conditions sufficient for said first protein to be phosphorylated. Preferably, the polypeptide has two protein kinase catalytic domains and most preferably is JAK1 and/or JAK2 and/or their derivatives.

The present invention is further described by reference to the following non-limiting Figures and Examples.

Figure 1B:
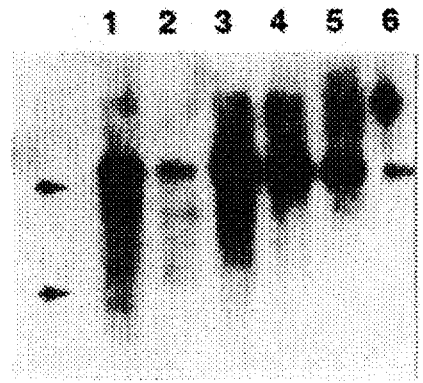

In the Figures:

FIGS. 1(A and B) is a photographic representation of a Northern analysis of murine and human JAK1.

A. 2 µg aliquots of poly(A)+mRNA from urine tissues: lane 1, lung: lane 2, liver: lane 3, kidney: lane 4, intestine: lane 5, brain: lane 6, skeletal muscle: lane 7, spleen: lane 8, salivary gland: lane 9, placenta: lane 10, mammary gland, were fractionated on a 1.0% agarose/formaldehyde (Moran et al. 1988) gel and the RNA transferred onto a Genescreen plus (Dupont) membrane. The transferred RNA was hybridized with a 1.8 kb $^{32}$P-labelled murine JAK1 probe and the filter autoradiographed for 16 hr. at −70° C. with two intensifying screens. The relative mobilities of 28S rRNA (upper arrow) and 18S rRNA (lower arrow) are shown.

B. 2 µg aliquots of poly(A)+mRNA from the human haemopoietic cell lines: lane 1, HL60 (myelo-monocytic); lane 2, U937 (monocytic): lane 3, LK63 (pre-B): lane 4, RAJI (B-cell): lane 5, (CEM (T-cell): lane 6, K562 (erythroleukaemia) were fractionated on a 1.0% agarose/formaldehyde (Moran et al. 1988) gel and the RNA transferred onto a Genescreen plus (Dupont) membrane. The transferred RNA was hybridized with a full-length $^{32}$P-labelled human JAK1 probe and the filter autoradiographed for 16 hr. at −70° C. with two intensifying screens. The relative mobilities of 28S rRNA (upper arrow) and 18S rRNA (lower arrow) are shown.

Figure 3B:
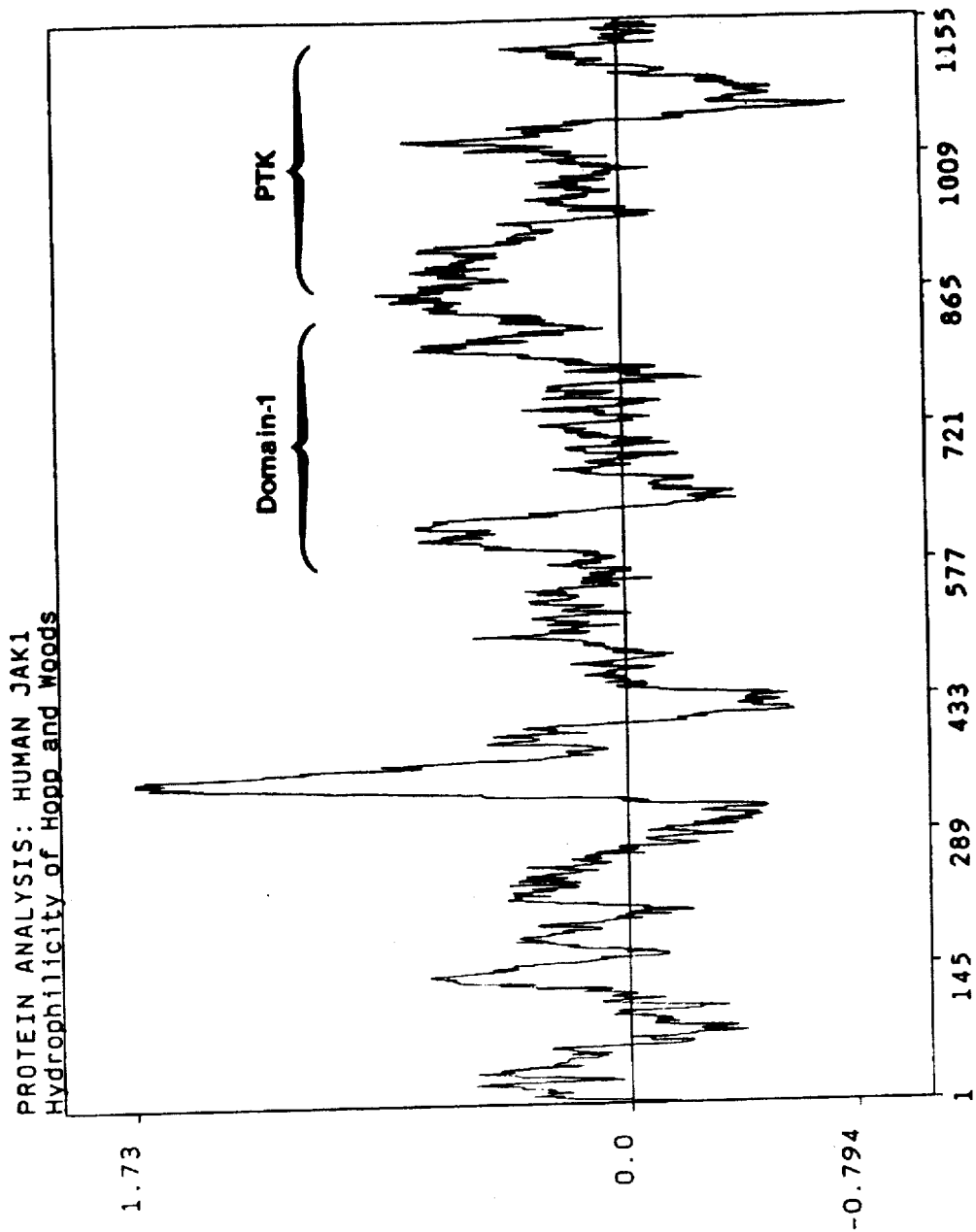

FIGS. 2(A–M) is a representation showing nucleotide sequence and predicted amino acid sequence of human JAK1. The DNA sequence is numbered at the end of each line of sequence from the first nucleotide of the largest clone (pHJ7.3), the amino acid sequence (in one letter code) is numbered from the putative AUG and appears above the line to which it refers. The two kinase catalytic domains are boxed with arrows, and kinase consensus motifs are enumerated according to the nomenclature of Hanks et al (1988). The suffix a (e.g. IIa) denotes the kinase related motifs present in the first kinase-related domain (designated domain-1 in FIG. 3a) also numbered according to the same nomenclature. The tyrosine residue in an analogous position to the autophosphorylation site of a number of other protein tyrosine kinases is marked with an inverted triangle. (SEQ ID NO: 1) contains the DNA sequence and SEQ ID NO: 24 contains the amino acid sequence.

FIGS. 3(A and B) is a representation showing:

Panel 3A. Amino-acid sequence comparison of the two kinase-related domains of JAK1. All JAK1 amino acid sequences refer to amino acids in SEQ ID NO: 24. The amino-acid sequences (expressed in one-letter amino acid code) of the two kinase-related domains (domain-1 amino-acids 576-825; domain-2 (PTK-domain) amino-acids 868-1130) of JAK1 and the human threonine/serine-specific kinase CDC2 (24) (amino acids 9-272) are aligned in order to maximize identity. The kinase-related domains have been divided into three segments and the number of amino acid residues separating each segment appears at the end of each line. Motifs held in common between at least two of these domains are both bolded and boxed. Roman numerals above the alignment correspond to the conserved domain nomenclature devised by Hanks et al (1988).

Panel 3B. Hydropathy plot of the human JAK1 protein. The protein sequence of human JAK1 (including the 10 extra amino acids which precede the most likely initiation codon) were analysed by the hydrophilicity algorithm of Kyte and Doolittle (1982) using a span length of 25 amino acids. The relative locations of the two kinase related domains are marked as Domain-1 and PTK. The absence of a hydrophobic transmembrane domain is clearly seen, as can the presence of a highly hydrophilic region between amino acids 323 and 350.

Figure 4A:
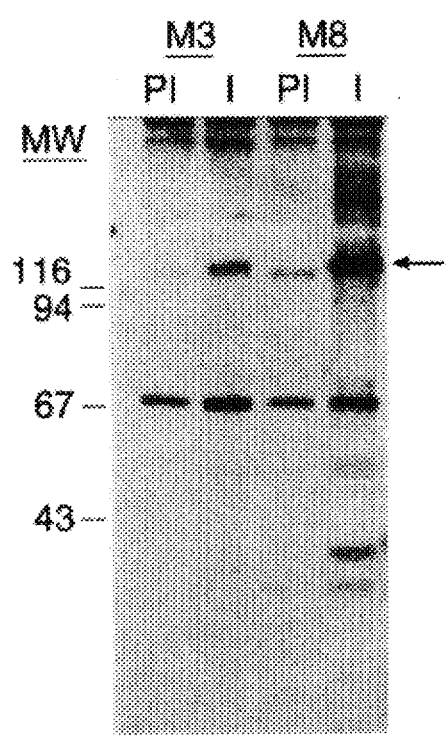
Figure 4B:
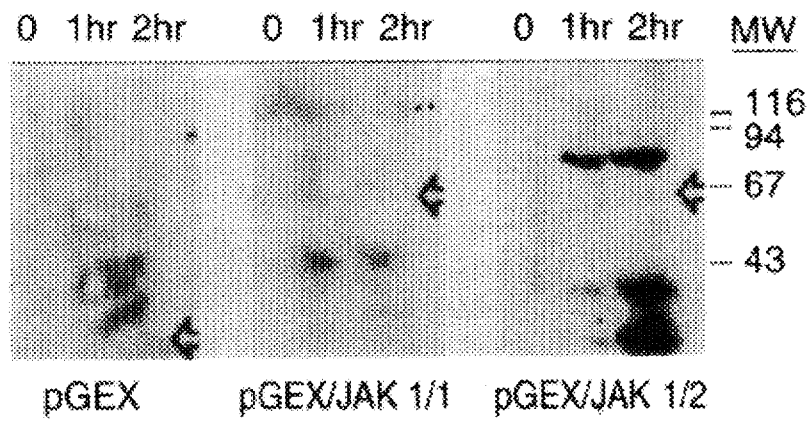
Figure 4C:
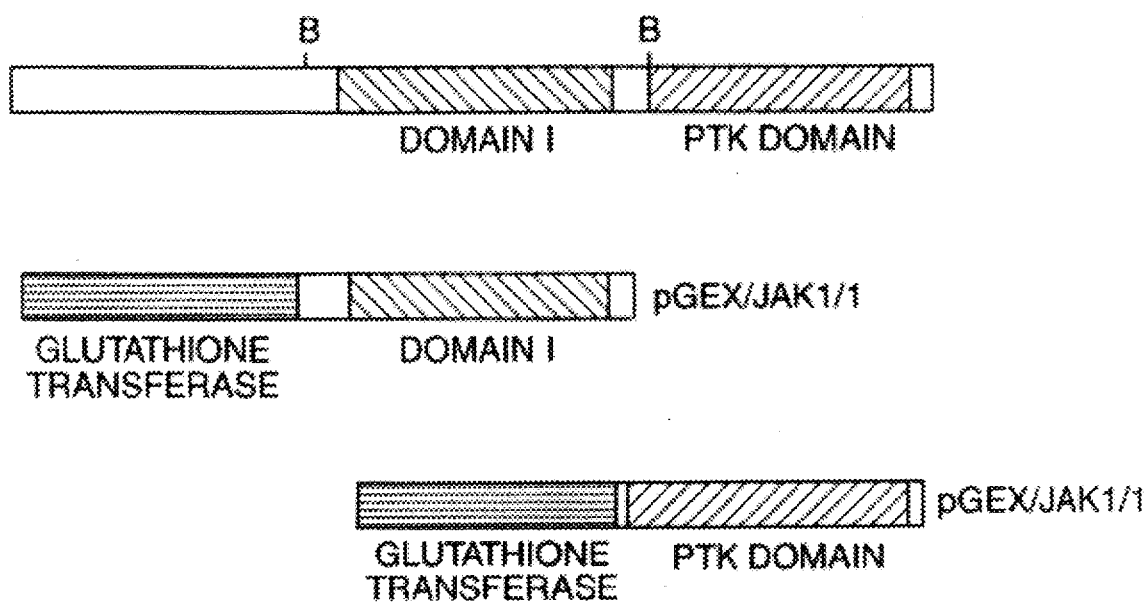

FIGS. 4(A–C) is a representation of an analysis of the JAK1 protein.

Panel 4A. Cellular proteins of the murine mammary fibroblast cell line (17) were labelled with $^{35}$S-methionine (panel A) and immunoprecipitated with either pre-immune (PI) or immune (I) anti-JAK rabbit antiserum (raised in rabbit M8 against the pGEX/JAK1/1 fusion protein or the C-terminal peptide [M3]) and fractionated on a 9.5% SDS-PAGE gel (Laemmli, 1970). Both rabbit antisera specifically immunoprecipitated an $^{35}$S-labelled protein of apparent molecular weight 130,000 D.

Panel 4B. Demonstration of tyrosine kinase activity in JAK1 bacterial fusion proteins. JAK1 fusion proteins were generated using pGEX2 (Smith and Johnson, 1988). The entire domain-1 region was included in construct pGEX/JAK1/1. The PTK domain portion of the fusion protein extended to the BamHI site 15 nucleotides 5' of the first glycine codon of the GXGXXG motif (SEQ ID NO: 3) of the ATP binding site. An empty vector control was also performed. The bacteria were induced by the addition of 1 mM IPTG as described by Smith and Johnson (1988) and two 1 ml aliquots of the bacteria were removed at 60 minutes and 120 minutes post-induction and lysed with SDS sample buffer. Western analysis of the samples was performed using anti-phosphotyrosine antisera (PY-20 [ICN]). The arrow heads mark the positions of the GEX-JAK fusion proteins, in each induction.

Panel 4C. Construction of the pGEX/JAK fusion proteins. The locations of the two kinase related domains of JAK1 are shown, and below, the structure of the fusion proteins with the glutathione S-transferase gene.

FIG. 5 is a representation of a sequence comparison between JAK1 and JAK2 kinase-related domains. All JAK2 amino acid sequences refer to amino acids in SEQ ID NO: 25. The deduced amino acid sequence of murine JAK2 was compared to the human JAK1 amino acid sequence by application of an alignment programme of the Staden VAX-based suite of Sequence analysis programmes. Asterisks (*) denote identity, dollar signs ($) denote conservative substitutions. Sequences are numbered with respect to the JAK1 sequence. The extent of the domain-1 and PTK domains is shown by arrows above the amino acid sequence.

Figure 6:
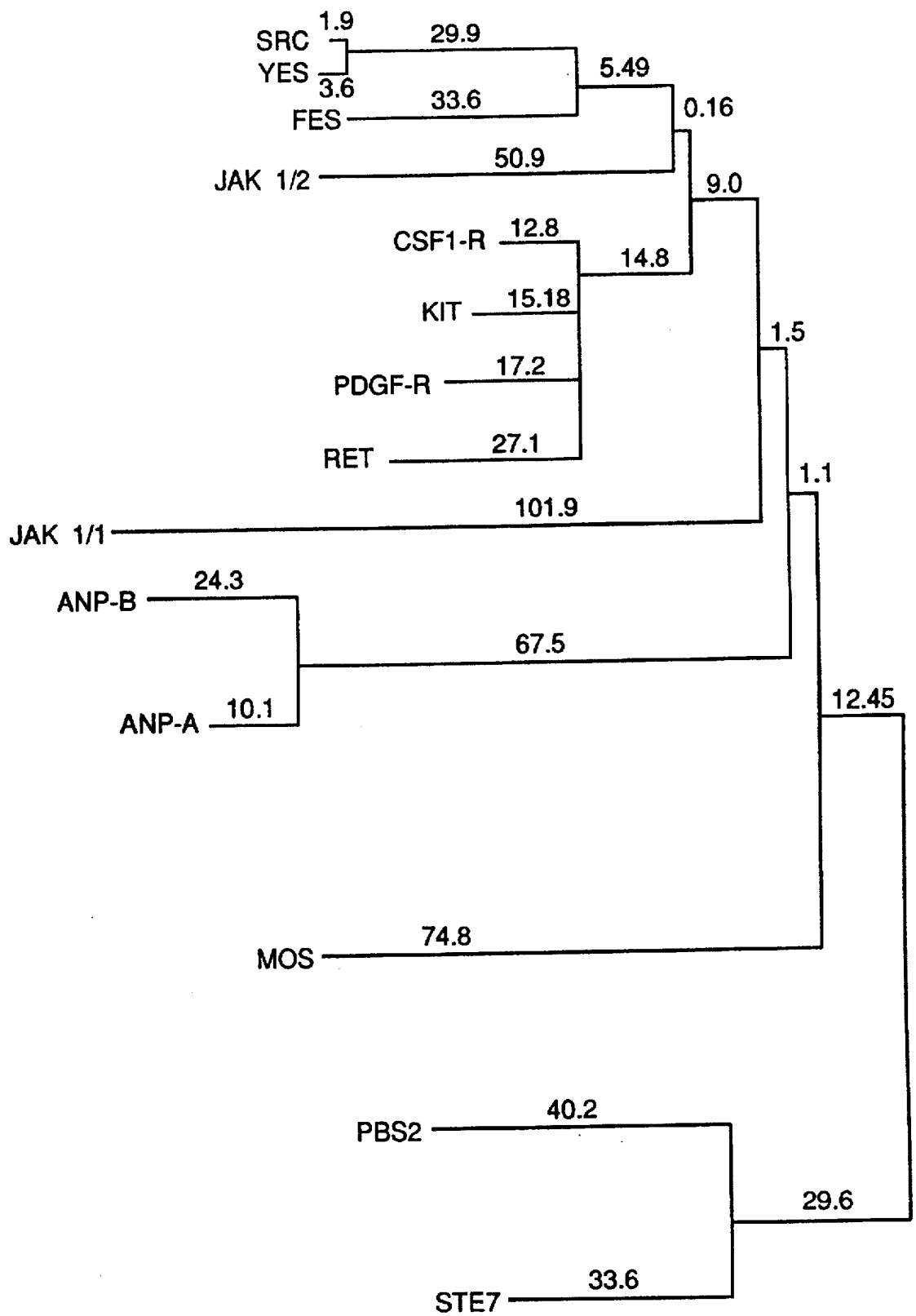

FIG. 6 is a graphical representation of a phylogenetic analysis of the two JAK1 Kinase-like domains. The tree building concept of Fitch and Margoliash (1967) as implemented by Feng and Doolittle (1987) and Hanks et al (1988) was used to generate a phylogenetic tree as described in Example 1. In each case the catalytic domain alone was used for comparison. The two kinase related domains of the JAK1 protein were compared independently. Branch order is a function of structural similarity, branch length a function of sequence identity. The abbreviations used are: SRC=c-src; YES=c-Yes; FES=c-fes; CSFI-R=Colony stimulating factor-1 receptor; KIT=c-kit; PDGF-R=Platelet derived growth factor receptor-A; RET=c-RET; ANP-A=Atrial naturetic peptide receptor-A; ANP-B=Atrial naturetic peptide receptor-B; MOS=c-mos; PBS2=polyxin B antibiotic resistance gene product; STE7=sterile mutant wild-type allele gene product; JAK1/1=Domain-1 of Human JAK1; JAK1/2=PTK domain of Human JAK1.

Figure 7B:
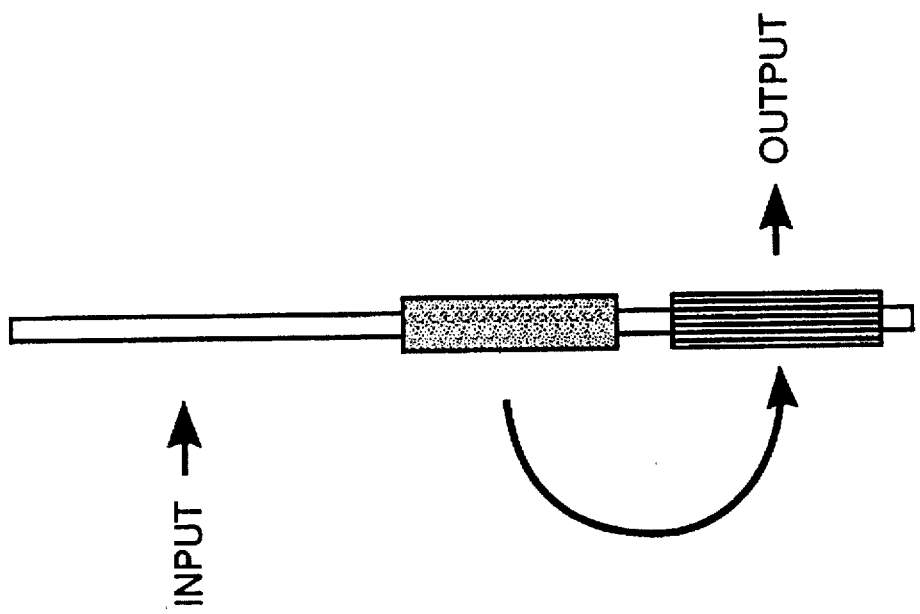
Figure 7A:
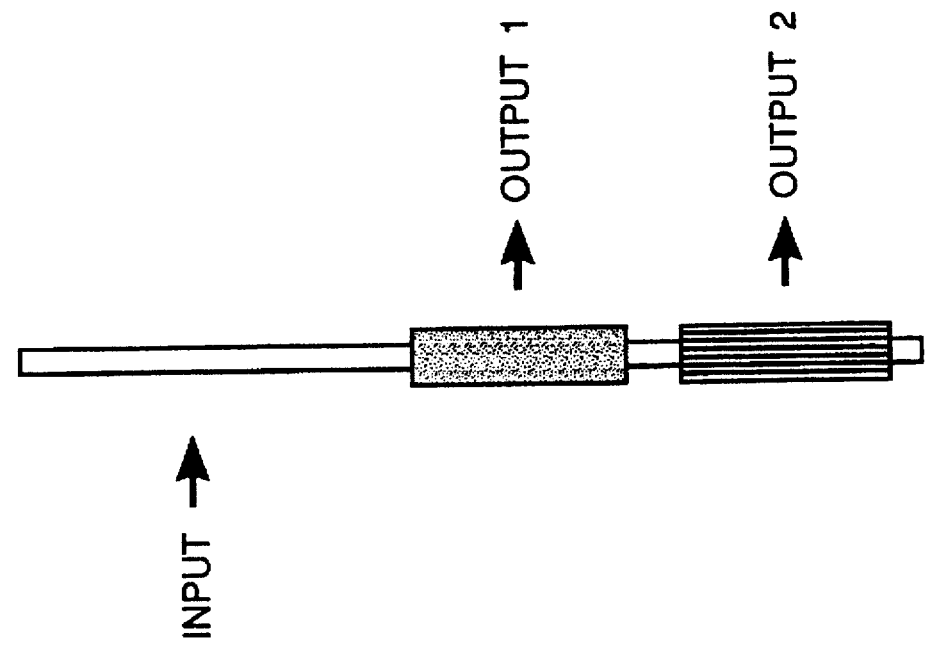

FIGS. 7(A and B) is a diagramatic representation showing models for the role of members of the JAK family of PTKs in signal transduction. Two possible scenarios are considered based on an extrapolation of the current notions of the role of PTKs in signal transduction. In panel 7A the N-terminal domain of the JAK protein serves to sense a particular metabolic cue and convert this input into two distinct outputs. Presumably the output of the second PTK-related domain is tyrosine kinase activity; the activity of Domain-1 remains unknown. In panel 7B an alternative scenario is considered. In this case the function of Domain-1 is the regulation of the PTK domain. In this scenario the sole output of the JAK protein is the PTK activity.

FIGS. 8(A–G) is a representation of a nucleotide sequence and predicted amino acid sequence of murine JAK2. The nucleotide sequence is numbered beneath each line of sequence, from the first nucleotide of the most 5' clone. The predicted amino acid sequence, in one letter code, is numbered at the end of each line of sequence. The two putative kinase domains are shown boxed with arrows, and the kinase consensus motifs are enumerated according to the nomenclature of Hanks et al (1988). The subscript a denotes the kinase-related motifs present in the first kinase-related domain, which are numbered according to the same nomenclature. SEQ ID NO: 2 contains the DNA sequence and SEQ ID NO: 25 contains the amino acid sequence.

Figure 9:
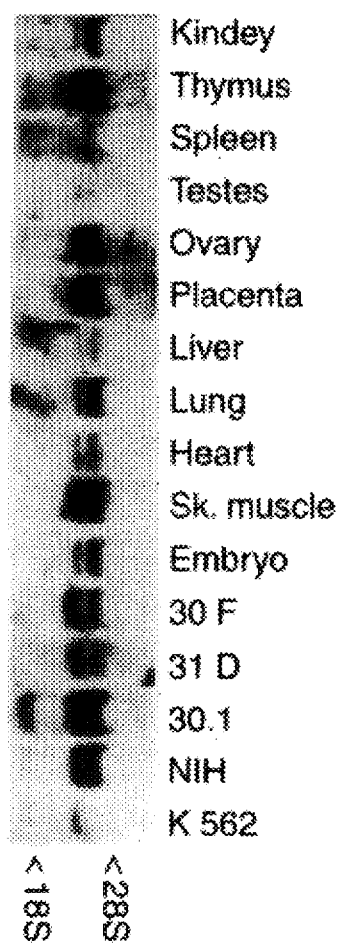

FIG. 9 is a photographic representation showing expression of JAK2 in murine tissues. Northern blot analysis of 5 µg of mRNA from each of the tissues shown on top of the figure and from various murine (30F: mammary fibroblasts; 31A: mammary epithelial cells; 30.1: factor independent subline of the hemopoietic cell line FDC.P1; NIH: fibroblasts) and human (K562: chronic myelogenous leukaemic cells) cell line. The blots were hybridized with a $^{32}$P-labelled 2.2 kp JAK2 probe and autoradiography was for 4 days. The relative mobilities of the 28S and the 18S rRNA are indicated.

Figure 10:
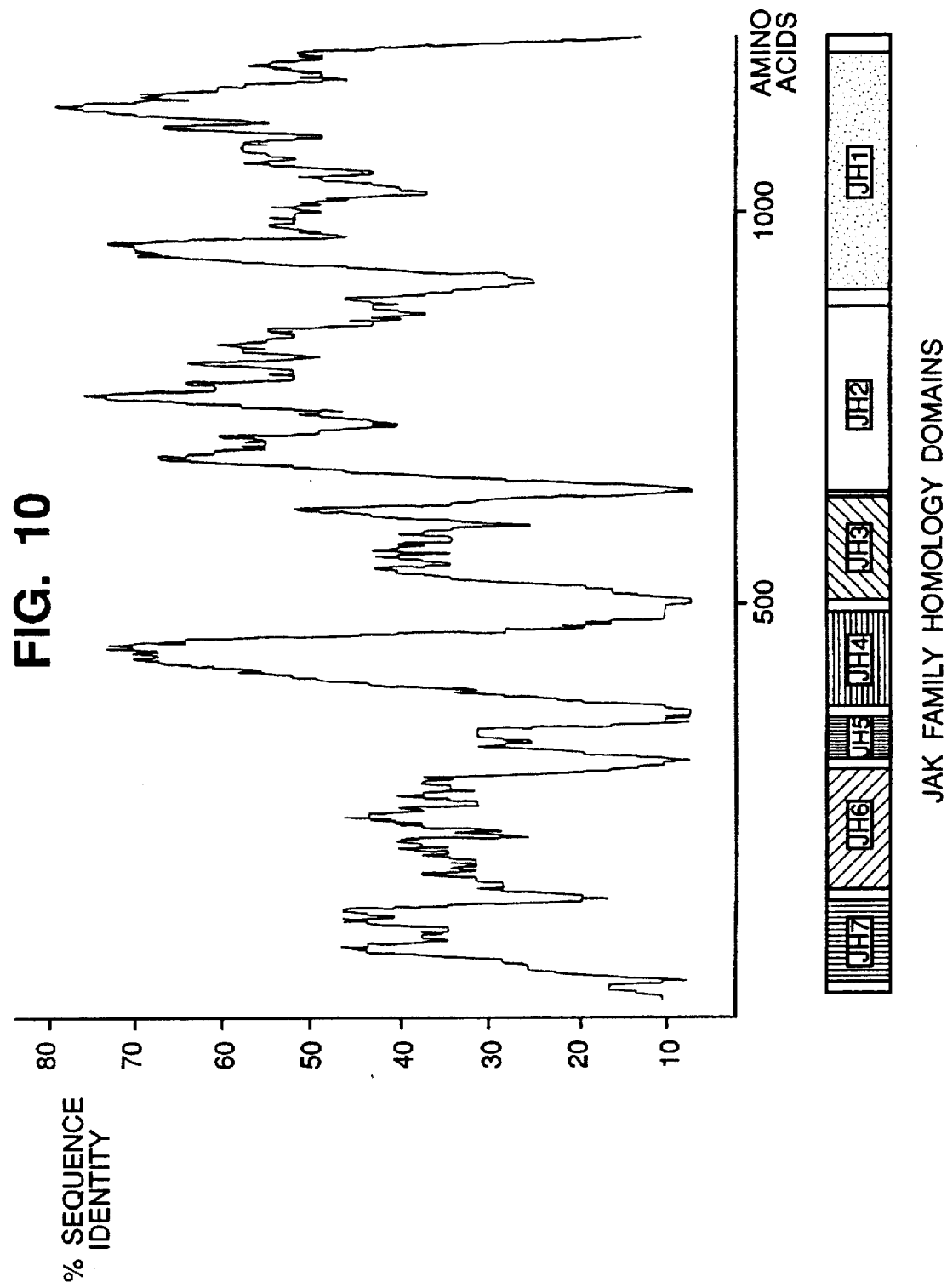

FIG. 10 is a graphical representation showing comparison of JAK1 and TYK2 amino acid sequences. The amino acid sequences of JAK1 (Wilks et al, 1991) and TYK2 (Firmbach-Kraft et al, 1990) were compared using the HOMOLOGY option in the programme SEQMATCH, using a window length of 21 amino acids. The ordinate of the graph represents the percentage identity between the two sequences, the abscissa represents the amino acid position in JAK1 at which the particular level of identity was calculated. The shaded boxes below the graph represent arbitrarily ascribed JAK homology domains as discussed in the text and further demonstrated in FIG. 11.

FIGS. 11A–C is a representation showing amino acid sequence comparison of members of the JAK family of PTKs. The amino acid sequences of JAK1 (Wilks et al, 1991) (designated J1 in this figure), JAK2 (J2 in this figure), and TYK2 (Firmbach-Kraft et al, 1990) (T2 in this figure) were aligned using the CLUSTAL program (Higgins and Sharp, 1988). The numbering system is relative only to the first amino acid of JAK1, and does not take into account the insertion of gaps into this sequence, it is therefore useful only as a relative measure of location. The extent of each of the JAK homology domains was determined with reference to the homology plot shown in FIG. 10. Amino acid positions conserved in at least 2 out of the 3 sequences presented are bolded and presented below the TYK2 sequences as a consensus sequence.

FIG. 12 is a representation showing a comparison of the JH3/JH4 domain region with SH2 domains. The two SH2 domains of GAP (the more N-terminal domain denominated GAP-N (residues 178-269), the more C-terminal, GAP-C, (residues 348-438) (Trahey et al. 1988), and the SH2 domain of v-crk (residues 248-354) (Mayer et al. 1988) were compared with the JH3/JH4 of JAK1 (residues 425-536) (Wilks et al. 1991), JAK2 (residues 252-359) (this manuscript) and TYK2 (residues 449-555) (Firmbach-Kraft et al. 1990). Amino acids held in common between the two classes of sequence are denoted by vertical lines between the two sets of sequences. Conserved residues held in common by members of the same class of domain are bolded.

EXAMPLE 1

MATERIALS AND METHODS

Screening of cDNA libraries

Several cDNA libraries were screened according to the protocols outlined in Maniatis et al. (1982). cDNA libraries from Murine NFS TPA activated spleen (Clontech cat.#ML1018), murine swiss-albino 3T3 fibroblast (Clontech cat.#1023b), murine balb/c bone marrow (Clontech cat.#ML1007), murine swiss-webster whole brain (Clontech cat.#ML1002), murine ICR linoleic acid activated pleural macrophage (Clontech cat.#ML1005b), and human 1st-trimester foetal liver (Clontech cat.#HL1005b) were all generated in λgt 11. cDNA libraries from murine Balb/c testis (Clontech cat.#ML1020b), murine day 10 embryonic neuro-epithelium (Reid et al. 1990) and human foreskin fibroblast cell line AG1518 (Claesson-Welsh et al. 1989) were generated in λgt10. Around $10^6$ recombinants of each of these libraries were screened on each occasion.

Library screening was carried out as follows. The FD22 (JAK1) PCR clone was labelled by nick-translation (Maniatis et al. 1982) and used to screen the murine libraries. A murine cDNA clone of 1.8 kb was isolated amongst 3 other positives from the neuro-epithelial and bone marrow cDNA libraries. Two full-length human JAK1 cDNA clones were isolated from the unamplified human foreskin fibroblast cell-line AG1518 by using the murine cDNA as a probe. Hybridisation was at 65° C. in 6×SSC; 1% SDS; 0.5% Blotto; 200 µg/ml sonicated and denatured herring sperm DNA. After hybridisation, the stringency of the final wash was 0.2×SSC; 0.1% SDS at 65° C. Filters were autoradiographed overnight using Kodak XAR-5 X-ray film.

For JAK2, the murine macrophage was screened first with the FD 17 (JAK2) PCR clone, yielding 5 positives, and a portion of the longest cDNA clone isolated and used to screen the remaining cDNA libraries. Hybridisation conditions were as above for JAK1.

DNA sequencing

Two strategies were employed for the sequencing of JAK1 and JAK2 cDNA clones. In the case of the human JAK1 sequence, the Erase-a-Base kit (PROMEGA) was employed to generate nested deletions of the largest EcoRI fragment. All of the murine JAK2 sequence data, and the remainder of the human JAK1 sequence, was determined using oligonucleotide primers based on previously determined DNA sequence. In each case the sequence information was generated using the dideoxynucleotide chain termination method (Sanger et al. 1977). All sequence information was determined on both strands.

Northern Analysis

Poly A+mRNA samples were prepared as elsewhere described elsewhere (Wilks and Kurban, 1988). Aliquots (1 µg) were analysed by electrophoresis on a 1% agarose gel containing 2.2M formaldehyde; 20 mM MOPS, pH 6.8; 1 mM EDTA; 5 mM sodium acetate, and transferred to Hybond (Amersham, cat #RPN303N) or nitrocellulose (Schleicher & Schuell, BA85, cat #401196) membranes. Filters were prehybridised for 4 hr in 50% formamide containing 3×SSC; 5×Denhardts; 10 mM HEPES pH 7.0; 100 µg.ml 1; poly C; 100 µg/ml denatured herring sperm DNA; 10 µg/ml E. coli DNA; 0.1% SDS, and hybridised in the same solution with nick-translated $^{32}$P-labelled murine or human JAK1 or JAK2 insert, for 18 hr. at 42° C. Filters were washed to a final stringency of 0.2×SSC; 0.1% SDS at 65° C., before exposure to Kodak XAR-5 X-ray film, with two intensifying screens.

Antibody Reagents and Protein Analysis

Polyclonal rabbit antisera M7 and M8 were raised against affinity purified pGEX/JAK1/1 bacterial fusion protein (see section on kinase assays). Polyclonal antibodies M3 and M4 against the C-terminal peptide (-TSFQNLIECFEALLKC-) (SEQ ID NO: 4) of JAK1 were raised in rabbits. Peptide was coupled to Keyhole Limpet Heamocyanin with 0.05% gluteraldehyde, emulsified in Freunds' complete adjuvant and injected intradermally at several sites. The animals were boosted four and seven weeks later with coupled peptide emulsified in Freunds' incomplete adjuvant and bled ten days after the last injection.

Cells were metabolically labelled with either $^{35}$S-methionine or $^{32}$P-orthophosphate in methionine- or phosphate-free medium containing 100 µCi/ml and 1 mCi/ml isotope respectively. RIPA-buffer (20 mM Tris, pH 7.5 containing 1% Triton X100, 1% Na deoxycholate, 0.1% SDS, 1 mM EDTA, 1 mM PMSF) extracts were incubated on ice with antiserum and immune-complexes isolated using Protein A bearing Staphylococus aureus bacteria. Proteins were resolved by SDS-PAGE (Laemmli, 1970) and radioactively labelled bands detected by exposure to X-ray film (Kodak XAR-5). The RIPA buffer for $^{32}$P-labelled cells contained in addition 20 mM EDTA, 10 mM NaF, 100 µM orthovanadate as phosphatase inhibitors.

Phosphoamino-acid analysis of excised $^{32}$P-labelled bands was carried out exactly as described by Hunter and Sefton (1980) Western blot analysis was performed as described by Towbin et al. (1979) as modified in Ziemiecki et al (1990) using either alkaline phosphatase or $^{125}$I-labelled protein-A as a detection system.

Protein Kinase Assays

A variety of protocols have been tried in order to revel the PTK activity of the JAK1 protein. First, extraction of murine mammary fibroblasts, Reichmann et al (1989) has been performed in a range of buffers, containing Triton-X100 or Nonidet P40 (1.0%) alone, or with added Sodium Deoxycholate (0.5% or 1.0%) or in RIPA buffer (containing 1.0% Triton-X100; 1.0% Sodium Deoxycholate; 0.1% Sodium Dodecylsulphate). Cells have been extracted in the presence or absence of phosphatase inhibitors, such as 20 mM EDTA, 10 mM NaF and 100 µM Na2V04.

After immunoprecipitation, kinase assays have been performed in a range of ATP concentrations (100 nM–10 mM) or with carrier-free γ-32P-ATP (Amersham cat #10169) in either 20 mM Tris, pH 7.4 or 50 mMM HEPES pH 7.4, with either 10 mM Mn$^{++}$, Mh$^{++}$ or Zn$^{++}$ as divalent cation. Incubations have been performed on ice (15 min), at 25° C. (15 min), at 30° C. (15 min) or at 37° C. (2 min) in the presence or absence of the phosphatase inhibitor Na2V04. Finally, γ-32P-GTP was employed as phosphate donor in lieu of γ-32P-ATP, with no success.

In order to generate the JAK1/glutathione transferase fusion proteins shown in FIG. 4, domain-1 (from nucleotides 1770-2672 in FIG. 2) and the PTK domain (from nucleotides 2672-end in FIG. 2, thus including 5 extra amino acids beyond the ATP binding glycine motif) were each fused into the BamHI site of pGEX2. The fusion protein was induced by the addition of 1 mM IPTG as described elsewhere (Smith and Johnson, 1983) and Western blot analysis performed on an induction time course with the M3 anti-JAK1 serum, and the anti-phosphotyrosine antiserum (Kamps and Sefton, 1988). Several sources of anti-phosphotyrosine antisera were tried. The data in FIG. 4b were obtained using a commercially available monoclonal antibody preparation PY-20 (ICN). In control experiments, induction of the insertless pGEX or pGEX/JAK1 fusion protein produced no detectable tyrosine phosphorylation of bacterial substrates and the reactivity of the anti-phosphotyrosine antiserum could be completely abolished by the additional of phenyl phosphate.

Computer Aided Sequence Analysis

Amino acid sequence comparisons were performed using an alignment programme from the Staden-based suite of programmes on a VAX VMS 5.2. The phylogenetic analysis of the two kinase-like domains of JAK1 was performed using the tree-building concept of Fitch and Margoliash (1967) as implemented by Feng and Doolittle (1987). The SCORE programme used to construct the difference matrices from which the trees were derived using the BORD and BLEN programmes, were all the gift of Dr. R Doolittle of the University of California-San Diego.

The sequence alignment shown in FIG. 11 was assembled using the CLUSTRAL program (Higgins and Sharp, 1988) on a VAX VMS 5.2 minocomputer. The homology plot shown in FIG. 10 was assembled using the HOMOLOGY option of the programme SEQMATCH. Database searches with each of the JAK homology domains was reformed using the FASTA programme, based on the Pearson/Lippman algorithm (Pearson and Lippman, 1988).

RACE/Anchor PCR

RACE/Anchor PCR (Frohman et al, 1990; Loh et al, 1990) was performed by a modification of the original protocol. Briefly, 2 µg of poly(A+)mRNA is converted to cDNA using an Amersham cDNA synthesis kit (cat No. RPN 1256) and 40 ng. of a JAK2 specific oligonucleotide primer (5'-TACACCTTTAAATATTTTTGT-3') (SEQ ID NO: 5). Prior to the addition of the reverse transcriptase, the reaction mixture was heated to 65° C. cDNA synthesis was initiated by the addition of 20 units of reverse transcriptase, and the reaction incubated at 55° C. for 75 minutes. The newly synthesised cDNA was recovered by passage through a spun sephadex column (Maniatis et al, 1982) followed by ethanol precipitation. The mRNA/cDNA heteroduplex was G-Tailed in 30 µl containing 140 mM potassium cacodylate, 30 mM Tris, (pH7.2), 1 mM $CoCl_2$, 0.1 mM DTT, 6 mM dGTP and 15 units of TdT (IBI), for 10 minutes at 37° C. The reaction was terminated by heating to 65° C. for 15 minutes and then diluted to 500 µl with 10 mM Tris. HCl (pH7.5). 1 mM EDTA. For the RACE/Anchor PCR, 10 µl of the tailed cDNA was reconstituted into 100 µl PCR buffer (50 mM KCl, 10 mM Tris. HCl[pH8.3], 1.5 mM $MgCl_2$, 0.01% gelatin, 200 µM of each dNTP) to this was added 50 ng of "poly-C" oligonucleotide primer (5'-CTCGAGTCGACGAATTC$_{14}$-3') (SEQ ID NO: 6) and 2.5 units of TAO polymerase (Cetus). The complementary strand of the cDNA was synthesised with one cycle of 95° C. (5 minutes), 52° C. (5 minutes) and 68° C. (40 minutes), whereupon 500 ng of the "RACE/Anchor" primer (5'-CTCGAGTCGACGAATTC-3') (SEQ ID NO: 6) and a nested JAK2 specific primer (5'-CTTGCTTAATACTGACATCA-3') (SEQ ID NO: 7) were added and the reaction mix subjected to 30 cycles of 95° C. (1 minute), 52° C. (2 minutes) and 68° C. (5 minutes). The PCR product was phenol/chloroform extracted, precipitated and resuspended in 100 µl of water. The amplified material was then kinased, size fractionated on a low-melting temperature agarose gel and cloned into SmaI cleaved M13mp8. Plaques were screened by hybridisation with a JAK2 cDNA and positives sequenced.

EXAMPLE 2

Isolation and DNA sequencing of cDNA clones encoding JAK1

JAK1 cDNA was cloned using PCR. Northern analysis (FIGS. 1a and b) demonstrated that in both mouse and human tissues and cell lines FD22 (JAK1) was encoded by a single widely expressed 5.4 kb mRNA. Human cDNA clones of FD22 (JAK1) were isolated from a human foreskin fibroblast cell line (AG 1518) cDNA library (Claesson-Welsh et al, 1989). Two of the 8 primary isolates cloned contained inserts which were candidates for being full-length cDNAs (~5.3 kb).

The nucleotide sequence of human JAK1 is shown in FIG. 2. The 5' end of the clone has stop codons in all 3 reading frames prior to the putative initiation ATG. Two ATG start codons in frame with the longest open reading frame were found at positions 40 and 76 in the nucleotide sequence shown in FIG. 2. The first of these is embedded in a particularly poor "Kozak" consensus sequence (Kozak, 1984) (-TAAATGCAG-), (SEQ ID NO: 9) whereas the second matches strongly with the optimal consensus sequence defined by Kozak, namely -GCCATGGCT- (SEQ ID NO: 10). The second ATG is considered to be the initiation codon for this protein, since the first one transgressed one of the strongest correlations found in the sequences which precede initiation codons, namely the presence of a T residue (in lieu of an A residue) 3 nucleotides before the ATG sequence. At the 3' end, and in-frame stop codon at position 3502 defines the C-terminus of the protein. A large (1.405 kb) 3' untranslated region containing a polyadenylation signal completes the mRNA sequence.

The JAK1 coding region of 3426 bp encodes a protein of 1142 amino-acids with a calculated molecular mass of 132,000 daltons. The PTK catalytic comain is located towards the C-terminus of the JAK1 protein (FIG. 2). In describing the structural features of this domain we have chosen to adopt the nomenclature of Hanks et al (1988). The putative ATP binding site composed of the motif GLY-X-GLY-X-X-GLY- (SEQ ID NO: 3) (subdomain 1) followed by an invariant lysine residue (subdomain II) is located between amino acid residues 871 and 896 of the JAK1 protein. The core motifs of the PTK catalytic domain (subdomains VI to IX) are also in their appropriate locations, and are well conserved with respect to their primary sequence and their relationship to each other. The presence of a tyrosine residue at position 1022 in the JAK1 protein, 11 residues C-terminal to sub-domain VII (a similarly placed tyrosine is a site of tyrosine autophosphorylation in v-fps; Weinmaster et al, 1984) is a consistent feature of members of the PTK family and is considered diagnostic of membership of this class of kinases. The arginine residue at position 1126 (domain XI) marks the end of the highly conserved regions of the PTK catalytic domain and the entire catalytic domain of 255 amino acids is approximately 28% (with c-fes; Wilks and Kurbon, 1988) to 37% (with TRK; Kozman et al, 1988) identical to other functionally defined PTKs. Finally, there is a rare variant of the highly conserved subdomain VIII motif (residues 1032-1039), which is believed to lie close to the active site (Hanks et al, 1988). The presence of phenylalanine and tyrosine flanking the conserved tryptophan in this motif is unique to JAK1 and JAK2.

A second protein kinase-related domain (designated here Domain-1) is located between amino acids 578 and 824, 47 amino acids N-terminal to the putative PTK domain. All of the conserved elements of protein kinases are preserved spatially in this domain. In FIG. 2 these elements are numbered with respect to their similarity to the subdomains of protein kinases described by Hanks et al, (1988) (with the suffix$_a$, e.g. III$_a$) and the amino acid sequences of the two kinases-related domains of JAK1 are compared to each other and to human CDC2 (Lee and Nurse, 1987) in FIG. 3a. The overall structural similarity of this domain to the kinase domains of both the PTK and threonine/serine kinase families strongly suggest that this region of the protein also functions as a protein kinase. There are, however, significant differences in the sequences of key motifs within this domain which suggest that Domain-1 may confer a catalytic activity other than serine/threonine or tyrosine phosphorylation. For example, sub-domain VI$_a$ is poorly conserved with respect to the equivalent motifs in the other kinase families, and the normally invariant -ASP-PHE-GLY- sequence of the PTK and threonine/serine kinase families (sub-domain VII$_a$) is replaced by the motif ASP-PRO-GLY- in Domain-1 of JAK1. As has been noted elsewhere, the conservation of the precise sequence of sub-domain VI in the PTK and threonine/serin kinase families appears to correlate with the substrate specificity of the kinase. Thus, it is possible that Domain-1 of the JAK1 kinase has a substrate specificity other than that exhibited by the PTK and threonine/serine kinase has a substrate specificity other than that exhibited by the PTK and threonine/serine kinases. In support of this notion there are subtle differences in the normally consistent spacing between certain key motifs in Domain-1 of JAK1. The components of the ATP binding site (sub-domains I$_a$ and II$_a$) are some 7 amino acids further apart in this domain that they are in both the PTK family and the threonine/serine kinase family. Moreover, the spacing between sub-domains VI$_a$ and VII$_a$ in this region is also longer by 9 amino acids. Conversely, the distance between sub-domains VII$_a$ and IX$_a$ is 7 amino acids shorter than the corresponding region in the PTK catalytic domain. The overall structure of this domain can be expected to be somewhat different to the catalytic domains of the members of the PTK and threonine/serine kinase families.

The sequences N-terminal to Domain-1 bear no homology to any other portion of a previously described protein kinase. Specifically, no homology was detected to the SH2 domain described for the cytoplasmic PTKs such as c-fes/fps (Sadowski et al, 1986) GAP (Trahey et al, 1988) and the phospholipase-C family of proteins (Suh et al, 1988). This is a particularly interesting observation since no other non-receptor PTK has been described which lacks this feature. A hydrophilicity plot failed to demonstrate the present of a hydrophobic domain characteristic of the growth factor receptor type of PTK (FIG. 3b) suggesting that this protein is wholly intracellular like other members of the non-receptor class of PTKs. The one outstanding feature of the JAK1 hydropathy plot is the highly hydrophilic sequence between residues 320-350. This sequence is not conserved in the murine JAK2 protein, however, its remarkable nature suggests that it may well be involved in some function of the JAK1 protein.

Expression of JAK1 protein

Several antisera were generated against the human JAK1 protein. Polyclonal antisera directed against the hexadecamer -TSFQNLIECFEALLKC- (SEQ ID NO: 4) (the C-terminal 15 amino acids of JAK1) were raised in rabbits and used to investigate the nature of the JAK1 protein. A second rabbit antiserum was generated using a pGEX bacterial fusion protein containing the entire Domain-1 region of the human JAK1 protein (see Example 1). Preliminary sequence analysis of cDNA clones of murine JAK1 demonstrated that the C-terminus of the human and murine versions of this protein were identical whereas the murine and human Domain-1 regions exhibited a very high degree of identity. Both systems have thus been used interchangably in the investigation of the properties of the JAK1 protein.

Both antisera have been used for Western blot analyses and immunoprecipitation studies and the data confirm the mRNA expression studies shown in FIG. 1. For example, antisera M3 and M8 both immunoprecipitate a protein of the same apparent molecular weight (130 kDaltons) from $^{35}$S-methionine labelled murine breast fibroblasts (FIG. 4a). From the same source, $^{32}$P-orthophosphate labelled JAK1 was immunoprecipitated as a phosphothreonine and phosphoserine containing phosphoprotein. It is a feature characteristic of members of the protein tyrosine kinase family that they are able to accomplish an act of self phosphorylation in vitro. Intriguingly, despite the high degree of sequence similarity held by the PTK-related sequence of JAK1 to the PTK family in general, it was not possible to demonstrate tyrosine kinase catalytic activity in immunoprecipitates of this protein from any of the murine or human sources tested. A wide range of possibilities has been tested in search of suitable conditions for the demonstration of this activity. These are listed in Example 1. The reason for the lack of activity may lie with a steric effect of the antibody in the active site of the enzyme.

In order to determine whether domain-1 or the PTK domain, in isolation, bore catalytic activity, bacterial fusion proteins of each were generated with the glutathione transferase protein of Schistosoma japonicum (Smith and Johnson, 1988) and an attempt was made to demonstrate with the aid of anti-phosphotyrosine antibodies (Kamps and Sefton, 1988) the co-ordinate induction of the fusion protein and tyrosine phosphorylated protein. In this system there is no cross-reactive background of the anti-phosphotyrsine antiserum, since there are no tyrosine kinases in bacteria (FIG. 4b). The phosphorylation of bacterial proteins on tyrosine is thus easily detectable with such a serum. In this series of experiments neither pGEX without insert nor pGEX bearing Domain-1 (pGEX/JAK/1/1) demonstrated any tyrosine kinase activity. The pGEX/JAK/1 fusion protein was further purified by affinity chromatography on a reduced glutathione column and have failed to detect any kinase activity using either histones, casein or enolase as an exogenous substrate. The pattern of inducible tyrosine phosphorylation exhibited by the pGEX PTK fusion protein (pGEX/JAK/2) (FIG. 4b) is unusually simple for an ectopically expressed PTK fusion protein. Remarkably, the autophosphorylation of the fusion protein itself does not seem to occur, an observation which may go some way toward explaining why we have had difficulty in demonstrating PTK activity in the intact protein.

cDNA clones covering the coding region of the PCR clone FD17 (JAK2) have been isolated from a range of murine cDNA libraries. The predicted amino acid sequences of JAK2 and JAK1 show several regions of significant similarity to each other (FIG. 5, see also Example 3).

Phylogenetic analysis

The phylogenetic relationship of the catalytic domains of most of the protein kinases has been determined using the tree-building programme of Feng and Doolittle (1987). FIG. 6 shows the phylogenetic relationship of the two kinase-related domains of the JAK1 protein to the rest of the kinase family. It is concluded from this family tree that these two domains had a common ancestor which pre-dated the development of the PTK sub-family. It is of interest to note that the kinase-related domains of the ANP-receptor/guanylate cyclase family diverge at a point close by.

EXAMPLE 3

Cloning and sequencing of JAK2

Sequence of Murine JAK2

The PCR clone FD17 was used as a basis to begin the cloning of longer cDNA clones of murine JAK2. cDNA were isolated from a range of cDNA libraries, and by RACE (Frohman et al. 1989, Loh et al. 1989). The sequence of murine JAK2 is presented in FIG. 8. The predicted amino acid sequence indicates that this protein is highly related to JAK1. At the C-terminus, and extending approximately 270 amino acids towards the N-terminus (AA 715-980), are sequences bearing all the hall marks of a PTK catalytic domain. These are labelled in FIG. 8 according to the Hanks nomenclature. Immediately N-terminal to this (AA 400-660) lies the kinase-related domain characteristic of this class of PTKs (Wilks et al, 1991). The approach outlines in Example 2 in relation to JAK1 was followed and assigned these kinase related domains according to the Hanks nomenclature, appending the suffix Na to denote their origin. One unusual feature of this domain is an apparent insertion of seven amino acids between elements VIIa and VIIIa (Hanks nomenclature; Hanks and Quinn, 1991) with respect to other members of this family. This feature appeared in only one clone of the four sequences which covered this region, and it remains possible that its presence is due to an infrequent splicing abberation, rather than being of functional significance.

Distribution of JAK2

Northern analysis of the expression of JAK2 in the mouse demonstrated two mRNA transcripts (4.8 and 4.4 kp) hybridizing to the JAK2 probe under low and high stringency hybridization conditions (FIG. 9). It is intriguing to note that the levels of these transcripts alter with respect to one another in different tissues. Fore example, the kidney, spleen and lung appear to express predominantly the larger form, whereas ovary, placenta, skeletal (sk) muscle and all murine cell lines analyzed express both forms at about equal levels.

Under low stringency hybridization conditions the murine JAK2 probe recognizes human JAK2 RNA (K562), however, only the smaller transcript of 4.4 kp could be detected. At this point, the origins of either of the two transcripts are unclear and no differential splicing events which could account for the differences between them could be detected. However, the major source of size differential in these transcripts may lie in the use of different polyadenylation signals. JAK2 is widely expressed in mouse organs, albeit to different levels. High expression was found in thymus, skeletal muscle, ovary and placenta, but JAK2 transcripts were barely detectable in testes or liver. In addition, JAK2 expression was detected in murine cell lines of fibroblastic (30F, NIH), epithelial (31D) and hemopoietic (30.1) origin.

JAK Family Homology Domains.

The cloning of JAK1 and JAK2 has facilitated the identification of JAK family homology domains. FIG. 10 shows a comparison of the amino acid sequences of JAK1. Sequence identity between these two proteins manifests itself as seven clearly defined homology domains. These seven domains are defined at a primary sequence level in FIG. 11. The PTK domain is classified as the JAK-homology Domain 1 (JH1), the second kinase related domain as the JH2 Domain, and so on to JH7. The boundaries of the JAK homology domains are arbitrary, and may or may not define functional domains. However, their delineation is a useful device to aid the consideration of the overall structural similarity of this class of proteins. The structure of the JH1 and JH2 Domains are described in Example 2. The JH3 is one of the least highly conserved of the JAK homology domains, each family member bearing between 35% (JAK2) to 50% (JAK1) of the deduced consensus sequence. The JH4 domain bears the sequence -GLYVLRWS- (SEQ ID NO: 11) close to its C-terminal boundary, which has some degree of homology to the SH2 domain core sequence (see below). In addition, the most highly conserved sub-domain of this region bears a potential tyrosine phosphorylation site, namely, -VDGYFRI- (SEQ ID NO: 12). Overall, the JH4 domain has between 51% (JAK2) and 64% (JAK1) of the deduced consensus sequence for this domain. Each of the remaining JAK homology domains has been independently screened against the NBRL and EMBL databases using the FASTA programme. There were no compelling homologies found with anything in these databases. It is concluded that these domains are structurally and functionally conserved in members of the JAK family of PTKs, but may not, incontradistinction to the SH2 and SH3 domains of the src family of PTKs, have a role to play in other signal transduction molecules.

The apparent absence of an SH2 domain in any of the JAK family of PTKs is intriguing. Subtle sequence similarities have been detected between SH2 consensus sequences and portions of the JH3 and JH4 domains (H. Hanafusa and A. Bernards, personal communication). FIG. 12 shows an alignment of these two domains. Whilst the similarity of the JH3 domain to SH2 domains is most evident in the region surrounding the SH2 core sequence (FLVRES), the homology does not extend far in either direction beyond this region, and only reappears again close to the C-terminal boundary of the SH2 domain. This lack of extensive homology, particularly in many of those elements most highly conserved between SH2 domains (Koch et al, 1991) (presumably indicating those residues most intimately involved in the conserved function of this domain), suggests that the homology detected is either happenstance, or the product of considerable sequence divergence in evolution. The SH2 domain is currently believed to interact with phosphorylated tyrosine residues on the substrates of PTKs (reviewed in Pawson, 1989; Koch et al, 1991). Whether the JH3/JH4 domains play a similar functional role remains to be determined.

EXAMPLE 4

To show that JAKs are represented in a range of animals, oligonucleotide probes were prepared and used to amplify and screen genomes from a variety of animals. JAK DNA was detected in Drosophila, xenopus, mouse and human genomes. The main conserved sequence was DPG common to all animals tested.

REFERENCES:

Claesson-Welsh, L., Eriksson, A., Westermark, B. and Heldin, C. H., *Proc. Nat. Acad. Sci. USA* 86: 4917–4921, 1989.

Feng, D. F. and Doolittle, R. F. *Jour. Mol. Evolution* 25: 351–360, 1987.

Fitch, W. M. and Margoliash, E., *Science* 12: 279–284, 1967.

Hunter T., and Sefton, B. M. *Proc. Nat. Acad. Sci.* 77: 1311–1315, 1980.

Kamps, M. P., and Sefton, B. M. *Oncogene* 2: 305–315, 1988.

Kozak, M. *Nucleic Acids Res.* 12: 857–872, 1984.

Kozma, S. C. Redmon, S. M. S., Xiano-Chang, F. Saurer, S. M. Groner, B., and Hynes, N. E. *EMBO J.* 7: 147–154, 1988.

Kyte, J. and Doolittle, R. F. *J. Mol. Biol.* 157: 105–132, 1982.

Laemmli, U. K. *Nature (London)* 227: 680–685, 1970.

Lee, M. G. and Nurse, P. *Nature (London)* 327: 31–35, 1987.

Maniatis, T., Fritsch, E. F., and Sambrook, J., in *Molcular Cloning: A Laboratory Manual* Cold Spring Harbor, M.Y. 1982.

Moran, M. F., Koch, C. A., Sadowski, I., and Pawson, T. *Oncogene* 3: 665–672, 1988.

Reichmann, E., Ball, R., Groner, B., and Friis, R. R. *J. Cell Biol.* 108: 1127–1138, 1989.

Smith, D. B. and Johnson, K. S. *Gene* 67: 31–40, 1988.

Suh, P., Ryu, S. H., Moon, K. H., Suh, H. W., and Rhee, S. G. *Cel* 54: 161–169, 198.

Towbin, H., Stehelin, T., and Gordon, J., *Proc. Nat. Acad. Sci USA* 76: 4350–4354, 1979.

Weinmaster, G., Zoller, M. M., Smith, M., Hinze, E., and Pawson, T. *Cell* 37: 559–568, 1984.

Wilks, A. F. and Kurban, R. R. *Oncogene* 3: 289–294, 1988.

Ziemiecki, A., Mueller, R. G., Xiao-Chang, F., Hynes, N. E. and Kozma, S., *EMBO J.* 191–196, 1990.

Dymecki, S. M., Neiderhuber, J. E., and Desiderio, S. v. *Science* 247: 332–336, 1990.

Firmbach-Kraft, I., Byers, M., Showes, T., Dalla-Favera, R., and Krolewski, J. J., *Oncogene* 5: 1329–1336, 1990.

Frohman, M. A., Dush, M. K. and Martin, G., *Proc. Nat. Acad. Sci. USA* 85: 8998–9002, 1988.

Hanks, S. K. and Quinn, A. M. *Methods in Enzymology* 200: 38–62, 1991.

Hanks, S. K., Quinn, A. M. and Hunter, T. *Science* 241: 42–52, 1988.

Higgins, D. G. and Sharp, P. M. *Gene* 73: 237–244, 1988.

Holtzman, D. A., Cook, W. D. and Dunn, A. R. *Proc. Natl. Acad. Sci. USA* 84: 8325–8329, 1987.

Koch, C. A., Anderson, D., Moran, M. F., Ellis, C., and Pawson, T., 252: 668–674, 1991.

Loh, E. Y., Elliott, J. f., Cwirla, S., Lanier, L. L. and Davis, M. M. *Science* 243: 217–220, 1989.

Marth, J. D., Peet, R., Krebs, E. G., and Perimutter, R. M. *Cell* 43: 393–404, 1985.

Martinex, R., Mathey-Prevot, B., Bernards, A. and Baltimore, D. *Science* 237: 411–414, 1987.

Mayer, B. J., Hamaguchi, H., and Hanafusa, H., *Nature* 332: 272–274, 1988.

Nishizawa, M., Semba, K., Yoshida, M. C. Yamamoto, T., Sasaki, M., and Toyoshima, K. *Mol. Cell. Biol.* 6: 511–517, 1986.

Pawson, T., *Oncogene* 3: 491–495, 1988.

Pearson, W. R. and Lippman, D. J. *Proc. Natl. Acad. Sci.* 85: 2444–2448, 1988.

Reid, H. H., Wilks, A. F., and Bernard, O., *Proc. Nat. Acad. Sci.* 87: 1596–1600, 1990.

Sadowski, I., Stone, J. C., and Pawson, T. *Mol. Cell. Biol.* 6: 4396–4408, 1986.

Sanger, F., Nicklen, S., and Couson, A. R., *Proc. Nat. Acad. Sci. USA* 74: 5463–5467, 1977.

Semba, K., Nishizawa, M., Myajima, N., Yoshida, M. C., Sukagawa, J., Yamanishi, Y., Sasaki, M., Yamamoto, T., and Toyoshima, K., *Proc. Natl. Acad. Sci.* 83: 5459–5463, 1986.

Sukegawa, J., Semba, K., Yamanashi, Y., Nishizawa, M., Myajima, N., Kamamoto, T., and Toyoshima, K., *Mol. Cell. Biol.* 7: 41–47, 1987.

Trahey, M., Wong, G., Halenbeck, R., Ruinfeld, B., Martin, G. A., Ladner, M., Long, C. M., Crosier, W. J., Watt, K., Koths, K., and McCormick, F., *Science* 243: 1697–1700, 1988.

Wilks, A. F., *Process in Growth Factor Research* 2: 97–111, 1990.

Wilks, A. F., Harpur, A., Kurban, R. R., Ralph, S. J., Zuercher, G., and Ziemiecki, A. *Molecular and Cellular Biology* 11: 2057–2065, 1991.

Yamamishi, Y., Fukushige, S. I., Semba, K., Sukegawa, J., Miyajima, N., Matsubara, K. I., Yamamoto, T., and toyoshima, K., *Molec. Cell. Biol.* 7: 237–243, 1987.

---

We claim:

1. An isolated mammalian polypeptide comprising an amino acid sequence encoded by a nucleic acid molecule, the complementary sequence of which hybridizes to SEQ ID NO:1 or to SEQ. ID NO:2, at 65° C., 6×SSC, 1% SDS, with a final wash of 0.2×SSC, 0.1% SDS, at 65° C., wherein said polypeptide comprises multiple catalytic domains, but no SH2 domains.

2. The isolated polypeptide of claim 1 wherein the mammalian polypeptide is a human protein or a mouse protein.

3. The isolated mammalian polypeptide of claim 1, further comprising two protein kinase catalytic domains.

4. The isolated mammalian polypeptide of claim 3 having a molecular weight of from about 100,000 daltons to about 200,000 daltons as determined by SDS-PAGE.

5. The isolated mammalian polypeptide of claim 4, having a molecular weight of from about 120,000 daltons to about 150,000 daltons as determined by SDS-PAGE.

6. The isolated mammalian polypeptide of claim 1, wherein said polypeptide consists of the amino acid sequence set forth in SEQ ID NO: 24.

7. The isolated mammalian polypeptide of claim 1, wherein said polypeptide consists of the amino acid sequence set forth in SEQ ID NO: 25.

8. An isolated polypeptide, consisting of an amino acid sequence selected from the group consisting of SEQ ID NO: 4, SEQ ID NO: 11, and SEQ ID NO: 12.

9. An isolated polypeptide consisting of an amino acid sequence selected from the group consisting of amino acids 576-825 of SEQ ID NO: 24; 578-824 of SEQ ID NO: 24, and amino acids 868-1130 of SEQ ID NO: 24.

10. An isolated polypeptide consisting of an amino acid sequence selected from the group consisting of amino acids 425-536 of SEQ ID NO: 24, and amino acids 252-359 of SEQ ID NO: 25.

11. An isolated polypeptide consisting of an amino acid sequence selected from the group consisting of:

(a) amino acids 133-288 of SEQ ID NO: 24;
(b) amino acids 1-141 of SEQ ID NO: 25;
(c) amino acids 302-324 of SEQ ID NO: 24;
(d) amino acids 144-166 of SEQ ID NO: 25;
(e) amino acids 347-468 of SEQ ID NO: 24;
(f) amino acids 179-297 of SEQ ID NO: 25;
(g) amino acids 484-570 of SEQ ID NO: 24;
(h) amino acids 308-395 of SEQ ID NO: 25;
(i) amino acids 571-851 of SEQ ID NO: 24;
(j) amino acids 399-688 of SEQ ID NO: 25;
(k) amino acids 852-1139 of SEQ ID NO: 24; and
(l) amino acids 700-988 of SEQ ID NO: 25.

12. An isolated polypeptide consisting of an amino acid sequence selected from the group consisting of amino acids 399-688 of SEQ ID NO: 25 and amino acids 700-988 of SEQ ID NO: 25.

13. An isolated polypeptide consisting of an amino acid sequence selected from the group consisting of amino acids 571-851 of SEQ ID NO: 24 and 852-1139 of SEQ ID NO: 24.

14. An isolated polypeptide consisting of an amino acid sequence selected from the group consisting of amino acids 420-570 of SEQ ID NO: 24; 249-398 of SEQ ID NO: 25, and 51-151 of SEQ ID NO: 24.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 4234 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 1:

```
TGGCCGCCTA  GCGAGCTGCC  GGTCGACCCC  AGCCAGCCGA  GCGACGGGCG  CTGCCTGGCC        60

CAGGGCACAC  GGAAGTGCGC  TTCTCTGAAG  TAGCTTTGGA  AAGTAGAGAA  GAAAATCCAG       120
```

```
TTTGCTTCTT GGAGAACACT GGACAGCTGA ATAAATGCAG TATCTAAATA TAAAAGAGGA    180
CTGCAATGCC ATGGCTTTCT GTGCTAAAAT GAGGAGCTCC AAGAAGACTG AGGTGAACCT    240
GGAGGCCCCT GAGCCAGGGG TGGAAGTGAT CTTCTATCTG TCGGACAGGG AGCCCCTCCG    300
GCTGGGCAGT GGAGAGTACA CAGCAGAGGA ACTGTGCATC AGGGCTGCAC AGGCATGCCG    360
TATCTCTCCT CTTTGTCACA ACCTCTTTGC CCTGTATGAC GAGAACACCA AGCTCTGGTA    420
TGCTCCAAAT CGCACCATCA CCGTTGATGA CAAGATGTCC CTCCGGCTCC ACTACGGAT     480
GAGGTTCTAT TTCACCAATT GGCATGGAAC CAACGACAAT GAGCAGTCAG TGTGGCGTCA    540
TTCTCCAAAG AAGCAGAAAA ATGGCTACGA GAAAAAAAG ATTCCAGATG CAACCCCTCT     600
CCTTGATGCC AGCTCACTGG AGTATCTGTT TGCTCAGGGA CAGTATGATT TGGTGAAATG    660
CCTGGCTCCT ATTCGAGACC CCAAGACCGA GCAGGATGGA CATGATATTG AGAACGAGTG    720
TCTAGGGATG GCTGTCCTGG CCATCTCACA CTATGCCATG ATGAAGAAGA TGCAGTTGCC    780
AGAACTGCCC AAGGACATCA GCTACAAGCG ATATATTCCA GAAACATTGA ATAAGTCCAT    840
CAGACAGAGG AACCTTCTCA CCAGGATGCG GATAAATAAT GTTTCAAGG ATTTCCTAAA     900
GGAATTTAAC AACAAGACCA TTTGTGACAG CAGCGTGTCC ACGCATGACC TGAAGGTGAA    960
ATACTTGGCT ACCTTGGAAA CTTTGACAAA ACATTACGGT GCTGAAATAT TTGAGACTTC   1020
CATGTTACTG ATTTCATCAG AAAATGAGAT GAATTGGTTT CATTCGAATG ACGGTGGAAA   1080
CGTTCTCTAC TACGAAGTGA TGGTGACTGG GAATCTTGGA ATCCAGTGGA GGCATAAACC   1140
AAATGTTGTT TCTGTTGAAA AGGAAAAAAA TAAACTGAAG CGGAAAAAAC TGGAAAATAA   1200
AGACAAGAAG GATGAGGAGA AAAACAAGAT CCGGGAAGAG TGGAACAATT TTCATTCTT    1260
CCCTGAAATC ACTCACATTG TAATAAAGGA GTCTGTGGTC AGCATTAACA AGCAGGACAA   1320
CAAGAAAATG GAACTGAAGC TCTCTTCCCA CGAGGAGGCC TTGTCCTTTG TGTCCCTGGT   1380
AGATGGCTAC TTCCGGCTCA CAGCAGATGC CCATCATTAC CTCTGCACCG ACGTGGCCCC   1440
CCCGTTGATC GTCCACAACA TACAGAATGG CTGTCATGGT CCAATCTGTA CAGAATACGC   1500
CATCAATAAA TTGCGGCAAG AAGGAAGCGA GGAGGGGATG TACGTGCTGA GGTGGAGCTG   1560
CACCGACTTT GACAACATCC TCATGACCGT CACCTGCTTT GAGAAGTCTG AGCAGGTGCA   1620
GGGTGCCCAG AAGCAGTTCA AGAACTTTCA GATCGAGGTG CAGAAGGGCC GCTACAGTCT   1680
GCACGGTTCG GACCGCAGCT TCCCCAGCTT GGGAGACCTC ATGAGCCACC TCAAGAAGCA   1740
GATCCTGCGC ACGGATAACA TCAGCTTCAT GCTAAAACGC TGCTGCCAGC CCAAGCCCCG   1800
AGAAATCTCC AACCTGCTGG TGGCTACTAA GAAAGCCCAG GAGTGGCAGC CCGTCTACCC   1860
CATGAGCCAG CTGAGTTTCG ATCGGATCCT CAAGAAGGAT CTGGTGCAGG GCGAGCACCT   1920
TGGGAGAGGC ACGAGAACAC ACATCTATTC TGGGACCCTG ATGGATTACA AGGATGACGA   1980
AGGAACTTCT GAAGAGAAGA AGATAAAAGT GATCCTCAAA GTCTTAGACC CCAGCCACAG   2040
GGATATTTCC CTGGCCTTCT TCGAGGCAGC CAGCATGATG AGACAGGTCT CCCACAAACA   2100
CATCGTGTAC CTCTATGGCG TCTGTGTCCG CGACGTGGAG AATATCATGG TGGAAGAGTT   2160
TGTGGAAGGG GGTCCTCTGG ATCTCTTCAT GCACCGGAAA AGTGATGTCC TTACCACACC   2220
ATGGAAATTC AAAGTTGCCA AACAGCTGGC CAGTGCCCTG AGCTACTTGG AGGATAAAGA   2280
CCTGGTCCAT GGAAATGTGT GTACTAAAAA CCTCCTCCTG GCCCGTGAGG GAATCGACAG   2340
TGAGTGTGGC CCATTCATCA AGCTCAGTGA CCCCGGCATC CCCATTACGG TGCTGTCTAG   2400
GCAAGAATGC ATTGAACGAA TCCCATGGAT TGCTCCTGAG TGTGTTGAGG ACTCCAAGAA   2460
CCTGAGTGTG GCTGCTGACA AGTGGAGCTT TGGAACCACG CTCTGGGAAA TCTGCTACAA   2520
```

```
TGGCGAGATC  CCCTTGAAAG  ACAAGACGCT  GATTGAGAAA  GAGAGATTCT  ATGAAAGCCG   2580

GTGCAGGCCA  GTGACACCAT  CATGTAAGGA  GCTGGCTGAC  CTCATGACCC  GCTGCATGAA   2640

CTATGACCCC  AATCAGAGGC  CTTTCTTCCG  AGCCATCATG  AGAGACATTA  ATAAGCTTGA   2700

AGAGCAGAAT  CCAGATATTG  TTTCCAGAAA  AAAAAACCAG  CCAACTGAAG  TGGACCCCAC   2760

ACATTTGAG   AAGCGCTTCC  TAAAGAGGAT  CCGTGACTTG  GGAGAGGGCC  ACTTTGGGAA   2820

GGTTGAGCTC  TGCAGGTATG  ACCCCGAAGA  CAATACAGGG  GAGCAGGTGG  CTGTTAAATC   2880

TCTGAAGCCT  GAGAGTGGAG  GTAACCACAT  AGCTGATCTG  AAAAAGGAAA  TCGAGATCTT   2940

AAGGAACCTC  TATCATGAGA  ACATTGTGAA  GTACAAAGGA  ATCTGCACAG  AAGACGGAGG   3000

AAATGGTATT  AAGCTCATCA  TGGAATTTCT  GCCTTCGGGA  AGCCTTAAGG  AATATCTTCC   3060

AAAGAATAAG  AACAAAATAA  ACCTCAAACA  GCAGCTAAAA  TATGCCGTTC  AGATTTGTAA   3120

GGGGATGGAC  TATTTGGGTT  CTCGGCAATA  CGTTCACCGG  GACTTGGCAG  CAAGAAATGT   3180

CCTTGTTGAG  AGTGAACACC  AAGTGAAAAT  TGGAGACTTC  GGTTAACCA   AAGCAATTGA   3240

AACCGATAAG  GAGTATTACA  CCGTCAAGGA  TGACCGGGAC  AGCCCTGTGT  TTTGGTATGC   3300

TCCAGAATGT  TTAATGCAAT  CTAAATTTTA  TATTGCCTCT  GACGTCTGGT  CTTTTGGAGT   3360

CACTCTGCAT  GAGCTGCTGA  CTTACTGTGA  TTCAGATTCT  AGTCCCATGG  CTTTGTTCCT   3420

GAAAATGATA  GGCCCAACCC  ATGGCCAGAT  GACAGTCACA  AGACTTGTGA  ATACGTTAAA   3480

AGAAGGAAAA  CGCCTGCCGT  GCCCACCTAA  CTGTCCAGAT  GAGGTTTATC  AGCTTATGAG   3540

AAAATGCTGG  GAATTCCAAC  CATCCAATCG  GACAAGCTTT  CAGAACCTTA  TTGAAGGATT   3600

TGAAGCACTT  TTAAAATAAG  AAGCATGAAT  AACATTTAAA  TTCCACAGAT  TATCAAGTCC   3660

TTCTCCTGCA  ACAAATGCCC  AAGTCATTTT  TTAAAAATTT  CTAATGAAAG  AAGTTTGTGT   3720

TCTGTCCAAA  AAGTCACTGA  ACTCATACTT  CAGTACATAT  ACATGTATAA  GGCACACTGT   3780

AGTGCTTAAT  ATGTGTAAGG  ACTTCCTCTT  TAAATTTGCA  CCAGTAACTT  AGTGACACAT   3840

AATGACAACC  AAAATATTTG  AAAGCACTTA  AGCACTCCTC  CTTGTGGAAA  GAATATACCA   3900

CCATTTCATC  TGGCTAGTTC  ACCATCACAA  CTGCATTACC  AAAAGGGGAT  TTTTGAAAAC   3960

GAGGAGTTGA  CCAAAATAAT  ATCTGAAGAT  GATTGCTTTT  CCCTGCTGCC  AGCTGACTGA   4020

AATGTTTTCC  TGGCACATTA  ATCATAGATA  AAGAAGATTG  ATGGACTTAG  CCCTCAAACA   4080

GTATCTATAC  AGTACTAGAC  CATGCATTCT  TAAAATATTA  GATACCAGGT  AGTATATATT   4140

GTTTCTGTAC  AAAAATGACT  GTATTCTCTC  ACCAGTAGGA  CTTAAACTTT  GTTTCTCCAG   4200

TGGCTTAGCT  CCTGTTCCTT  TGGGTGATCA  CTAG                                4234
```

(2) INFORMATION FOR SEQ ID NO:2:

(i) SEQUENCE CHARACTERISTICS:
        (A) LENGTH: 3495 base pairs
        (B) TYPE: nucleic acid
        (D) STRANDEDNESS: single
        (D) TOPOLOGY: linear (ii) MOLECULE TYPE: nucleic acid (xi) SEQUENCE DESCRIPTION: SEQ ID NO: 2:

```
CTGCTTGATG  ACTTTGTCAT  GTCTTACCTT  TCCCCTCAGT  GGCGGCATGA  TTTTGTTCAC    60

GGATGGATAA  AAGTACCTGT  GACTCATGAA  ACTCAGGAAG  AGTGTCTTGG  GATGGCGGTG   120

TTAGACATGA  TGAGAATAGC  TAAGGAGAAA  GACCAGACTC  CACTGGCTGT  CTATAACTCT   180

GTCAGCTACA  AGACATTCTT  ACCAAAGTGC  GTTCGAGCGA  AGATCCAAGA  CTATCACATT   240
```

```
TTAACCCGGA  AGCGAATCAG  GTACAGATTT  CGCAGATTCA  TTCAGCAATT  CAGTCAATGT   300
AAAGCCACTG  CCAGGAACCT  AAAACTTAAG  TATCTTATAA  ACCTGGAAAC  CCTGCAGTCT   360
GCCTTCTACA  CAGAACAGTT  TGAAGTAAAA  GAATCTGCAA  GAGGTCCTTC  AGGTGAGGAG   420
ATTTTTGCAA  CCATTATAAT  AACTGGAAAC  GGTGGAATTC  AGTGGTCAAG  AGGGAAACAT   480
AAGGAAAGTG  AGACACTGAC  AGAACAGGAC  GTACAGTTAT  ATTGTGATTT  CCCTGATATT   540
ATTGATGTCA  GTATTAAGCA  AGCAAATCAG  GAATGCTCAA  CTGAAAGTAG  AGTTGTGACC   600
GTCCACAAGC  AGGACGGGAA  GGTCTTGGAA  ATAGAACTTA  GCTCATTAAA  AGAAGCCTTG   660
TCATTCGTGT  CATTAATTGA  CGGGTATTAC  AGACTAACTG  CGGATGCACA  CCATTACCTC   720
TGCAAAGAGG  TGGCTCCCCC  AGCTGTGTTC  GAGAACATAC  ACAGCAACTG  CCACGGCCCA   780
ATTCAATGG   ATTTGCCAT   CAGCAAACTA  AAGAAGGCAG  GAAACCAGAC  TGGACTGTAT   840
GTACTTCGAT  GTAGCCCTAA  GGACTTCAAC  AAATACTTCC  TGACCTTTGC  CGTTGAGCGA   900
GAAAATGTTA  TTGAATATAA  ACACTGTTTG  ATTACAAAGA  ATGAGAATGG  AGAGTACAAC   960
CTCAGTGGGA  CTAAGAGGAA  CTTCAGTAGT  CTTAAGGACC  TTTTGAATTG  CTACCAGATG  1020
GAAACTGTGC  GCTCAGACAG  TATCATCTTC  CAGTTCACCA  AATGCTGTCC  TCCAAAGCCG  1080
AAAGATAAAT  CAAACCTTCT  TGTCTTCAGA  ACAAATGGTG  TTTCTGATGT  TCAGCTCTCA  1140
CCAACATTAC  AGAGGCATAA  TAATGTGAAT  CAAATGGTGT  TCACAAAAT   CAGGAATGAA  1200
GATTTGATAT  TTAATGAAAG  CCTTGGCCAA  GGCACTTTTA  CAAAAATATT  TAAAGGTGTA  1260
AGAAGAGAAG  TTGGAGATTA  TGGTCAGCTG  CACGAAACCG  AAGTTCTTTT  GAAAGTCCTA  1320
GATAAAGCAC  ATAGAAACTA  TTCAGAGTCT  TTCTTTGAAG  CAGCAAGCAT  GATGAGTCAG  1380
CTTTCTCACA  AGCATTTGGT  TTTGAATTAT  GGAGTATGTG  TCTGTGGAGA  GGAGAACATT  1440
TTGGTTCAAG  AGTTTGTAAA  ATTTGGATCA  CTGGATACAT  ACCTGAAGAA  GAACAAAAAT  1500
TCTATAAATA  TATTATGGAA  ACTTGGAGTG  GCGAAGCAGT  GGCATGGGC   CATGCACTTC  1560
CTCGAAGAAA  AATCCCTTAT  TCATGGGAAT  GTGTGTGCTA  AAAATATCCT  GCTTATCAGA  1620
GAAGAAGACA  GGAGAACGGG  GAACCCACCT  TTCATCAAAC  TTAGTGATCC  TGGCATTAGC  1680
ATTACAGTTC  TACCGAAGGA  CATTTCTTCC  TGTTGTTTCC  AAGTTCTTCA  GGAGAGAATA  1740
CCATGGGTAC  CACCTGAGTG  CATTGAGAAT  CCTAAAAATC  TAACTCTGGC  AACAGACAAG  1800
TGGAGCTTCG  GGACCACTCT  GTGGGAGATC  TGCAGTGGAG  GAGATAAGCC  CCTGAGTGCT  1860
CTGGATTCTC  AAAGAAAGCT  GCAGTTCTAT  GAAGATAAGC  ATCAGCTTCC  TGCACCCAAG  1920
TGGACAGAGT  TGGCAAACCT  TATAAATAAT  TGCATGGACT  ATGAGCCAGA  TTTCAGGCCT  1980
GCTTTCAGAG  CTGTCATCCG  TGATCTTAAC  AGCCTGTTTA  CTCCAGATTA  TGAACTACTA  2040
ACAGAAAATG  ACATGCTACC  AAACATGAGA  ATAGGTGCCC  TAGGGTTTTC  TGGTGCTTTT  2100
GAAGACAGGG  ACCCTACACA  GTTTGAAGAG  AGACACTTGA  AGTTTCTACA  GCAGCTTGGC  2160
AAAGGTAACT  TCGGGAGTGT  GGAGATGTGC  CGCTATGACC  CGCTGCAGGA  CAACACTGGC  2220
GAGGTGGTCG  CTGTGAAGAA  ACTCCAGCAC  AGCACTGAAG  AGCACCTCCG  AGACTTTGAG  2280
AGGGAGATCG  AGATCCTGAA  ATCCTTGCAG  CATGACAACA  TCGTCAAGTA  CAAGGGAGTG  2340
TGCTACAGTG  CGGGTCGGCG  CAACCTAAGA  TTAATTATGG  AATATTTACC  ATATGGAAGT  2400
TTACGAGACT  ATCTCCAAAA  ACATAAAGAA  CGGATAGATC  ACAAAAAACT  TCTTCAATAC  2460
ACATCTCAGA  TATGCAAGGG  CATGGAATAT  CTTGGTACAA  AAAGGTATAT  CCACAGGGAC  2520
CTGGCAACAA  GGAACATATT  GGTGGAAAAT  GAGAACAGGG  TTAAAATAGG  AGACTTCGGA  2580
TTAACCAAAG  TCTTGCCGCA  GGACAAAGAA  TACTACAAAG  TAAAGGAGCC  AGGGGAAAGC  2640
```

-continued

```
CCCATATTCT  GGTACGCACC  TGAATCCTTG  ACGGAGAGCA  AGTTTTCTGT  GGCCTCAGAT    2700
GTGTGGAGCT  TTGGAGTGGT  TCTATACGAA  CTTTTCACAT  ACATCGAGAA  GAGTAAAAGT    2760
CCACCCGTGG  AATTTATGCG  AATGATTGGC  AATGATAAAC  AAGGGCAAAT  GATTGTGTTC    2820
CATTTGATAG  AGCTACTGAA  GAGCAACGGA  AGATTGCCAA  GGCCAGAAGG  ATGCCCAGAT    2880
GAGATTTATG  TGATCATGAC  AGAGTGCTGG  AACAACAATG  TGAGCCAGCG  TCCCTCCTTC    2940
AGGGACCTTT  CCTTCGGGTG  GATCAAATCC  GGGACAGTAT  AGCTGCGTGA  AAGAGATGGC    3000
CTTACTCAGA  GACCAAGCAG  ACTTCCAGAA  CCAGAACAAA  GCTCTGTAGC  CTTGTGTCTA    3060
CACATCCTTA  TCATGACGCT  AGCTAGGCAG  AAAGAAAACT  GTGACGCCGT  CTGCTCAAAA    3120
GCTTTGGAAA  ACGCCGTGCA  GGTTTGTTTC  ATCACCATCT  GTAAAAACCA  CTGCTCAAGT    3180
CTGGCAGCAT  GCTTGTGGGC  TGATGCATGG  AGCTCACCAC  AGAGTCTCTG  CATCTCCTCT    3240
GACAGAAGAA  GAAAAATAGA  CAATTTTCAA  CTCACTTTTT  TGAGAAATGG  AAAAAAATTA    3300
TAATGTAAAT  TTTTCAGTGT  AGGAAATACA  CAGAACATAC  ATGTACAGTT  TTTACCACGT    3360
GGAGTGTATA  ATACTTTGGC  CTCTTGTGTG  ATTTACATGA  GGGCTGATGT  TTGTTAATGT    3420
TTTCTAATTT  TTCCATAGGT  GATCTATAAT  AACTTCATGA  TACAAATTAA  AATGCTCAGA    3480
AAATTAAAAA  AAAAA                                                          3495
```

( 2 ) INFORMATION FOR SEQ ID NO:3:

( i ) SEQUENCE CHARACTERISTICS:
        ( A ) LENGTH: 6 amino acid residues
        ( B ) TYPE: amino acid
        ( D ) TOPOLOGY: linear ( i x ) FEATURE:
        ( D ) OTHER INFORMATION: Xaa in positions 2, 4 and 5 is unknow ( x i ) SEQUENCE DESCRIPTION: SEQ ID NO: 3:

Gly Xaa Gly Xaa Xaa Gly
           5

( 2 ) INFORMATION FOR SEQ ID NO:4:

( i ) SEQUENCE CHARACTERISTICS:
        ( A ) LENGTH: 16 amino acid residues
        ( B ) TYPE: amino acid
        ( D ) TOPOLOGY: linear ( x i ) SEQUENCE DESCRIPTION: SEQ ID NO: 4:

Thr Ser Phe Gln Asn Leu Ile Glu Cys Phe Glu Ala Leu Leu Lys Cys
           5                    10                   15

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TACACCTTTA AATATTTTTG T                                        21

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CTCGAGTCGA CGAATTC 17

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CTTGCTTAAT ACTGACATCA 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CTTGCTTAAT ACTGACATCA 20

( 2 ) INFORMATION FOR SEQ ID NO:9:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

TAAATGCAG 9

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GCCATGGCT 9

( 2 ) INFORMATION FOR SEQ ID NO:11:

( i ) SEQUENCE CHARACTERISTICS:
        ( A ) LENGTH: 8 amino acid residues
        ( B ) TYPE: amino acid
        ( D ) TOPOLOGY: linear ( x i ) SEQUENCE DESCRIPTION: SEQ ID NO: 11:

Gly Leu Tyr Val Leu Arg Trp Ser
                5

( 2 ) INFORMATION FOR SEQ ID NO:12:

( i ) SEQUENCE CHARACTERISTICS:
        ( A ) LENGTH: 7 amino acid residues
        ( B ) TYPE: amino acid
        ( D ) TOPOLOGY: linear ( x i ) SEQUENCE DESCRIPTION: SEQ ID NO: 12:

```
Val Asp Gly Tyr Phe Arg Ile
                  5
```

(2) INFORMATION FOR SEQ ID NO: 13:

(i) SEQUENCE CHARACTERISTICS:
        (A) LENGTH: 47 amino acids
        (B) TYPE: amino acid
        (D) TOPOLOGY: linear (xi) SEQUENCE DESCRIPTION: SEQ ID NO: 13:

```
Lys Ile Gly Glu Gly Thr Tyr Gly Val Val Tyr Lys Gly Arg His
                 5                  10                  15

Lys Thr Thr Gly Gln Val Val Ala Met Lys Lys Ile Arg Leu Glu
                20                  25                  30

Ser Glu Glu Glu Gly Val Pro Ser Thr Ala Ile Arg Glu Ile Ser
                35                  40                  45

Leu Leu
```

(2) INFORMATION FOR SEQ ID NO: 14:

(i) SEQUENCE CHARACTERISTICS:
        (A) LENGTH: 82 amino acids
        (B) TYPE: amino acid
        (D) TOPOLOGY: linear (xi) SEQUENCE DESCRIPTION: SEQ ID NO: 14:

```
Val Phe Cys His Ser Arg Arg Val Leu His Arg Asp Leu Lys Pro
                 5                  10                  15

Gln Asn Leu Leu Ile Asp Asp Lys Gly Thr Ile Lys Leu Ala Asp
                20                  25                  30

Phe Gly Leu Ala Arg Ala Phe Gly Ile Pro Ile Arg Val Tyr Thr
                35                  40                  45

His Glu Val Val Thr Leu Trp Tyr Arg Ser Pro Glu Val Leu Leu
                50                  55                  60

Gly Ser Ala Arg Tyr Ser Thr Pro Val Asp Ile Trp Ser Ile Gly
                65                  70                  75

Thr Ile Phe Ala Glu Leu Ala
                80
```

(2) INFORMATION FOR SEQ ID NO: 15:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO: 15:

```
Leu Ala Ser His His Val Lys Asn Leu Asp Glu Asn Gly Leu Asp
                 5                  10                  15

Leu Leu Ser Lys Met Leu Ile Tyr Asp Pro Ala Lys Arg Ile Ser
                20                  25                  30
```

(2) INFORMATION FOR SEQ ID NO: 16:

(i) SEQUENCE CHARACTERISTICS:
        (A) LENGTH: 601 amino acids
        (B) TYPE: amino acid
        (D) TOPOLOGY: linear (xi) SEQUENCE DESCRIPTION: SEQ ID NO: 16:

```
Val Phe His Lys Ile Arg Asn Glu Asp Leu Ile Phe Asn Glu Ser
                 5                  10                  15
```

```
Leu Gly Gln Gly Thr Phe Thr Lys Ile Phe Lys Gly Val Arg Arg
             20                  25                  30

Glu Val Gly Asp Tyr Gly Gln Leu His Glu Thr Glu Val Leu Leu
             35                  40                  45

Lys Val Leu Asp Lys Ala His Arg Asn Tyr Ser Glu Ser Phe Phe
             50                  55                  60

Glu Ala Ala Ser Met Met Ser Gln Leu Ser His Lys His Leu Val
             65                  70                  75

Leu Asn Tyr Gly Val Cys Val Cys Gly Glu Glu Asn Ile Leu Val
             80                  85                  90

Gln Glu Phe Val Lys Phe Gly Ser Leu Asp Thr Tyr Leu Lys Lys
             95                 100                 105

Asn Lys Asn Ser Ile Asn Ile Leu Trp Lys Leu Gly Val Ala Lys
            110                 115                 120

Gln Leu Ala Trp Ala Met His Phe Leu Glu Glu Lys Ser Leu Ile
            125                 130                 135

His Gly Asn Val Cys Ala Lys Asn Ile Leu Leu Ile Arg Glu Glu
            140                 145                 150

Asp Arg Arg Thr Gly Asn Pro Pro Phe Ile Lys Leu Ser Asp Pro
            155                 160                 165

Gly Ile Ser Ile Thr Val Leu Pro Lys Asp Ile Ser Ser Cys Cys
            170                 175                 180

Phe Gln Val Leu Gln Glu Arg Ile Pro Trp Val Pro Pro Glu Cys
            185                 190                 195

Ile Glu Asn Pro Lys Asn Leu Thr Leu Ala Thr Asp Lys Trp Ser
            200                 205                 210

Phe Gly Thr Thr Leu Trp Glu Ile Cys Ser Gly Gly Asp Lys Pro
            215                 220                 225

Leu Ser Ala Leu Asp Ser Gln Arg Lys Leu Gln Phe Tyr Glu Asp
            230                 235                 240

Lys His Gln Leu Pro Ala Pro Lys Trp Thr Glu Leu Ala Asn Leu
            245                 250                 255

Ile Asn Asn Cys Met Asp Tyr Glu Pro Asp Phe Arg Pro Ala Phe
            260                 265                 270

Arg Ala Val Ile Arg Asp Leu Asn Ser Leu Phe Thr Pro Asp Tyr
            275                 280                 285

Glu Leu Leu Thr Glu Asn Asp Met Leu Pro Asn Met Arg Ile Gly
            290                 295                 300

Ala Leu Gly Phe Ser Gly Ala Phe Glu Asp Arg Asp Pro Thr Gln
            305                 310                 315

Phe Glu Glu Arg His Leu Lys Phe Leu Gln Gln Leu Gly Lys Gly
            320                 325                 330

Asn Phe Gly Ser Val Glu Met Cys Arg Tyr Asp Pro Leu Gln Asp
            335                 340                 345

Asn Thr Gly Glu Val Val Ala Val Lys Lys Leu Gln His Ser Thr
            350                 355                 360

Glu Glu His Leu Arg Asp Phe Glu Arg Glu Ile Glu Ile Leu Lys
            365                 370                 375

Ser Leu Gln His Asp Asn Ile Val Lys Tyr Lys Gly Val Cys Tyr
            380                 385                 390

Ser Ala Gly Arg Arg Asn Leu Arg Leu Ile Met Glu Tyr Leu Pro
            395                 400                 405

Tyr Gly Ser Leu Arg Asp Tyr Leu Gln Lys His Lys Glu Arg Ile
```

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 410 |     |     |     |     | 415 |     |     |     |     | 420 |
| Asp | His | Lys | Lys | Leu | Leu | Gln | Tyr | Thr | Ser | Gln | Ile | Cys | Lys | Gly |
|     |     |     |     | 425 |     |     |     |     | 430 |     |     |     |     | 435 |
| Met | Glu | Tyr | Leu | Gly | Thr | Lys | Arg | Tyr | Ile | His | Arg | Asp | Leu | Ala |
|     |     |     |     | 440 |     |     |     |     | 445 |     |     |     |     | 450 |
| Thr | Arg | Asn | Ile | Leu | Val | Glu | Asn | Glu | Asn | Arg | Val | Lys | Ile | Gly |
|     |     |     |     | 455 |     |     |     |     | 460 |     |     |     |     | 465 |
| Asp | Phe | Gly | Leu | Thr | Lys | Val | Leu | Pro | Gln | Asp | Lys | Glu | Tyr | Tyr |
|     |     |     |     | 470 |     |     |     |     | 475 |     |     |     |     | 480 |
| Lys | Val | Lys | Glu | Pro | Gly | Glu | Ser | Pro | Ile | Phe | Trp | Tyr | Ala | Pro |
|     |     |     |     | 485 |     |     |     |     | 490 |     |     |     |     | 495 |
| Glu | Ser | Leu | Thr | Glu | Ser | Lys | Phe | Ser | Val | Ala | Ser | Asp | Val | Trp |
|     |     |     |     | 500 |     |     |     |     | 505 |     |     |     |     | 510 |
| Ser | Phe | Gly | Val | Val | Leu | Tyr | Glu | Leu | Phe | Thr | Tyr | Ile | Glu | Lys |
|     |     |     |     | 515 |     |     |     |     | 520 |     |     |     |     | 525 |
| Ser | Lys | Ser | Pro | Pro | Val | Glu | Phe | Met | Arg | Met | Ile | Gly | Asn | Asp |
|     |     |     |     | 530 |     |     |     |     | 535 |     |     |     |     | 540 |
| Lys | Gln | Gly | Gln | Met | Ile | Val | Phe | His | Leu | Ile | Glu | Leu | Leu | Lys |
|     |     |     |     | 545 |     |     |     |     | 550 |     |     |     |     | 555 |
| Ser | Asn | Gly | Arg | Leu | Pro | Arg | Pro | Glu | Gly | Cys | Pro | Asp | Glu | Ile |
|     |     |     |     | 560 |     |     |     |     | 565 |     |     |     |     | 570 |
| Tyr | Val | Ile | Met | Thr | Glu | Cys | Trp | Asn | Asn | Asn | Val | Ser | Gln | Arg |
|     |     |     |     | 575 |     |     |     |     | 580 |     |     |     |     | 585 |
| Pro | Ser | Phe | Arg | Asp | Leu | Ser | Phe | Gly | Trp | Ile | Lys | Ser | Gly | Thr |
|     |     |     |     | 590 |     |     |     |     | 595 |     |     |     |     | 600 |
| Val |     |     |     |     |     |     |     |     |     |     |     |     |     |     |

( 2 ) INFORMATION FOR SEQ ID NO: 17:

( i ) SEQUENCE CHARACTERISTICS:
        ( A ) LENGTH: 581 amino acids
        ( B ) TYPE: amino acid
        ( D ) TOPOLOGY: linear ( x i ) SEQUENCE DESCRIPTION: SEQ ID NO: 17:

|     |     |     |     |     |     |     |     |     |     |     |     |     |     |     |
|-----|-----|-----|-----|-----|-----|-----|-----|-----|-----|-----|-----|-----|-----|-----|
| Ser | Phe | Asp | Arg | Ile | Leu | Lys | Lys | Asp | Leu | Val | Gln | Gly | Glu | His |
|     |     |     |     | 5   |     |     |     |     | 10  |     |     |     |     | 15  |
| Leu | Gly | Arg | Gly | Thr | Arg | Thr | His | Ile | Tyr | Ser | Gly | Thr | Leu | Met |
|     |     |     |     | 20  |     |     |     |     | 25  |     |     |     |     | 30  |
| Asp | Tyr | Lys | Asp | Asp | Glu | Gly | Thr | Ser | Glu | Glu | Lys | Lys | Ile | Lys |
|     |     |     |     | 35  |     |     |     |     | 40  |     |     |     |     | 45  |
| Val | Ile | Leu | Lys | Val | Leu | Asp | Pro | Ser | His | Arg | Asp | Ile | Ser | Leu |
|     |     |     |     | 50  |     |     |     |     | 55  |     |     |     |     | 60  |
| Ala | Phe | Phe | Glu | Ala | Ala | Ser | Met | Met | Arg | Gln | Val | Ser | His | Lys |
|     |     |     |     | 65  |     |     |     |     | 70  |     |     |     |     | 75  |
| His | Ile | Val | Tyr | Leu | Tyr | Gly | Val | Cys | Val | Arg | Asp | Val | Glu | Asn |
|     |     |     |     | 80  |     |     |     |     | 85  |     |     |     |     | 90  |
| Ile | Met | Val | Glu | Glu | Phe | Val | Glu | Gly | Gly | Pro | Leu | Asp | Leu | Phe |
|     |     |     |     | 95  |     |     |     |     | 100 |     |     |     |     | 105 |
| Met | His | Arg | Lys | Ser | Asp | Val | Leu | Thr | Thr | Pro | Trp | Lys | Phe | Lys |
|     |     |     |     | 110 |     |     |     |     | 115 |     |     |     |     | 120 |
| Val | Ala | Lys | Gln | Leu | Ala | Ser | Ala | Leu | Ser | Tyr | Leu | Glu | Asp | Lys |
|     |     |     |     | 125 |     |     |     |     | 130 |     |     |     |     | 135 |
| Asp | Leu | Val | His | Gly | Asn | Val | Cys | Thr | Lys | Asn | Leu | Leu | Leu | Ala |
|     |     |     |     | 140 |     |     |     |     | 145 |     |     |     |     | 150 |

-continued

| | | | | | | | | | | | | | | |
|---|---|---|---|---|---|---|---|---|---|---|---|---|---|---|
| Arg | Glu | Gly | Ile | Asp 155 | Ser | Glu | Cys | Gly | Pro 160 | Phe | Ile | Lys | Leu | Ser 165 |
| Asp | Pro | Gly | Ile | Pro 170 | Ile | Thr | Val | Leu | Ser 175 | Arg | Gln | Glu | Cys | Ile 180 |
| Glu | Arg | Ile | Pro | Trp 185 | Ile | Ala | Pro | Glu | Cys 190 | Val | Glu | Asp | Ser | Lys 195 |
| Asn | Leu | Ser | Val | Ala 200 | Ala | Asp | Lys | Trp | Ser 205 | Phe | Gly | Thr | Thr | Leu 210 |
| Trp | Glu | Ile | Cys | Tyr 215 | Asn | Gly | Glu | Ile | Pro 220 | Leu | Lys | Asp | Lys | Thr 225 |
| Leu | Ile | Glu | Lys | Glu 230 | Arg | Phe | Tyr | Glu | Ser 235 | Arg | Cys | Arg | Pro | Val 240 |
| Thr | Pro | Ser | Cys | Lys 245 | Glu | Leu | Ala | Asp | Leu 250 | Met | Thr | Arg | Cys | Met 255 |
| Asn | Tyr | Asp | Pro | Asn 260 | Gln | Arg | Pro | Phe | Phe 265 | Arg | Ala | Ile | Met | Arg 270 |
| Asp | Ile | Asn | Lys | Leu 275 | Glu | Glu | Gln | Asn | Pro 280 | Asp | Ile | Val | Ser | Arg 285 |
| Lys | Lys | Asn | Gln | Pro 290 | Thr | Glu | Val | Asp | Pro 295 | Thr | His | Phe | Thr | Lys 300 |
| Arg | Phe | Leu | Lys | Arg 305 | Ile | Arg | Asp | Leu | Gly 310 | Glu | Gly | His | Phe | Gly 315 |
| Lys | Val | Glu | Leu | Cys 320 | Arg | Tyr | Asp | Pro | Glu 325 | Asp | Asn | Thr | Gly | Glu 330 |
| Gln | Val | Ala | Val | Lys 335 | Ser | Leu | Lys | Pro | Glu 340 | Ser | Gly | Gly | Asn | His 345 |
| Ile | Ala | Asp | Leu | Lys 350 | Lys | Glu | Ile | Glu | Ile 355 | Leu | Arg | Asn | Leu | Tyr 360 |
| His | Glu | Asn | Ile | Val 365 | Lys | Tyr | Lys | Gly | Ile 370 | Cys | Thr | Glu | Asp | Gly 375 |
| Gly | Asn | Gly | Ile | Lys 380 | Leu | Ile | Met | Glu | Phe 385 | Leu | Pro | Ser | Gly | Ser 390 |
| Leu | Lys | Glu | Tyr | Leu 395 | Pro | Lys | Asn | Lys | Asn 400 | Lys | Ile | Asn | Leu | Lys 405 |
| Gln | Gln | Leu | Lys | Tyr 410 | Ala | Val | Gln | Ile | Cys 415 | Lys | Gly | Met | Asp | Tyr 420 |
| Leu | Gly | Ser | Arg | Gln 425 | Tyr | Val | His | Arg | Asp 430 | Leu | Ala | Ala | Arg | Asn 435 |
| Val | Leu | Val | Glu | Ser 440 | Glu | His | Gln | Val | Lys 445 | Ile | Gly | Asp | Phe | Gly 450 |
| Leu | Thr | Lys | Ala | Ile 455 | Glu | Thr | Asp | Lys | Glu 460 | Tyr | Tyr | Thr | Val | Lys 465 |
| Asp | Asp | Arg | Asp | Ser 470 | Pro | Val | Phe | Trp | Tyr 475 | Ala | Pro | Glu | Cys | Leu 480 |
| Met | Gln | Ser | Lys | Phe 485 | Tyr | Ile | Ala | Ser | Asp 490 | Val | Trp | Ser | Phe | Gly 495 |
| Val | Thr | Leu | His | Glu 500 | Leu | Leu | Thr | Tyr | Cys 505 | Asp | Ser | Asp | Ser | Ser 510 |
| Pro | Met | Ala | Leu | Phe 515 | Leu | Lys | Met | Ile | Gly 520 | Pro | Thr | His | Gly | Gln 525 |
| Met | Thr | Val | Thr | Arg 530 | Leu | Val | Asn | Thr | Leu 535 | Lys | Glu | Gly | Lys | Arg 540 |
| Leu | Pro | Cys | Pro | Pro 545 | Asn | Cys | Pro | Asp | Glu 550 | Val | Tyr | Gln | Leu | Met 555 |

```
Arg  Lys  Cys  Trp  Glu  Phe  Gln  Pro  Ser  Asn  Arg  Thr  Ser  Phe  Gln
                    560                 565                      570

Asn  Leu  Ile  Glu  Gly  Phe  Glu  Ala  Leu  Leu  Lys
                    575                 580
```

( 2 ) INFORMATION FOR SEQ ID NO: 18:

( i ) SEQUENCE CHARACTERISTICS:
  ( A ) LENGTH: 1132 amino acids
  ( B ) TYPE: amino acid
  ( D ) TOPOLOGY: linear ( x i ) SEQUENCE DESCRIPTION: SEQ ID NO: 18:

```
Met  Gln  Tyr  Leu  Asn  Ile  Lys  Glu  Asp  Cys  Asn  Ala  Met  Ala  Phe
                    5                   10                       15

Cys  Ala  Lys  Met  Arg  Ser  Ser  Lys  Lys  Thr  Glu  Val  Asn  Leu  Glu
                    20                  25                       30

Ala  Pro  Glu  Pro  Gly  Val  Glu  Val  Ile  Phe  Tyr  Leu  Ser  Asp  Arg
                    35                  40                       45

Glu  Pro  Leu  Arg  Leu  Gly  Ser  Gly  Glu  Tyr  Thr  Ala  Glu  Glu  Leu
                    50                  55                       60

Cys  Ile  Arg  Ala  Ala  Gln  Ala  Cys  Arg  Ile  Ser  Pro  Leu  Cys  His
                    65                  70                       75

Asn  Leu  Phe  Ala  Leu  Tyr  Asp  Glu  Asn  Thr  Lys  Leu  Trp  Tyr  Ala
                    80                  85                       90

Pro  Asn  Arg  Thr  Ile  Thr  Val  Asp  Asp  Lys  Met  Ser  Leu  Arg  Leu
                    95                  100                      105

His  Tyr  Arg  Met  Arg  Phe  Tyr  Phe  Thr  Asn  Trp  His  Gly  Thr  Asn
                    110                 115                      120

Asp  Asn  Glu  Gln  Ser  Val  Trp  Arg  His  Ser  Pro  Lys  Lys  Gln  Lys
                    125                 130                      135

Asn  Gly  Tyr  Glu  Lys  Lys  Lys  Ile  Pro  Asp  Ala  Thr  Pro  Leu  Leu
                    140                 145                      150

Asp  Ala  Ser  Ser  Leu  Glu  Tyr  Leu  Phe  Ala  Gln  Gly  Gln  Tyr  Asp
                    155                 160                      165

Leu  Val  Lys  Cys  Leu  Ala  Pro  Ile  Arg  Asp  Pro  Lys  Thr  Glu  Gln
                    170                 175                      180

Asp  Gly  His  Asp  Ile  Glu  Asn  Glu  Cys  Leu  Gly  Met  Ala  Val  Leu
                    185                 190                      195

Ala  Ile  Ser  His  Tyr  Ala  Met  Met  Lys  Lys  Met  Gln  Leu  Pro  Glu
                    200                 205                      210

Leu  Pro  Lys  Asp  Ile  Ser  Tyr  Lys  Arg  Tyr  Ile  Pro  Glu  Thr  Leu
                    215                 220                      225

Asn  Lys  Ser  Ile  Arg  Gln  Arg  Asn  Leu  Leu  Thr  Arg  Met  Arg  Ile
                    230                 235                      240

Asn  Asn  Val  Phe  Lys  Asp  Phe  Leu  Lys  Glu  Phe  Asn  Asn  Lys  Thr
                    245                 250                      255

Ile  Cys  Asp  Ser  Ser  Val  Ser  Thr  His  Asp  Leu  Lys  Val  Lys  Tyr
                    260                 265                      270

Leu  Ala  Thr  Leu  Glu  Thr  Leu  Thr  Lys  His  Tyr  Gly  Ala  Glu  Ile
                    275                 280                      285

Phe  Glu  Thr  Ser  Met  Leu  Leu  Ile  Ser  Ser  Glu  Asn  Glu  Met  Asn
                    290                 295                      300

Trp  Phe  His  Ser  Asn  Asp  Gly  Gly  Asn  Val  Leu  Tyr  Tyr  Glu  Val
                    305                 310                      315
```

```
Met Val Thr Gly Asn Leu Gly Ile Gln Trp Arg His Lys Pro Asn
            320                     325                     330
Val Val Ser Val Glu Lys Glu Lys Asn Lys Leu Lys Arg Lys Lys
            335                     340                     345
Leu Glu Asn Lys Asp Lys Lys Asp Glu Glu Lys Asn Lys Ile Arg
            350                     355                     360
Glu Glu Trp Asn Asn Phe Ser Phe Phe Pro Glu Ile Thr His Ile
            365                     370                     375
Val Ile Lys Glu Ser Val Val Ser Ile Asn Lys Gln Asp Asn Lys
            380                     385                     390
Lys Met Glu Leu Lys Leu Ser Ser His Glu Glu Ala Leu Ser Phe
            395                     400                     405
Val Ser Leu Val Asp Gly Tyr Phe Arg Leu Thr Ala Asp Ala His
            410                     415                     420
His Tyr Leu Cys Thr Asp Val Ala Pro Pro Leu Ile Val His Asn
            425                     430                     435
Ile Gln Asn Gly Cys His Gly Pro Ile Cys Glu Tyr Ala Ile Asn
            440                     445                     450
Lys Leu Arg Gln Glu Gly Ser Glu Glu Gly Met Tyr Val Leu Arg
            455                     460                     465
Trp Ser Cys Thr Asp Phe Asp Asn Ile Leu Met Thr Val Thr Cys
            470                     475                     480
Phe Glu Lys Ser Glu Gln Val Gln Gly Ala Gln Lys Gln Phe Lys
            485                     490                     495
Asn Phe Gln Ile Glu Val Gln Lys Gly Arg Tyr Ser Leu His Gly
            500                     505                     510
Ser Asp Arg Ser Phe Pro Ser Leu Gly Asp Leu Met Ser His Leu
            515                     520                     525
Lys Lys Gln Ile Leu Arg Thr Asp Asn Ile Ser Phe Met Leu Lys
            530                     535                     540
Arg Cys Cys Gln Pro Lys Pro Arg Glu Ile Ser Asn Leu Leu Val
            545                     550                     555
Ala Thr Lys Lys Ala Gln Glu Trp Gln Pro Val Tyr Pro Met Ser
            560                     565                     570
Gln Leu Ser Phe Asp Arg Ile Leu Lys Lys Asp Leu Val Gln Gly
            575                     580                     585
Glu His Leu Gly Arg Gly Thr Arg Thr His Ile Tyr Ser Gly Thr
            590                     595                     600
Leu Met Asp Tyr Lys Asp Asp Glu Gly Thr Ser Glu Glu Lys Lys
            605                     610                     615
Ile Lys Val Ile Leu Lys Val Leu Asp Pro Ser His Arg Asp Ile
            620                     625                     630
Ser Leu Ala Phe Phe Glu Ala Ala Ser Met Met Arg Gln Val Ser
            635                     640                     645
His Lys His Ile Val Tyr Leu Tyr Gly Val Cys Val Arg Asp Val
            650                     655                     660
Glu Asn Ile Met Val Glu Glu Phe Val Glu Gly Gly Pro Leu Asp
            665                     670                     675
Leu Phe Met His Arg Lys Ser Asp Val Leu Thr Thr Pro Trp Lys
            680                     685                     690
Phe Lys Val Ala Lys Gln Leu Ala Ser Ala Leu Ser Tyr Leu Glu
            695                     700                     705
Asp Lys Asp Leu Val His Gly Asn Val Cys Thr Lys Asn Leu Leu
            710                     715                     720
```

-continued

| | | | | | | | | | | | | |
|---|---|---|---|---|---|---|---|---|---|---|---|---|
|Leu|Ala|Arg|Glu|Gly|Ile|Asp|Ser|Glu|Cys|Gly|Pro|Phe|Ile|Lys|
| | | | |725| | | |730| | | |735|
|Leu|Ser|Asp|Pro|Gly|Ile|Pro|Ile|Thr|Val|Leu|Ser|Arg|Gln|Glu|
| | | | |740| | | |745| | | |750|
|Cys|Ile|Glu|Arg|Ile|Pro|Trp|Ile|Ala|Pro|Glu|Cys|Val|Glu|Asp|
| | | | |755| | | |760| | | |765|
|Ser|Lys|Asn|Leu|Ser|Val|Ala|Ala|Asp|Lys|Trp|Ser|Phe|Gly|Thr|
| | | | |770| | | |775| | | |780|
|Thr|Leu|Trp|Glu|Ile|Cys|Tyr|Asn|Gly|Glu|Ile|Pro|Leu|Lys|Asp|
| | | | |785| | | |790| | | |795|
|Lys|Thr|Leu|Ile|Glu|Lys|Glu|Arg|Phe|Tyr|Glu|Ser|Arg|Cys|Arg|
| | | | |800| | | |805| | | |810|
|Pro|Val|Thr|Pro|Ser|Cys|Lys|Glu|Leu|Ala|Asp|Leu|Met|Thr|Arg|
| | | | |815| | | |820| | | |825|
|Cys|Met|Asn|Tyr|Asp|Pro|Asn|Gln|Arg|Pro|Phe|Phe|Arg|Ala|Ile|
| | | | |830| | | |835| | | |840|
|Met|Arg|Asp|Ile|Asn|Lys|Leu|Glu|Glu|Gln|Asn|Pro|Asp|Ile|Val|
| | | | |845| | | |850| | | |855|
|Ser|Arg|Lys|Lys|Asn|Gln|Pro|Thr|Glu|Val|Asp|Pro|Thr|His|Phe|
| | | | |860| | | |865| | | |870|
|Lys|Arg|Phe|Leu|Lys|Arg|Ile|Arg|Asp|Leu|Gly|Glu|Gly|His|Phe|
| | | | |875| | | |880| | | |885|
|Gly|Lys|Val|Glu|Leu|Cys|Arg|Tyr|Asp|Pro|Glu|Asp|Asn|Thr|Gly|
| | | | |890| | | |895| | | |900|
|Glu|Gln|Val|Ala|Val|Lys|Ser|Leu|Lys|Pro|Glu|Ser|Gly|Gly|Asn|
| | | | |905| | | |910| | | |915|
|His|Ile|Ala|Asp|Leu|Lys|Lys|Glu|Ile|Glu|Ile|Leu|Arg|Asn|Leu|
| | | | |920| | | |925| | | |930|
|Tyr|His|Glu|Asn|Ile|Val|Lys|Tyr|Lys|Gly|Ile|Cys|Thr|Glu|Asp|
| | | | |935| | | |940| | | |945|
|Gly|Gly|Asn|Gly|Ile|Lys|Leu|Ile|Met|Glu|Phe|Leu|Pro|Ser|Gly|
| | | | |950| | | |955| | | |960|
|Ser|Leu|Lys|Glu|Tyr|Leu|Pro|Lys|Asn|Lys|Asn|Lys|Ile|Asn|Leu|
| | | | |965| | | |970| | | |975|
|Lys|Gln|Gln|Leu|Lys|Tyr|Ala|Val|Gln|Ile|Cys|Lys|Gly|Met|Asp|
| | | | |980| | | |985| | | |990|
|Tyr|Leu|Gly|Ser|Arg|Gln|Tyr|Val|His|Arg|Asp|Leu|Ala|Ala|Arg|
| | | | |995| | | |1000| | | |1005|
|Asn|Val|Leu|Val|Glu|Ser|Glu|His|Gln|Val|Lys|Ile|Gly|Asp|Phe|
| | | | |1010| | | |1015| | | |1020|
|Gly|Leu|Thr|Lys|Ala|Ile|Glu|Thr|Asp|Lys|Glu|Tyr|Tyr|Thr|Val|
| | | | |1025| | | |1030| | | |1035|
|Lys|Asp|Asp|Arg|Asp|Ser|Pro|Val|Phe|Trp|Tyr|Ala|Pro|Glu|Cys|
| | | | |1040| | | |1045| | | |1050|
|Leu|Met|Gln|Ser|Lys|Phe|Tyr|Ile|Ala|Ser|Asp|Val|Trp|Ser|Phe|
| | | | |1055| | | |1060| | | |1065|
|Gly|Val|Thr|Leu|His|Glu|Leu|Leu|Thr|Tyr|Cys|Asp|Ser|Asp|Ser|
| | | | |1070| | | |1075| | | |1080|
|Ser|Pro|Met|Ala|Leu|Phe|Leu|Lys|Met|Ile|Gly|Pro|Thr|His|Gly|
| | | | |1085| | | |1090| | | |1095|
|Gln|Met|Thr|Val|Thr|Arg|Leu|Val|Asn|Thr|Leu|Lys|Glu|Gly|Lys|
| | | | |1100| | | |1105| | | |1110|
|Arg|Leu|Pro|Cys|Pro|Pro|Asn|Cys|Pro|Asp|Glu|Val|Tyr|Gln|Leu|

Met Arg Lys Cys Trp Glu Phe
1130

(2) INFORMATION FOR SEQ ID NO: 19:

(i) SEQUENCE CHARACTERISTICS:
(A) LENGTH: 971 amino acids
(B) TYPE: amino acid
(D) TOPOLOGY: linear (xi) SEQUENCE DESCRIPTION: SEQ ID NO: 19:

| | | | | | | | | | | | | | | |
|---|---|---|---|---|---|---|---|---|---|---|---|---|---|---|
| Leu | Leu | Asp | Asp | Phe | Val | Met | Ser | Tyr | Leu | Ser | Pro | Gln | Trp | Arg |
| | | | | 5 | | | | | 10 | | | | | 15 |
| His | Asp | Phe | Val | His | Gly | Trp | Ile | Lys | Val | Pro | Val | Thr | His | Glu |
| | | | | 20 | | | | | 25 | | | | | 30 |
| Thr | Gln | Glu | Glu | Cys | Leu | Gly | Met | Ala | Val | Leu | Asp | Met | Met | Arg |
| | | | | 35 | | | | | 40 | | | | | 45 |
| Ile | Ala | Lys | Glu | Lys | Asp | Gln | Thr | Pro | Leu | Ala | Val | Tyr | Asn | Ser |
| | | | | 50 | | | | | 55 | | | | | 60 |
| Val | Ser | Tyr | Lys | Thr | Phe | Leu | Pro | Lys | Cys | Val | Arg | Ala | Lys | Ile |
| | | | | 65 | | | | | 70 | | | | | 75 |
| Gln | Asp | Tyr | His | Ile | Leu | Thr | Arg | Lys | Arg | Ile | Arg | Tyr | Arg | Phe |
| | | | | 80 | | | | | 85 | | | | | 90 |
| Arg | Arg | Phe | Ile | Gln | Gln | Phe | Ser | Gln | Cys | Lys | Ala | Thr | Ala | Arg |
| | | | | 95 | | | | | 100 | | | | | 105 |
| Asn | Leu | Lys | Leu | Lys | Tyr | Leu | Ile | Asn | Leu | Glu | Thr | Leu | Gln | Ser |
| | | | | 110 | | | | | 115 | | | | | 120 |
| Ala | Phe | Tyr | Thr | Glu | Gln | Phe | Glu | Val | Lys | Glu | Ser | Ala | Arg | Gly |
| | | | | 125 | | | | | 130 | | | | | 135 |
| Pro | Ser | Gly | Glu | Glu | Ile | Phe | Ala | Thr | Ile | Ile | Ile | Thr | Gly | Asn |
| | | | | 140 | | | | | 145 | | | | | 150 |
| Gly | Gly | Ile | Gln | Trp | Ser | Arg | Gly | Lys | His | Lys | Glu | Ser | Glu | Thr |
| | | | | 155 | | | | | 160 | | | | | 165 |
| Leu | Thr | Glu | Gln | Asp | Leu | Gln | Leu | Tyr | Cys | Asp | Phe | Pro | Asp | Ile |
| | | | | 170 | | | | | 175 | | | | | 180 |
| Ile | Asp | Val | Ser | Ile | Lys | Gln | Ala | Asn | Gln | Glu | Cys | Ser | Thr | Glu |
| | | | | 185 | | | | | 190 | | | | | 195 |
| Ser | Arg | Ile | Val | Thr | Val | His | Lys | Gln | Asp | Gly | Glu | Val | Leu | Glu |
| | | | | 200 | | | | | 205 | | | | | 210 |
| Ile | Glu | Leu | Ser | Ser | Leu | Lys | Glu | Ala | Leu | Ser | Phe | Val | Ser | Leu |
| | | | | 215 | | | | | 220 | | | | | 225 |
| Ile | Asp | Gly | Tyr | Tyr | Arg | Leu | Thr | Ala | Asp | Ala | His | His | Tyr | Leu |
| | | | | 230 | | | | | 235 | | | | | 240 |
| Cys | Lys | Glu | Val | Ala | Pro | Pro | Ala | Val | Leu | Glu | Asn | Ile | His | Ser |
| | | | | 245 | | | | | 250 | | | | | 255 |
| Asn | Cys | His | Gly | Pro | Ile | Ser | Met | Asp | Phe | Ala | Ile | Ser | Lys | Leu |
| | | | | 260 | | | | | 265 | | | | | 270 |
| Lys | Lys | Ala | Gly | Asn | Gln | Thr | Gly | Leu | Tyr | Val | Leu | Arg | Cys | Ser |
| | | | | 275 | | | | | 280 | | | | | 285 |
| Pro | Lys | Asp | Phe | Asn | Lys | Tyr | Phe | Leu | Thr | Phe | Ala | Val | Glu | Arg |
| | | | | 290 | | | | | 295 | | | | | 300 |
| Glu | Asn | Val | Ile | Glu | Tyr | Lys | His | Cys | Leu | Ile | Thr | Lys | Asn | Glu |
| | | | | 305 | | | | | 310 | | | | | 315 |
| Asn | Gly | Glu | Tyr | Asn | Leu | Ser | Gly | Thr | Lys | Arg | Asn | Phe | Ser | Ser |
| | | | | 320 | | | | | 325 | | | | | 330 |

-continued

| | | | | | | | | | | | | | | |
|---|---|---|---|---|---|---|---|---|---|---|---|---|---|---|
| Leu | Lys | Asp | Leu | Leu 335 | Asn | Cys | Tyr | Gln | Met 340 | Glu | Thr | Val | Arg | Ser 345 |
| Asp | Ser | Ile | Ile | Phe 350 | Gln | Phe | Thr | Lys | Cys 355 | Cys | Pro | Pro | Lys | Pro 360 |
| Lys | Asp | Lys | Ser | Asn 365 | Leu | Leu | Val | Phe | Arg 370 | Thr | Asn | Gly | Val | Ser 375 |
| Asp | Val | Gln | Leu | Ser 380 | Pro | Thr | Leu | Gln | Arg 385 | His | Asn | Asn | Val | Asn 390 |
| Gln | Met | Val | Phe | His 395 | Lys | Ile | Arg | Asn | Glu 400 | Asp | Leu | Ile | Phe | Asn 405 |
| Glu | Ser | Leu | Gly | Gln 410 | Gly | Thr | Phe | Thr | Lys 415 | Ile | Phe | Lys | Gly | Val 420 |
| Arg | Arg | Glu | Val | Gly 425 | Asp | Tyr | Gly | Gln | Leu 430 | His | Glu | Thr | Glu | Val 435 |
| Leu | Leu | Lys | Val | Leu 440 | Asp | Lys | Ala | His | Arg 445 | Asn | Tyr | Ser | Glu | Ser 450 |
| Phe | Phe | Glu | Ala | Ala 455 | Ser | Met | Met | Ser | Gln 460 | Leu | Ser | His | Lys | His 465 |
| Leu | Val | Leu | Asn | Tyr 470 | Gly | Val | Cys | Val | Cys 475 | Gly | Glu | Glu | Asn | Ile 480 |
| Leu | Val | Gln | Glu | Phe 485 | Val | Lys | Phe | Gly | Ser 490 | Leu | Asp | Thr | Tyr | Leu 495 |
| Lys | Lys | Asn | Lys | Asn 500 | Ser | Ile | Asn | Ile | Leu 505 | Trp | Lys | Leu | Gly | Val 510 |
| Ala | Lys | Gln | Leu | Ala 515 | Trp | Ala | Met | His | Phe 520 | Leu | Glu | Glu | Lys | Ser 525 |
| Leu | Ile | His | Gly | Asn 530 | Val | Cys | Ala | Lys | Asn 535 | Ile | Leu | Leu | Ile | Arg 540 |
| Glu | Glu | Asp | Arg | Arg 545 | Thr | Gly | Asn | Pro | Phe 550 | Ile | Lys | Leu | Ser | Asp 555 |
| Pro | Gly | Ile | Ser | Ile 560 | Thr | Val | Leu | Pro | Lys 565 | Asp | Ile | Ser | Ser | Cys 570 |
| Cys | Phe | Gln | Val | Leu 575 | Gln | Glu | Arg | Ile | Pro 580 | Trp | Val | Pro | Pro | Glu 585 |
| Cys | Ile | Glu | Asn | Pro 590 | Lys | Asn | Leu | Thr | Leu 595 | Ala | Thr | Asp | Lys | Trp 600 |
| Ser | Phe | Gly | Thr | Thr 605 | Leu | Trp | Glu | Ile | Cys 610 | Ser | Gly | Gly | Asp | Lys 615 |
| Pro | Leu | Ser | Ala | Leu 620 | Asp | Ser | Gln | Arg | Lys 625 | Leu | Gln | Phe | Tyr | Glu 630 |
| Asp | Lys | His | Gln | Leu 635 | Pro | Ala | Pro | Lys | Trp 640 | Thr | Glu | Leu | Ala | Asn 645 |
| Leu | Ile | Asn | Asn | Cys 650 | Met | Asp | Tyr | Glu | Pro 655 | Asp | Phe | Arg | Pro | Ala 660 |
| Phe | Arg | Ala | Val | Ile 665 | Arg | Asp | Leu | Asn | Ser 670 | Leu | Phe | Thr | Pro | Asp 675 |
| Tyr | Glu | Leu | Leu | Thr 680 | Glu | Asn | Asp | Met | Leu 685 | Pro | Asn | Met | Arg | Ile 690 |
| Gly | Ala | Leu | Gly | Phe 695 | Ser | Gly | Ala | Phe | Glu 700 | Asp | Arg | Asp | Pro | Thr 705 |
| Gln | Phe | Glu | Glu | Arg 710 | His | Leu | Lys | Phe | Leu 715 | Gln | Gln | Leu | Gly | Lys 720 |
| Gly | Asn | Phe | Gly | Ser | Val | Glu | Met | Cys | Arg | Tyr | Asp | Pro | Leu | Gln |

|     |     |     |     | 725 |     |     |     |     | 730 |     |     |     |     | 735 |
| --- | --- | --- | --- | --- | --- | --- | --- | --- | --- | --- | --- | --- | --- | --- |
| Asp | Asn | Thr | Gly | Glu | Val | Val | Ala | Val | Lys | Lys | Leu | Gln | His | Ser |
|     |     |     |     | 740 |     |     |     |     | 745 |     |     |     |     | 750 |
| Thr | Glu | Glu | His | Leu | Arg | Asp | Phe | Glu | Arg | Glu | Ile | Glu | Ile | Leu |
|     |     |     |     | 755 |     |     |     |     | 760 |     |     |     |     | 765 |
| Lys | Ser | Leu | Gln | His | Asp | Asn | Ile | Val | Lys | Tyr | Lys | Gly | Val | Cys |
|     |     |     |     | 770 |     |     |     |     | 775 |     |     |     |     | 780 |
| Tyr | Ser | Ala | Gly | Arg | Arg | Asn | Leu | Arg | Leu | Ile | Met | Glu | Tyr | Leu |
|     |     |     |     | 785 |     |     |     |     | 790 |     |     |     |     | 795 |
| Pro | Tyr | Gly | Ser | Leu | Arg | Asp | Tyr | Leu | Gln | Lys | His | Lys | Glu | Arg |
|     |     |     |     | 800 |     |     |     |     | 805 |     |     |     |     | 810 |
| Ile | Asp | His | Lys | Lys | Leu | Leu | Gln | Tyr | Thr | Ser | Gln | Ile | Cys | Lys |
|     |     |     |     | 815 |     |     |     |     | 820 |     |     |     |     | 825 |
| Gly | Met | Glu | Tyr | Leu | Gly | Thr | Lys | Arg | Tyr | Ile | His | Arg | Asp | Leu |
|     |     |     |     | 830 |     |     |     |     | 835 |     |     |     |     | 840 |
| Ala | Thr | Arg | Asn | Ile | Leu | Val | Glu | Asn | Glu | Asn | Arg | Val | Lys | Ile |
|     |     |     |     | 845 |     |     |     |     | 850 |     |     |     |     | 855 |
| Gly | Asp | Phe | Gly | Leu | Thr | Lys | Val | Leu | Pro | Gln | Asp | Lys | Glu | Tyr |
|     |     |     |     | 860 |     |     |     |     | 865 |     |     |     |     | 870 |
| Tyr | Lys | Val | Lys | Glu | Pro | Gly | Glu | Ser | Pro | Ile | Phe | Trp | Tyr | Ala |
|     |     |     |     | 875 |     |     |     |     | 880 |     |     |     |     | 885 |
| Pro | Glu | Ser | Leu | Thr | Glu | Ser | Lys | Phe | Ser | Val | Ala | Ser | Asp | Val |
|     |     |     |     | 890 |     |     |     |     | 895 |     |     |     |     | 900 |
| Trp | Ser | Phe | Gly | Val | Val | Leu | Tyr | Glu | Leu | Phe | Thr | Tyr | Ile | Glu |
|     |     |     |     | 905 |     |     |     |     | 910 |     |     |     |     | 915 |
| Lys | Ser | Lys | Ser | Pro | Pro | Val | Glu | Phe | Met | Arg | Met | Ile | Gly | Asn |
|     |     |     |     | 920 |     |     |     |     | 925 |     |     |     |     | 930 |
| Asp | Lys | Gln | Gly | Gln | Met | Ile | Val | Phe | His | Leu | Ile | Glu | Leu | Leu |
|     |     |     |     | 935 |     |     |     |     | 940 |     |     |     |     | 945 |
| Lys | Ser | Asn | Gly | Arg | Leu | Pro | Arg | Pro | Glu | Gly | Cys | Pro | Asp | Glu |
|     |     |     |     | 950 |     |     |     |     | 955 |     |     |     |     | 960 |
| Ile | Tyr | Val | Ile | Met | Thr | Glu | Cys | Trp | Asn | Asn |     |     |     |     |
|     |     |     |     | 965 |     |     |     |     | 970 |     |     |     |     |     |

( 2 ) INFORMATION FOR SEQ ID NO:20:

( i ) SEQUENCE CHARACTERISTICS:
    ( A ) LENGTH: 1184 amino acids
    ( B ) TYPE: amino acid
    ( D ) TOPOLOGY: linear ( x i ) SEQUENCE DESCRIPTION: SEQ ID NO:20:

|     |     |     |     |     |     |     |     |     |     |     |     |     |     |     |
| --- | --- | --- | --- | --- | --- | --- | --- | --- | --- | --- | --- | --- | --- | --- |
| Met | Pro | Leu | Arg | His | Trp | Gly | Met | Ala | Arg | Gly | Ser | Lys | Pro | Val |
|     |     |     |     | 5   |     |     |     |     | 10  |     |     |     |     | 15  |
| Gly | Asp | Gly | Ala | Gln | Pro | Met | Ala | Ala | Met | Gly | Gly | Leu | Lys | Val |
|     |     |     |     | 20  |     |     |     |     | 25  |     |     |     |     | 30  |
| Leu | Leu | His | Trp | Ala | Gly | Pro | Gly | Gly | Glu | Pro | Trp | Val | Thr |     |
|     |     |     |     | 35  |     |     |     |     | 40  |     |     |     |     | 45  |
| Phe | Ser | Glu | Ser | Ser | Leu | Ile | Ala | Glu | Glu | Val | Cys | Ile | His | Ile |
|     |     |     |     | 50  |     |     |     |     | 55  |     |     |     |     | 60  |
| Ala | His | Lys | Val | Gly | Ile | Thr | Pro | Pro | Cys | Phe | Asn | Leu | Phe | Ala |
|     |     |     |     | 65  |     |     |     |     | 70  |     |     |     |     | 75  |
| Leu | Phe | Asp | Ala | Gln | Ala | Gln | Val | Trp | Leu | Pro | Pro | Asn | His | Ile |
|     |     |     |     | 80  |     |     |     |     | 85  |     |     |     |     | 90  |
| Leu | Glu | Ile | Pro | Arg | Asp | Ala | Ser | Leu | Met | Leu | Tyr | Phe | Arg | Ile |
|     |     |     |     | 95  |     |     |     |     | 100 |     |     |     |     | 105 |

```
Arg Phe Tyr Phe Arg Asn Trp His Gly Met Asn Pro Arg Glu Pro
            110                 115                 120
Ala Gly Tyr Arg Cys Gly Pro Pro Gly Thr Glu Ala Ser Ser Asp
            125                 130                 135
Gln Thr Ala Gln Gly Met Gln Leu Leu Asp Pro Ala Ser Phe Glu
            140                 145                 150
Tyr Leu Phe Glu Gln Gly Lys His Glu Phe Glu Asn Asp Val Ala
            155                 160                 165
Ser Leu Trp Glu Leu Ser Thr Glu Glu Ile His His Phe Lys
            170                 175                 180
Asn Glu Ser Leu Gly Met Ala Phe Leu His Leu Cys His Leu Ala
            185                 190                 195
Leu Arg His Gly Ile Pro Leu Glu Glu Val Ala Lys Lys Thr Ser
            200                 205                 210
Phe Lys Asp Cys Ile Pro Arg Ser Phe Arg Arg His Ile Arg Gln
            215                 220                 225
His Ser Ala Leu Thr Arg Leu Arg Leu Arg Asn Val Phe Arg Arg
            230                 235                 240
Phe Leu Arg Asp Phe Gln Pro Gly Arg Leu Ser Gln Gln Met Val
            245                 250                 255
Met Val Lys Tyr Leu Ala Thr Leu Glu Arg Leu Ala Pro Arg Phe
            260                 265                 270
Gly Thr Glu Arg Val Pro Val Cys His Leu Arg Leu Leu Ala Gln
            275                 280                 285
Ala Glu Gly Glu Pro Cys Tyr Ile Arg Asp Ser Gly Val Ala Pro
            290                 295                 300
Thr Asp Pro Gly Pro Glu Ser Ala Ala Gly Pro Pro Thr His Glu
            305                 310                 315
Val Leu Val Thr Gly Thr Gly Gly Ile Gln Trp Trp Pro Val Glu
            320                 325                 330
Glu Glu Val Asn Lys Glu Glu Gly Ser Ser Gly Ser Ser Ala Arg
            335                 340                 345
Asn Pro Gln Ala Ser Leu Phe Gly Lys Lys Ala Lys Ala His Lys
            350                 355                 360
Ala Phe Gly Gln Pro Ala Asp Arg Pro Arg Glu Pro Leu Trp Ala
            365                 370                 375
Tyr Phe Cys Asp Ile Thr His Val Val Leu Lys Glu His Cys Val
            380                 385                 390
Ser Ile His Arg Gln Asp Asn Lys Cys Leu Glu Leu Ser Leu Pro
            395                 400                 405
Ser Arg Ala Ala Ala Leu Ser Phe Glu Ser Leu Val Asp Gly Tyr
            410                 415                 420
Phe Arg Leu Thr Ala Asp Ser Ser His Tyr Leu Cys His Glu Val
            425                 430                 435
Ala Pro Pro Arg Leu Val Met Ser Ile Arg Asp Gly Ile His Gly
            440                 445                 450
Pro Leu Leu Glu Pro Phe Val Gln Gln Ala Lys Leu Arg Pro Leu
            455                 460                 465
Glu Asp Gly Leu Tyr Leu Ile His Trp Ser Thr Ser His Pro Tyr
            470                 475                 480
Arg Leu Ile Leu Thr Val Ala Gln Arg Ser Gln Ala Pro Asp Gly
            485                 490                 495
Met Gln Ser Leu Arg Leu Arg Lys Phe Pro Ile Glu Gln Gln Asp
```

|     |     |     |     | 500 |     |     |     |     | 505 |     |     |     |     | 510 |
| --- | --- | --- | --- | --- | --- | --- | --- | --- | --- | --- | --- | --- | --- | --- |
| Gly | Ala | Phe | Val | Leu | Glu | Gly | Trp | Gly | Arg | Ser | Phe | Pro | Ser | Val |
|     |     |     |     | 515 |     |     |     |     | 520 |     |     |     |     | 525 |
| Arg | Glu | Leu | Gly | Ala | Ala | Leu | Gln | Gly | Cys | Leu | Leu | Arg | Ala | Gly |
|     |     |     |     | 530 |     |     |     |     | 535 |     |     |     |     | 540 |
| Asp | Asp | Cys | Phe | Ser | Leu | Arg | Arg | Cys | Cys | Leu | Pro | Gln | Pro | Gly |
|     |     |     |     | 545 |     |     |     |     | 550 |     |     |     |     | 555 |
| Glu | Thr | Ser | Asn | Leu | Ile | Ile | Met | Arg | Gly | Ala | Arg | Ala | Ser | Pro |
|     |     |     |     | 560 |     |     |     |     | 565 |     |     |     |     | 570 |
| Arg | Thr | Leu | Asn | Leu | Ser | Gln | Leu | Ser | Phe | His | Arg | Val | Asp | Gln |
|     |     |     |     | 575 |     |     |     |     | 580 |     |     |     |     | 585 |
| Lys | Glu | Ile | Thr | Gln | Leu | Ser | His | Leu | Gly | Gln | Gly | Thr | Arg | Thr |
|     |     |     |     | 590 |     |     |     |     | 595 |     |     |     |     | 600 |
| Asn | Val | Tyr | Glu | Gly | Arg | Leu | Arg | Val | Glu | Gly | Ser | Gly | Asp | Pro |
|     |     |     |     | 605 |     |     |     |     | 610 |     |     |     |     | 615 |
| Glu | Glu | Gly | Lys | Met | Asp | Asp | Glu | Asp | Pro | Leu | Val | Pro | Gly | Arg |
|     |     |     |     | 620 |     |     |     |     | 625 |     |     |     |     | 630 |
| Asp | Arg | Gly | Gln | Glu | Leu | Arg | Val | Val | Leu | Lys | Val | Leu | Asp | Pro |
|     |     |     |     | 635 |     |     |     |     | 640 |     |     |     |     | 645 |
| Ser | His | His | Asp | Ile | Ala | Leu | Ala | Phe | Tyr | Glu | Thr | Ala | Ser | Leu |
|     |     |     |     | 650 |     |     |     |     | 655 |     |     |     |     | 660 |
| Met | Ser | Gln | Val | Ser | His | Thr | His | Leu | Ala | Phe | Val | His | Gly | Val |
|     |     |     |     | 665 |     |     |     |     | 670 |     |     |     |     | 675 |
| Cys | Val | Arg | Gly | Pro | Glu | Asn | Ser | Met | Val | Thr | Glu | Tyr | Val | Glu |
|     |     |     |     | 680 |     |     |     |     | 685 |     |     |     |     | 690 |
| His | Gly | Pro | Leu | Asp | Val | Trp | Leu | Arg | Arg | Glu | Arg | Gly | His | Val |
|     |     |     |     | 695 |     |     |     |     | 700 |     |     |     |     | 705 |
| Pro | Met | Ala | Trp | Lys | Met | Val | Val | Ala | Gln | Gln | Leu | Ala | Ser | Ala |
|     |     |     |     | 710 |     |     |     |     | 715 |     |     |     |     | 720 |
| Leu | Ser | Tyr | Leu | Glu | Asn | Lys | Asn | Leu | Val | His | Gly | Asn | Val | Cys |
|     |     |     |     | 725 |     |     |     |     | 730 |     |     |     |     | 735 |
| Gly | Arg | Asn | Ile | Leu | Leu | Ala | Arg | Leu | Gly | Leu | Ala | Glu | Gly | Thr |
|     |     |     |     | 740 |     |     |     |     | 745 |     |     |     |     | 750 |
| Ser | Pro | Phe | Ile | Lys | Leu | Ser | Asp | Pro | Gly | Cys | Gly | Leu | Gly | Ala |
|     |     |     |     | 755 |     |     |     |     | 760 |     |     |     |     | 765 |
| Leu | Ser | Arg | Glu | Glu | Arg | Val | Glu | Arg | Ile | Pro | Trp | Leu | Ala | Pro |
|     |     |     |     | 770 |     |     |     |     | 775 |     |     |     |     | 780 |
| Glu | Cys | Leu | Pro | Gly | Gly | Ala | Asn | Ser | Leu | Ser | Thr | Ala | Met | Asp |
|     |     |     |     | 785 |     |     |     |     | 790 |     |     |     |     | 795 |
| Lys | Trp | Gly | Phe | Gly | Ala | Thr | Leu | Leu | Glu | Ile | Cys | Phe | Asp | Gly |
|     |     |     |     | 800 |     |     |     |     | 805 |     |     |     |     | 810 |
| Glu | Ala | Pro | Leu | Gln | Ser | Arg | Ser | Pro | Ser | Glu | Lys | Glu | His | Phe |
|     |     |     |     | 815 |     |     |     |     | 820 |     |     |     |     | 825 |
| Tyr | Gln | Arg | Gln | His | Arg | Leu | Pro | Glu | Pro | Ser | Cys | Pro | Gln | Leu |
|     |     |     |     | 830 |     |     |     |     | 835 |     |     |     |     | 840 |
| Ala | Thr | Leu | Thr | Ser | Gln | Cys | Leu | Thr | Tyr | Glu | Pro | Thr | Gln | Arg |
|     |     |     |     | 845 |     |     |     |     | 850 |     |     |     |     | 855 |
| Pro | Ser | Phe | Ala | Thr | Ile | Leu | Arg | Asp | Leu | Thr | Arg | Val | Gln | Pro |
|     |     |     |     | 860 |     |     |     |     | 865 |     |     |     |     | 870 |
| His | Asn | Leu | Ala | Asp | Val | Leu | Thr | Val | Asn | Arg | Asp | Ser | Pro | Ala |
|     |     |     |     | 875 |     |     |     |     | 880 |     |     |     |     | 885 |
| Val | Gly | Pro | Thr | Thr | Phe | His | Lys | Arg | Tyr | Leu | Lys | Lys | Ile | Arg |
|     |     |     |     | 890 |     |     |     |     | 895 |     |     |     |     | 900 |

```
Asp Leu Gly Glu Gly His Phe Gly Lys Val Ser Leu Tyr Cys Tyr
            905                 910                 915

Asp Pro Thr Asn Asp Gly Thr Gly Glu Met Val Ala Val Lys Ala
            920                 925                 930

Leu Lys Ala Asp Cys Gly Pro Gln His Arg Ser Gly Trp Lys Gln
            935                 940                 945

Glu Ile Asp Ile Leu Arg Thr Leu Tyr His Glu His Ile Ile Lys
            950                 955                 960

Tyr Lys Gly Cys Cys Glu Asp Gln Gly Glu Lys Ser Leu Val Met
            965                 970                 975

Glu Tyr Val Pro Leu Gly Ser Leu Arg Asp Tyr Leu Pro Arg His
            980                 985                 990

Ser Ile Gly Leu Ala Gln Leu Leu Leu Phe Ala Gln Gln Ile Cys
            995                 1000                1005

Glu Gly Met Ala Tyr Leu His Ala His Asp Tyr Ile His Arg Asp
            1010                1015                1020

Leu Ala Ala Arg Asn Val Leu Leu Asp Asn Asp Arg Leu Val Lys
            1025                1030                1035

Ile Gly Asp Phe Gly Leu Ala Lys Ala Val Pro Glu Gly His Glu
            1040                1045                1050

Tyr Tyr Arg Val Arg Glu Asp Gly Asp Ser Pro Val Phe Trp Tyr
            1055                1060                1065

Ala Pro Glu Cys Leu Lys Glu Tyr Asn Phe Tyr Tyr Ala Ser Asp
            1070                1075                1080

Val Trp Ser Phe Gly Val Thr Leu Tyr Glu Leu Leu Thr His Cys
            1085                1090                1095

Asp Ser Ser Gln Ser Pro Pro Thr Lys Phe Leu Glu Leu Ile Gly
            1100                1105                1110

Ile Ala Gln Gly Gln Met Thr Val Leu Arg Leu Thr Glu Leu Leu
            1115                1120                1125

Glu Arg Gly Glu Arg Leu Pro Arg Pro Asp Lys Cys Pro Cys Glu
            1130                1135                1140

Val Tyr His Leu Met Lys Asn Cys Trp Glu Thr Glu Ala Ser Phe
            1145                1150                1155

Arg Pro Thr Phe Glu Asn Ser Ile Pro Ile Leu Lys Thr Val His
            1160                1165                1170

Glu Lys Tyr Gln Gly Gln Ala Pro Ser Val Ser Ser Val Cys
            1175                1180
```

( 2 ) INFORMATION FOR SEQ ID NO:21:

( i ) SEQUENCE CHARACTERISTICS:
        ( A ) LENGTH: 92 amino acids
        ( B ) TYPE: amino acid
        ( D ) TOPOLOGY: linear ( x i ) SEQUENCE DESCRIPTION: SEQ ID NO:21:

```
Trp Tyr His Gly Lys Leu Asp Arg Thr Ile Ala Glu Glu Arg Leu
            5                   10                  15

Arg Gln Ala Gly Lys Ser Gly Ser Tyr Leu Ile Arg Glu Ser Asp
            20                  25                  30

Arg Arg Pro Gly Ser Phe Val Leu Ser Phe Leu Ser Gln Thr Asn
            35                  40                  45

Val Val Asn His Phe Arg Ile Ile Ala Met Cys Gly Asp Tyr Tyr
            50                  55                  60

Ile Gly Gly Arg Arg Phe Ser Ser Leu Ser Asp Leu Ile Gly Tyr
```

|   |   |   | 65 |   |   |   |   | 70 |   |   |   |   | 75 |
|---|---|---|---|---|---|---|---|---|---|---|---|---|---|

Tyr Ser His Val Ser Cys Leu Leu Lys Gly Glu Lys Leu Leu Tyr
                    80                  85                    90
Pro Val ( 2 ) INFORMATION FOR SEQ ID NO:22:

( i ) SEQUENCE CHARACTERISTICS:
        ( A ) LENGTH: 91 amino acids
        ( B ) TYPE: amino acid
        ( D ) TOPOLOGY: linear ( x i ) SEQUENCE DESCRIPTION: SEQ ID NO:22:

Trp Phe His Gly Lys Ile Ser Lys Gln Glu Ala Tyr Asn Leu Leu
                 5              10                    15
Met Thr Val Gly Gln Ala Cys Ser Phe Leu Val Arg Pro Ser Asp
                20                  25                    30
Asn Thr Pro Gly Asp Tyr Ser Leu Tyr Phe Arg Thr Ser Glu Asn
                35                  40                    45
Ile Gln Arg Phe Lys Ile Cys Pro Thr Pro Asn Asn Gln Phe Met
                50                  55                    60
Met Gly Gly Arg Tyr Tyr Asn Ser Ile Gly Asp Ile Ile Asp His
                65                  70                    75
Tyr Arg Lys Glu Gln Ile Val Glu Gly Tyr Tyr Leu Lys Glu Pro
                80                  85                    90
Val ( 2 ) INFORMATION FOR SEQ ID NO: 23:

( i ) SEQUENCE CHARACTERISTICS:
        ( A ) LENGTH: 89 amino acids
        ( B ) TYPE: amino acid
        ( D ) TOPOLOGY: linear ( x i ) SEQUENCE DESCRIPTION: SEQ ID NO: 23:

Trp Tyr Trp Gly Arg Leu Ser Arg Gly Asp Ala Val Ser Leu Leu
                 5                  10                    15
Gln Gly Gln Arg His Gly Thr Phe Leu Val Arg Asp Ser Gly Ser
                20                  25                    30
Ile Pro Gly Asp Phe Val Leu Ser Val Ser Glu Ser Ser Arg Val
                35                  40                    45
Ser His Tyr Ile Val Asn Ser Leu Gly Pro Ala Gly Gly Arg Arg
                50                  55                    60
Ala Gly Gly Glu Phe Asp Ser Leu Pro Ser Leu Leu Glu Phe Tyr
                65                  70                    75
Lys Ile His Tyr Leu Asp Thr Thr Thr Leu Ile Glu Pro Val
                80                  85

( 2 ) INFORMATION FOR SEQ ID NO: 24:

( i ) SEQUENCE CHARACTERISTICS:
        ( A ) LENGTH: 1154 amino acids
        ( B ) TYPE: amino acid
        ( D ) TOPOLOGY: linear ( x i ) SEQUENCE DESCRIPTION: SEQ ID NO: 24:

Met Gln Tyr Leu Asn Ile Lys Glu Asp Cys Asn Ala Met Ala Phe Cys
                 5                  10                    15
Ala Lys Met Arg Ser Ser Lys Lys Thr Glu Val Asn Leu Glu Ala Pro
                20                  25                    30

| | | | | | | | | | | | | | | |
|---|---|---|---|---|---|---|---|---|---|---|---|---|---|---|
| Glu | Pro | Gly 35 | Val | Glu | Val | Ile | Phe 40 | Tyr | Leu | Ser | Asp | Arg 45 | Glu | Pro | Leu |
| Arg | Leu 50 | Gly | Ser | Gly | Glu | Tyr 55 | Thr | Ala | Glu | Glu | Leu 60 | Cys | Ile | Arg | Ala |
| Ala 65 | Gln | Ala | Cys | Arg | Ile 70 | Ser | Pro | Leu | Cys | His 75 | Asn | Leu | Phe | Ala | Leu 80 |
| Tyr | Asp | Glu | Asn | Thr 85 | Lys | Leu | Trp | Tyr | Ala 90 | Pro | Asn | Arg | Thr | Ile 95 | Thr |
| Val | Asp | Asp | Lys 100 | Met | Ser | Leu | Arg | Leu 105 | His | Tyr | Arg | Met | Arg 110 | Phe | Tyr |
| Phe | Thr | Asn 115 | Trp | His | Gly | Thr | Asn 120 | Asp | Asn | Glu | Gln | Ser 125 | Val | Trp | Arg |
| His | Ser 130 | Pro | Lys | Lys | Gln | Lys 135 | Asn | Gly | Tyr | Glu | Lys 140 | Lys | Lys | Ile | Pro |
| Asp 145 | Ala | Thr | Pro | Leu | Leu 150 | Asp | Ala | Ser | Ser | Leu 155 | Glu | Tyr | Leu | Phe | Ala 160 |
| Gln | Gly | Gln | Tyr | Asp 165 | Leu | Val | Lys | Cys | Leu 170 | Ala | Pro | Ile | Arg | Asp 175 | Pro |
| Lys | Thr | Glu | Gln 180 | Asp | Gly | His | Asp | Ile 185 | Glu | Asn | Glu | Cys | Leu 190 | Gly | Met |
| Ala | Val | Leu 195 | Ala | Ile | Ser | His | Tyr 200 | Ala | Met | Met | Lys | Lys 205 | Met | Gln | Leu |
| Pro | Glu 210 | Leu | Pro | Lys | Asp | Ile 215 | Ser | Tyr | Lys | Arg | Tyr 220 | Ile | Pro | Glu | Thr |
| Leu 225 | Asn | Lys | Ser | Ile | Arg 230 | Gln | Arg | Asn | Leu | Leu 235 | Thr | Arg | Met | Arg | Ile 240 |
| Asn | Asn | Val | Phe | Lys 245 | Asp | Phe | Leu | Lys | Glu 250 | Phe | Asn | Asn | Lys | Thr 255 | Ile |
| Cys | Asp | Ser | Ser 260 | Val | Ser | Thr | His | Asp 265 | Leu | Lys | Val | Lys | Tyr 270 | Leu | Ala |
| Thr | Leu | Glu 275 | Thr | Leu | Thr | Lys | His 280 | Tyr | Gly | Ala | Glu | Ile 285 | Phe | Glu | Thr |
| Ser | Met 290 | Leu | Leu | Ile | Ser | Ser 295 | Glu | Asn | Glu | Met | Asn 300 | Trp | Phe | His | Ser |
| Asn 305 | Asp | Gly | Gly | Asn | Val 310 | Leu | Tyr | Tyr | Glu | Val 315 | Met | Val | Thr | Gly | Asn 320 |
| Leu | Gly | Ile | Gln | Trp 325 | Arg | His | Lys | Pro | Asn 330 | Val | Val | Ser | Val | Glu 335 | Lys |
| Glu | Lys | Asn | Lys 340 | Leu | Lys | Arg | Lys | Lys 345 | Leu | Glu | Asn | Lys | Asp 350 | Lys | Lys |
| Asp | Glu | Glu 355 | Lys | Asn | Lys | Ile | Arg 360 | Glu | Glu | Trp | Asn | Asn 365 | Phe | Ser | Phe |
| Phe | Pro 370 | Glu | Ile | Thr | His | Ile 375 | Val | Ile | Lys | Glu | Ser 380 | Val | Val | Ser | Ile |
| Asn 385 | Lys | Gln | Asp | Asn | Lys 390 | Lys | Met | Glu | Leu | Lys 395 | Leu | Ser | Ser | His | Glu 400 |
| Glu | Ala | Leu | Ser | Phe 405 | Val | Ser | Leu | Val | Asp 410 | Gly | Tyr | Phe | Arg | Leu 415 | Thr |
| Ala | Asp | Ala | His 420 | His | Tyr | Leu | Cys | Thr 425 | Asp | Val | Ala | Pro | Pro 430 | Leu | Ile |
| Val | His | Asn 435 | Ile | Gln | Asn | Gly | Cys 440 | His | Gly | Pro | Ile | Cys 445 | Thr | Glu | Tyr |
| Ala | Ile | Asn | Lys | Leu | Arg | Gln | Glu | Gly | Ser | Glu | Glu | Gly | Met | Tyr | Val |

|     |     |     |     |     | 450 |     |     |     |     | 455 |     |     |     |     | 460 |     |     |     |     |
|-----|-----|-----|-----|-----|-----|-----|-----|-----|-----|-----|-----|-----|-----|-----|-----|-----|-----|-----|-----|
| Leu | Arg | Trp | Ser | Cys | Thr | Asp | Phe | Asp | Asn | Ile | Leu | Met | Thr | Val | Thr |
| 465 |     |     |     |     | 470 |     |     |     |     | 475 |     |     |     |     | 480 |
| Cys | Phe | Glu | Lys | Ser | Glu | Gln | Val | Gln | Gly | Ala | Gln | Lys | Gln | Phe | Lys |
|     |     |     |     | 485 |     |     |     |     | 490 |     |     |     |     | 495 |     |
| Asn | Phe | Gln | Ile | Glu | Val | Gln | Lys | Gly | Arg | Tyr | Ser | Leu | His | Gly | Ser |
|     |     |     |     | 500 |     |     |     |     | 505 |     |     |     |     | 510 |     |
| Asp | Arg | Ser | Phe | Pro | Ser | Leu | Gly | Asp | Leu | Met | Ser | His | Leu | Lys | Lys |
|     |     |     | 515 |     |     |     |     | 520 |     |     |     |     | 525 |     |     |
| Gln | Ile | Leu | Arg | Thr | Asp | Asn | Ile | Ser | Phe | Met | Leu | Lys | Arg | Cys | Cys |
|     |     |     | 530 |     |     |     |     | 535 |     |     |     |     | 540 |     |     |
| Gln | Pro | Lys | Pro | Arg | Glu | Ile | Ser | Asn | Leu | Leu | Val | Ala | Thr | Lys | Lys |
| 545 |     |     |     |     | 550 |     |     |     |     | 555 |     |     |     |     | 560 |
| Ala | Gln | Glu | Trp | Gln | Pro | Val | Tyr | Pro | Met | Ser | Gln | Leu | Ser | Phe | Asp |
|     |     |     |     | 565 |     |     |     |     | 570 |     |     |     |     | 575 |     |
| Arg | Ile | Leu | Lys | Lys | Asp | Leu | Val | Gln | Gly | Glu | His | Leu | Gly | Arg | Gly |
|     |     |     |     | 580 |     |     |     |     | 585 |     |     |     |     | 590 |     |
| Thr | Arg | Thr | His | Ile | Tyr | Ser | Gly | Thr | Leu | Met | Asp | Tyr | Lys | Asp | Asp |
|     |     |     | 595 |     |     |     |     | 600 |     |     |     |     | 605 |     |     |
| Glu | Gly | Thr | Ser | Glu | Glu | Lys | Lys | Ile | Lys | Val | Ile | Leu | Lys | Val | Leu |
|     |     |     | 610 |     |     |     |     | 615 |     |     |     |     | 620 |     |     |
| Asp | Pro | Ser | His | Arg | Asp | Ile | Ser | Leu | Ala | Phe | Phe | Glu | Ala | Ala | Ser |
| 625 |     |     |     |     | 630 |     |     |     |     | 635 |     |     |     |     | 640 |
| Met | Met | Arg | Gln | Val | Ser | His | Lys | His | Ile | Val | Tyr | Leu | Tyr | Gly | Val |
|     |     |     |     | 645 |     |     |     |     | 650 |     |     |     |     | 655 |     |
| Cys | Val | Arg | Asp | Val | Glu | Asn | Ile | Met | Val | Glu | Glu | Phe | Val | Glu | Gly |
|     |     |     | 660 |     |     |     |     | 665 |     |     |     |     | 670 |     |     |
| Gly | Pro | Leu | Asp | Leu | Phe | Met | His | Arg | Lys | Ser | Asp | Val | Leu | Thr | Thr |
|     |     |     | 675 |     |     |     |     | 680 |     |     |     |     | 685 |     |     |
| Pro | Trp | Lys | Phe | Lys | Val | Ala | Lys | Gln | Leu | Ala | Ser | Ala | Leu | Ser | Tyr |
|     |     |     | 690 |     |     |     |     | 695 |     |     |     |     | 700 |     |     |
| Leu | Glu | Asp | Lys | Asp | Leu | Val | His | Gly | Asn | Val | Cys | Thr | Lys | Asn | Leu |
| 705 |     |     |     |     | 710 |     |     |     |     | 715 |     |     |     |     | 720 |
| Leu | Leu | Ala | Arg | Glu | Gly | Ile | Asp | Ser | Glu | Cys | Gly | Pro | Phe | Ile | Lys |
|     |     |     |     | 725 |     |     |     |     | 730 |     |     |     |     | 735 |     |
| Leu | Ser | Asp | Pro | Gly | Ile | Pro | Ile | Thr | Val | Leu | Ser | Arg | Gln | Glu | Cys |
|     |     |     | 740 |     |     |     |     | 745 |     |     |     |     | 750 |     |     |
| Ile | Glu | Arg | Ile | Pro | Trp | Ile | Ala | Pro | Glu | Cys | Val | Glu | Asp | Ser | Lys |
|     |     |     | 755 |     |     |     |     | 760 |     |     |     |     | 765 |     |     |
| Asn | Leu | Ser | Val | Ala | Ala | Asp | Lys | Trp | Ser | Phe | Gly | Thr | Thr | Leu | Trp |
|     | 770 |     |     |     |     | 775 |     |     |     |     | 780 |     |     |     |     |
| Glu | Ile | Cys | Tyr | Asn | Gly | Glu | Ile | Pro | Leu | Lys | Asp | Lys | Thr | Leu | Ile |
| 785 |     |     |     |     | 790 |     |     |     |     | 795 |     |     |     |     | 800 |
| Glu | Lys | Glu | Arg | Phe | Tyr | Glu | Ser | Arg | Cys | Arg | Pro | Val | Thr | Pro | Ser |
|     |     |     |     | 805 |     |     |     |     | 810 |     |     |     |     | 815 |     |
| Cys | Lys | Glu | Leu | Ala | Asp | Leu | Met | Thr | Arg | Cys | Met | Asn | Tyr | Asp | Pro |
|     |     |     | 820 |     |     |     |     | 825 |     |     |     |     | 830 |     |     |
| Asn | Gln | Arg | Pro | Phe | Phe | Arg | Ala | Ile | Met | Arg | Asp | Ile | Asn | Lys | Leu |
|     |     | 835 |     |     |     |     | 840 |     |     |     |     | 845 |     |     |     |
| Glu | Glu | Gln | Asn | Pro | Asp | Ile | Val | Ser | Arg | Lys | Lys | Asn | Gln | Pro | Thr |
|     | 850 |     |     |     |     | 855 |     |     |     |     | 860 |     |     |     |     |
| Glu | Val | Asp | Pro | Thr | His | Phe | Glu | Lys | Arg | Phe | Leu | Lys | Arg | Ile | Arg |
| 865 |     |     |     |     | 870 |     |     |     |     | 875 |     |     |     |     | 880 |

-continued

| Asp | Leu | Gly | Glu | Gly | His | Phe | Gly | Lys | Val | Glu | Leu | Cys | Arg | Tyr | Asp |
|     |     |     |     | 885 |     |     |     | 890 |     |     |     |     |     | 895 |     |

Pro Glu Asp Asn Thr Gly Glu Gln Val Ala Val Lys Ser Leu Lys Pro
             900              905                 910

Glu Ser Gly Gly Asn His Ile Ala Asp Leu Lys Lys Glu Ile Glu Ile
         915              920              925

Leu Arg Asn Leu Tyr His Glu Asn Ile Val Lys Tyr Lys Gly Ile Cys
        930              935              940

Thr Glu Asp Gly Gly Asn Gly Ile Lys Leu Ile Met Glu Phe Leu Pro
945              950              955              960

Ser Gly Ser Leu Lys Glu Tyr Leu Pro Lys Asn Lys Asn Lys Ile Asn
                965              970              975

Leu Lys Gln Gln Leu Lys Tyr Ala Val Gln Ile Cys Lys Gly Met Asp
         980              985              990

Tyr Leu Gly Ser Arg Gln Tyr Val His Arg Asp Leu Ala Ala Arg Asn
         995              1000             1005

Val Leu Val Glu Ser Glu His Gln Val Lys Ile Gly Asp Phe Gly Leu
    1010             1015             1020

Thr Lys Ala Ile Glu Thr Asp Lys Glu Tyr Tyr Thr Val Lys Asp Asp
1025             1030             1035             1040

Arg Asp Ser Pro Val Phe Trp Tyr Ala Pro Glu Cys Leu Met Gln Ser
             1045             1050             1055

Lys Phe Tyr Ile Ala Ser Asp Val Trp Ser Phe Gly Val Thr Leu His
             1060             1065             1070

Glu Leu Leu Thr Tyr Cys Asp Ser Asp Ser Ser Pro Met Ala Leu Phe
         1075             1080             1085

Leu Lys Met Ile Gly Pro Thr His Gly Gln Met Thr Val Thr Arg Leu
         1090             1095             1100

Val Asn Thr Leu Lys Glu Gly Lys Arg Leu Pro Cys Pro Pro Asn Cys
1105             1110             1115             1120

Pro Asp Glu Val Tyr Gln Leu Met Arg Lys Cys Trp Glu Phe Gln Pro
             1125             1130             1135

Ser Asn Arg Thr Ser Phe Gln Asn Leu Ile Glu Gly Phe Glu Ala Leu
             1140             1145             1150

Leu Lys ( 2 ) INFORMATION FOR SEQ ID NO:25:

( i ) SEQUENCE CHARACTERISTICS:
        ( A ) LENGTH: 993 amino acids
        ( B ) TYPE: amino acid
        ( D ) TOPOLOGY: linear ( x i ) SEQUENCE DESCRIPTION: SEQ ID NO: 25:

Leu Leu Asp Asp Phe Val Met Ser Tyr Leu Ser Pro Gln Trp Arg
             5                   10                  15

His Asp Phe Val His Gly Trp Ile Lys Val Pro Val Thr His Glu
             20                  25                  30

Thr Gln Glu Glu Cys Leu Gly Met Ala Val Leu Asp Met Met Arg
             35                  40                  45

Ile Ala Lys Glu Lys Asp Gln Thr Pro Leu Ala Val Tyr Asn Ser
             50                  55                  60

Val Ser Tyr Lys Thr Phe Leu Pro Lys Cys Val Arg Ala Lys Ile
             65                  70                  75

Gln Asp Tyr His Ile Leu Thr Arg Lys Arg Ile Arg Tyr Arg Phe
             80                  85                  90

| | | | | | | | | | | | | |
|---|---|---|---|---|---|---|---|---|---|---|---|---|
|Arg|Arg|Phe|Ile|Gln 95|Gln|Phe|Ser|Gln 100|Cys|Lys|Ala|Thr|Ala|Arg 105|
|Asn|Leu|Lys|Leu|Lys 110|Tyr|Leu|Ile|Asn 115|Leu|Glu|Thr|Leu|Gln|Ser 120|
|Ala|Phe|Tyr|Thr|Glu 125|Gln|Phe|Glu|Val 130|Lys|Glu|Ser|Ala|Arg|Gly 135|
|Pro|Ser|Gly|Glu|Glu 140|Ile|Phe|Ala|Thr 145|Ile|Ile|Ile|Thr|Gly|Asn 150|
|Gly|Gly|Ile|Gln|Trp 155|Ser|Arg|Gly|Lys 160|His|Lys|Glu|Ser|Glu|Thr 165|
|Leu|Thr|Glu|Gln|Asp 170|Val|Gln|Leu|Tyr 175|Cys|Asp|Phe|Pro|Asp|Ile 180|
|Ile|Asp|Val|Ser|Ile 185|Lys|Gln|Ala|Asn 190|Gln|Glu|Cys|Ser|Thr|Glu 195|
|Ser|Arg|Val|Val|Thr 200|Val|His|Lys|Gln 205|Asp|Gly|Lys|Val|Leu|Glu 210|
|Ile|Glu|Leu|Ser|Ser 215|Leu|Lys|Glu|Ala 220|Leu|Ser|Phe|Val|Ser|Leu 225|
|Ile|Asp|Gly|Tyr|Tyr 230|Arg|Leu|Thr|Ala 235|Asp|Ala|His|His|Tyr|Leu 240|
|Cys|Lys|Glu|Val|Ala 245|Pro|Pro|Ala|Val 250|Phe|Glu|Asn|Ile|His|Ser 255|
|Asn|Cys|His|Gly|Pro 260|Ile|Ser|Met|Asp 265|Phe|Ala|Ile|Ser|Lys|Leu 270|
|Lys|Lys|Ala|Gly|Asn 275|Gln|Thr|Gly|Leu 280|Tyr|Val|Leu|Arg|Cys|Ser 285|
|Pro|Lys|Asp|Phe|Asn 290|Lys|Tyr|Phe|Leu 295|Thr|Phe|Ala|Val|Glu|Arg 300|
|Glu|Asn|Val|Ile|Glu 305|Tyr|Lys|His|Cys 310|Leu|Ile|Thr|Lys|Asn|Glu 315|
|Asn|Gly|Glu|Tyr|Asn 320|Leu|Ser|Gly|Thr 325|Lys|Arg|Asn|Phe|Ser|Ser 330|
|Leu|Lys|Asp|Leu|Leu 335|Asn|Cys|Tyr|Gln 340|Met|Glu|Thr|Val|Arg|Ser 345|
|Asp|Ser|Ile|Ile|Phe 350|Gln|Phe|Thr|Lys 355|Cys|Cys|Pro|Pro|Lys|Pro 360|
|Lys|Asp|Lys|Ser|Asn 365|Leu|Leu|Val|Phe 370|Arg|Thr|Asn|Gly|Val|Ser 375|
|Asp|Val|Gln|Leu|Ser 380|Pro|Thr|Leu|Gln 385|Arg|His|Asn|Asn|Val|Asn 390|
|Gln|Met|Val|Phe|His 395|Lys|Ile|Arg|Asn 400|Glu|Asp|Leu|Ile|Phe|Asn 405|
|Glu|Ser|Leu|Gly|Gln 410|Gly|Thr|Phe|Thr 415|Lys|Ile|Phe|Lys|Gly|Val 420|
|Arg|Arg|Glu|Val|Gly 425|Asp|Tyr|Gly|Gln 430|Leu|His|Glu|Thr|Glu|Val 435|
|Leu|Leu|Lys|Val|Leu 440|Asp|Lys|Ala|His 445|Arg|Asn|Tyr|Ser|Glu|Ser 450|
|Phe|Phe|Glu|Ala|Ala 455|Ser|Met|Met|Ser 460|Gln|Leu|Ser|His|Lys|His 465|
|Leu|Val|Leu|Asn|Tyr 470|Gly|Val|Cys|Val 475|Cys|Gly|Glu|Glu|Asn|Ile 480|
|Leu|Val|Gln|Glu|Phe|Val|Lys|Phe|Gly|Ser|Leu|Asp|Thr|Tyr|Leu|

|  | 485 |  |  |  |  |  | 490 |  |  |  |  | 495 |
|---|---|---|---|---|---|---|---|---|---|---|---|---|
| Lys | Lys | Asn | Lys | Asn<br>500 | Ser | Ile | Asn | Ile | Leu<br>505 | Trp | Lys | Leu | Gly | Val<br>510 |
| Ala | Lys | Gln | Leu | Ala<br>515 | Trp | Ala | Met | His | Phe<br>520 | Leu | Glu | Glu | Lys | Ser<br>525 |
| Leu | Ile | His | Gly | Asn<br>530 | Val | Cys | Ala | Lys | Asn<br>535 | Ile | Leu | Leu | Ile | Arg<br>540 |
| Glu | Glu | Asp | Arg | Arg<br>545 | Thr | Gly | Asn | Pro | Pro<br>550 | Phe | Ile | Lys | Leu | Ser<br>555 |
| Asp | Pro | Gly | Ile | Ser<br>560 | Ile | Thr | Val | Leu | Pro<br>565 | Lys | Asp | Ile | Ser | Ser<br>570 |
| Cys | Cys | Phe | Gln | Val<br>575 | Leu | Gln | Glu | Arg | Ile<br>580 | Pro | Trp | Val | Pro | Pro<br>585 |
| Glu | Cys | Ile | Glu | Asn<br>590 | Pro | Lys | Asn | Leu | Thr<br>595 | Leu | Ala | Thr | Asp | Lys<br>600 |
| Trp | Ser | Phe | Gly | Thr<br>605 | Thr | Leu | Trp | Glu | Ile<br>610 | Cys | Ser | Gly | Gly | Asp<br>615 |
| Lys | Pro | Leu | Ser | Ala<br>620 | Leu | Asp | Ser | Gln | Arg<br>625 | Lys | Leu | Gln | Phe | Tyr<br>630 |
| Glu | Asp | Lys | His | Gln<br>635 | Leu | Pro | Ala | Pro | Lys<br>640 | Trp | Thr | Glu | Leu | Ala<br>645 |
| Asn | Leu | Ile | Asn | Asn<br>650 | Cys | Met | Asp | Tyr | Glu<br>655 | Pro | Asp | Phe | Arg | Pro<br>660 |
| Ala | Phe | Arg | Ala | Val<br>665 | Ile | Arg | Asp | Leu | Asn<br>670 | Ser | Leu | Phe | Thr | Pro<br>675 |
| Asp | Tyr | Glu | Leu | Leu<br>680 | Thr | Glu | Asn | Asp | Met<br>685 | Leu | Pro | Asn | Met | Arg<br>690 |
| Ile | Gly | Ala | Leu | Gly<br>695 | Phe | Ser | Gly | Ala | Phe<br>700 | Glu | Asp | Arg | Asp | Pro<br>705 |
| Thr | Gln | Phe | Glu | Glu<br>710 | Arg | His | Leu | Lys | Phe<br>715 | Leu | Gln | Gln | Leu | Gly<br>720 |
| Lys | Gly | Asn | Phe | Gly<br>725 | Ser | Val | Glu | Met | Cys<br>730 | Arg | Tyr | Asp | Pro | Leu<br>735 |
| Gln | Asp | Asn | Thr | Gly<br>740 | Glu | Val | Val | Ala | Val<br>745 | Lys | Lys | Leu | Gln | His<br>750 |
| Ser | Thr | Glu | Glu | His<br>755 | Leu | Arg | Asp | Phe | Glu<br>760 | Arg | Glu | Ile | Glu | Ile<br>765 |
| Leu | Lys | Ser | Leu | Gln<br>770 | His | Asp | Asn | Ile | Val<br>775 | Lys | Tyr | Lys | Gly | Val<br>780 |
| Cys | Tyr | Ser | Ala | Gly<br>785 | Arg | Arg | Asn | Leu | Arg<br>790 | Leu | Ile | Met | Glu | Tyr<br>795 |
| Leu | Pro | Tyr | Gly | Ser<br>800 | Leu | Arg | Asp | Tyr | Leu<br>805 | Gln | Lys | His | Lys | Glu<br>810 |
| Arg | Ile | Asp | His | Lys<br>815 | Lys | Leu | Leu | Gln | Tyr<br>820 | Thr | Ser | Gln | Ile | Cys<br>825 |
| Lys | Gly | Met | Glu | Tyr<br>830 | Leu | Gly | Thr | Lys | Arg<br>835 | Tyr | Ile | His | Arg | Asp<br>840 |
| Leu | Ala | Thr | Arg | Asn<br>845 | Ile | Leu | Val | Glu | Asn<br>850 | Glu | Asn | Arg | Val | Lys<br>855 |
| Ile | Gly | Asp | Phe | Gly<br>860 | Leu | Thr | Lys | Val | Leu<br>865 | Pro | Gln | Asp | Lys | Glu<br>870 |
| Tyr | Tyr | Lys | Val | Lys<br>875 | Glu | Pro | Gly | Glu | Ser<br>880 | Pro | Ile | Phe | Trp | Tyr<br>885 |

| | | | | | | | | | | | | |
|---|---|---|---|---|---|---|---|---|---|---|---|---|
| Ala | Pro | Glu | Ser | Leu 890 | Thr | Glu | Ser | Lys | Phe 895 | Ser | Val | Ala | Ser | Asp 900 |
| Val | Trp | Ser | Phe | Gly 905 | Val | Val | Leu | Tyr | Glu 910 | Leu | Phe | Thr | Tyr | Ile 915 |
| Glu | Lys | Ser | Lys | Ser 920 | Pro | Pro | Val | Glu | Phe 925 | Met | Arg | Met | Ile | Gly 930 |
| Asn | Asp | Lys | Gln | Gly 935 | Gln | Met | Ile | Val | Phe 940 | His | Leu | Ile | Glu | Leu 945 |
| Leu | Lys | Ser | Asn | Gly 950 | Arg | Leu | Pro | Arg | Pro 955 | Glu | Gly | Cys | Pro | Asp 960 |
| Glu | Ile | Tyr | Val | Ile 965 | Met | Thr | Glu | Cys | Trp 970 | Asn | Asn | Asn | Val | Ser 975 |
| Gln | Arg | Pro | Ser | Phe 980 | Arg | Asp | Leu | Ser | Phe 985 | Gly | Trp | Ile | Lys | Ser 990 |
| Gly | Thr | Val | | | | | | | | | | | | |